US012806467B2

(12) United States Patent
Hull et al.

(10) Patent No.: US 12,806,467 B2
(45) Date of Patent: Nov. 24, 2026

(54) SYSTEM AND METHOD FOR USING ARTIFICIAL INTELLIGENCE AND A PAYMENT SYSTEM PERTAINING TO COMPONENTS OF MAPPED EXERCISES

(71) Applicant: ROM Technologies, Inc., Brookfield, CT (US)

(72) Inventors: Gordon Hull, Brookfield, CT (US); Steven Mason, Brookfield, CT (US); Jeff Cote, Brookfield, CT (US)

(73) Assignee: ROM Technologies, Inc., Brookfield, CT (US)

( * ) Notice: Subject to any disclaimer, the term of this patent is extended or adjusted under 35 U.S.C. 154(b) by 248 days.

(21) Appl. No.: 18/540,556

(22) Filed: Dec. 14, 2023

(65) Prior Publication Data

US 2024/0131393 A1 Apr. 25, 2024

Related U.S. Application Data

(63) Continuation of application No. 18/259,708, filed as application No. PCT/US2022/050120 on Nov. 16, 2022.

(Continued)

(51) Int. Cl.
*A63B 24/00* (2006.01)
*A63B 22/06* (2006.01)
(Continued)

(52) U.S. Cl.
CPC ...... *A63B 22/0605* (2013.01); *A63B 22/0664* (2013.01); *A63B 22/0694* (2013.01);
(Continued)

(58) Field of Classification Search
None
See application file for complete search history.

(56) References Cited

U.S. PATENT DOCUMENTS 823,712 A 6/1906 Uhlmann
4,499,900 A 2/1985 Petrofsky et al.
(Continued)

FOREIGN PATENT DOCUMENTS

CA 3193419 A1 3/2022
CN 2885238 Y 4/2007
(Continued)

OTHER PUBLICATIONS

Amiya et al., "Is Exercise Training Appropriate for Patients With Advanced Heart Failure Receiving Continuous Inotropic Infusion? A Review," 2018, pp. 1-9, vol. 12, Japan.
(Continued)

*Primary Examiner* — Shila Jalalzadeh Abyaneh
(74) *Attorney, Agent, or Firm* — Dickinson Wright PLLC; Jonathan H. Harder; Stephen A. Mason

(57) ABSTRACT

A computer-implemented system includes an electromechanical machine and a processing device communicatively coupled to motors. The processing device executes instructions to receive data comprising a treatment plan; generate, based on the data, a motion profile for an assembly of the electromechanical machine; determine, based on a prescribed exercise of the one or more prescribed exercises, components to include to enable the user to perform, using the electromechanical machine, the prescribed exercise; validate, based on the components and configuration information pertaining to the electromechanical machine, whether the motion profile associated with the prescribed exercise is achievable with respect to a threshold achievement level; and determining, based on the one or more components and the configuration information, at least one missing component needed to achieve, with respect to the threshold achievement level, the motion profile for the prescribed exercise.

18 Claims, 17 Drawing Sheets

Related U.S. Application Data

(60) Provisional application No. 63/280,835, filed on Nov. 18, 2021.

(51) Int. Cl.

| | |
|---|---|
| ***G02B 27/01*** | (2006.01) |
| ***G05B 13/02*** | (2006.01) |
| ***G06T 19/00*** | (2011.01) |
| ***G09B 5/02*** | (2006.01) |
| ***G16H 20/30*** | (2018.01) |
| ***G16H 40/60*** | (2018.01) |

(52) U.S. Cl.
CPC ...... *A63B 24/0062* (2013.01); *A63B 24/0075* (2013.01); *A63B 24/0087* (2013.01); *G02B 27/017* (2013.01); *G05B 13/0265* (2013.01); *G06T 19/006* (2013.01); *G09B 5/02* (2013.01); *G16H 20/30* (2018.01); *G16H 40/60* (2018.01); *A63B 2024/0071* (2013.01); *A63B 2024/0096* (2013.01); *A63B 2225/09* (2013.01)

(56) References Cited

U.S. PATENT DOCUMENTS

| | | | |
|---|---|---|---|
| 4,822,032 | A | 4/1989 | Whitmore et al. |
| 4,860,763 | A | 8/1989 | Schminke |
| 4,869,497 | A | 9/1989 | Stewart et al. |
| 4,932,650 | A | 6/1990 | Bingham et al. |
| 5,137,501 | A | 8/1992 | Mertesdorf |
| 5,161,430 | A | 11/1992 | Febey |
| 5,202,794 | A | 4/1993 | Schnee et al. |
| 5,240,417 | A | 8/1993 | Smithson et al. |
| 5,247,853 | A | 9/1993 | Dalebout |
| 5,256,117 | A | 10/1993 | Potts et al. |
| D342,299 | S | 12/1993 | Birrell et al. |
| 5,282,748 | A | 2/1994 | Little |
| 5,284,131 | A | 2/1994 | Gray |
| 5,316,532 | A | 5/1994 | Butler |
| 5,318,487 | A | 6/1994 | Golen |
| 5,324,241 | A | 6/1994 | Artigues et al. |
| 5,336,147 | A | 8/1994 | Sweeney, III |
| 5,338,272 | A | 8/1994 | Sweeney, III |
| 5,361,649 | A | 11/1994 | Slocum, Jr. |
| 5,429,140 | A | 7/1995 | Burdea et al. |
| 5,458,022 | A | 10/1995 | Mattfeld et al. |
| 5,487,713 | A | 1/1996 | Butler |
| 5,566,589 | A | 10/1996 | Buck |
| 5,580,338 | A | 12/1996 | Scelta et al. |
| 5,676,349 | A | 10/1997 | Wilson |
| 5,685,804 | A | 11/1997 | Whan-Tong et al. |
| 5,738,636 | A | 4/1998 | Saringer et al. |
| 5,860,941 | A | 1/1999 | Saringer et al. |
| 5,950,813 | A | 9/1999 | Hoskins et al. |
| 6,007,459 | A | 12/1999 | Burgess |
| 6,053,847 | A | 4/2000 | Stearns et al. |
| 6,077,201 | A | 6/2000 | Cheng |
| 6,102,834 | A | 8/2000 | Chen |
| 6,110,130 | A | 8/2000 | Kramer |
| 6,155,958 | A | 12/2000 | Goldberg |
| 6,162,189 | A | 12/2000 | Girone et al. |
| 6,182,029 | B1 | 1/2001 | Friedman |
| D438,580 | S | 3/2001 | Shaw |
| 6,253,638 | B1 | 7/2001 | Bermudez |
| 6,267,735 | B1 | 7/2001 | Blanchard et al. |
| 6,273,863 | B1 | 8/2001 | Avni et al. |
| D450,100 | S | 11/2001 | Hsu |
| D450,101 | S | 11/2001 | Hsu |
| D451,972 | S | 12/2001 | Easley |
| D452,285 | S | 12/2001 | Easley |
| D454,605 | S | 3/2002 | Lee |
| 6,371,891 | B1 | 4/2002 | Speas |
| D459,776 | S | 7/2002 | Lee |
| 6,413,190 | B1 | 7/2002 | Wood et al. |
| 6,430,436 | B1 | 8/2002 | Richter |
| 6,436,058 | B1 | 8/2002 | Krahner et al. |
| 6,450,923 | B1 | 9/2002 | Vatti |
| 6,474,193 | B1 | 11/2002 | Farney |
| 6,491,649 | B1 | 12/2002 | Ombrellaro |
| 6,514,085 | B2 | 2/2003 | Slattery et al. |
| 6,535,861 | B1 | 3/2003 | OConnor et al. |
| 6,543,309 | B2 | 4/2003 | Heim |
| 6,589,139 | B1 | 7/2003 | Butterworth |
| 6,601,016 | B1 | 7/2003 | Brown et al. |
| 6,602,191 | B2 | 8/2003 | Quy |
| 6,613,000 | B1 | 9/2003 | Reinkensmeyer et al. |
| 6,626,800 | B1 | 9/2003 | Casler |
| 6,626,805 | B1 | 9/2003 | Lightbody |
| 6,640,122 | B2 | 10/2003 | Manoli |
| 6,640,662 | B1 | 11/2003 | Baxter |
| 6,652,425 | B1 | 11/2003 | Martin et al. |
| 6,659,946 | B1 | 12/2003 | Batchelor et al. |
| 6,820,517 | B1 | 11/2004 | Farney |
| 6,865,969 | B2 | 3/2005 | Stevens |
| 6,890,312 | B1 | 5/2005 | Priester et al. |
| 6,895,834 | B1 | 5/2005 | Baatz |
| 6,902,513 | B1 | 6/2005 | McClure |
| 7,058,453 | B2 | 6/2006 | Nelson et al. |
| 7,063,643 | B2 | 6/2006 | Arai |
| 7,156,665 | B1 | 1/2007 | OConnor et al. |
| 7,156,780 | B1 | 1/2007 | Fuchs et al. |
| 7,169,085 | B1 | 1/2007 | Killin et al. |
| 7,204,788 | B2 | 4/2007 | Andrews |
| 7,209,886 | B2 | 4/2007 | Kimmel |
| 7,226,394 | B2 | 6/2007 | Johnson |
| RE39,904 | E | 10/2007 | Lee |
| 7,406,003 | B2 | 7/2008 | Burkhardt et al. |
| 7,507,188 | B2 | 3/2009 | Nurre |
| 7,594,879 | B2 | 9/2009 | Johnson |
| 7,628,730 | B1 | 12/2009 | Watterson et al. |
| 7,778,851 | B2 | 8/2010 | Schoenberg et al. |
| 7,809,601 | B2 | 10/2010 | Shaya et al. |
| 7,833,135 | B2 | 11/2010 | Radow et al. |
| 7,837,472 | B1 | 11/2010 | Elsmore et al. |
| 7,890,342 | B1 | 2/2011 | Yruko |
| 7,955,219 | B2 | 6/2011 | Birrell et al. |
| 7,969,315 | B1 | 6/2011 | Ross et al. |
| 7,988,599 | B2 | 8/2011 | Ainsworth et al. |
| 8,007,405 | B2 | 8/2011 | Burnfield |
| 8,012,107 | B2 | 9/2011 | Einav et al. |
| 8,021,270 | B2 | 9/2011 | D'Eredita |
| 8,038,578 | B2 | 10/2011 | Olrik et al. |
| 8,079,937 | B2 | 12/2011 | Bedell |
| 8,113,991 | B2 | 2/2012 | Kutliroff |
| 8,172,724 | B2 | 5/2012 | Solomon |
| 8,177,732 | B2 | 5/2012 | Einav et al. |
| 8,244,566 | B1 | 8/2012 | Coley |
| 8,287,434 | B2 | 10/2012 | Zavadsky et al. |
| 8,298,123 | B2 | 10/2012 | Hickman |
| 8,371,990 | B2 | 2/2013 | Shea |
| 8,396,804 | B1 | 3/2013 | Dala |
| 8,419,593 | B2 | 4/2013 | Ainsworth et al. |
| 8,465,398 | B2 | 6/2013 | Lee et al. |
| 8,503,086 | B2 | 8/2013 | French |
| 8,506,458 | B2 | 8/2013 | Dugan |
| 8,540,515 | B2 | 9/2013 | Williams et al. |
| 8,540,516 | B2 | 9/2013 | Williams et al. |
| 8,556,778 | B1 | 10/2013 | Dugan |
| 8,607,465 | B1 | 12/2013 | Edwards |
| 8,613,689 | B2 | 12/2013 | Dyer et al. |
| 8,615,529 | B2 | 12/2013 | Reiner |
| 8,672,812 | B2 | 3/2014 | Dugan |
| 8,751,264 | B2 | 6/2014 | Beraja et al. |
| 8,784,273 | B2 | 7/2014 | Dugan |
| 8,818,496 | B2 | 8/2014 | Dziubinski et al. |
| 8,823,448 | B1 | 9/2014 | Shen |
| 8,845,493 | B2 | 9/2014 | Watterson et al. |
| 8,849,681 | B2 | 9/2014 | Hargrove et al. |
| 8,864,628 | B2 | 10/2014 | Boyette et al. |
| 8,893,287 | B2 | 11/2014 | Gjonej et al. |
| 8,905,925 | B2 | 12/2014 | Beck et al. |
| 8,979,711 | B2 | 3/2015 | Dugan |
| 9,044,630 | B1 | 6/2015 | Lampert et al. |
| 9,167,281 | B2 | 10/2015 | Petrov et al. |

(56) References Cited

U.S. PATENT DOCUMENTS

| | | | |
|---|---|---|---|
| D744,050 | S | 11/2015 | Colburn |
| 9,177,106 | B2 | 11/2015 | Smith et al. |
| 9,248,071 | B1 | 2/2016 | Brenda |
| 9,256,711 | B2 | 2/2016 | Horseman |
| 9,272,091 | B2 | 3/2016 | Skelton |
| 9,272,185 | B2 | 3/2016 | Dugan |
| 9,283,434 | B1 | 3/2016 | Wu |
| 9,295,878 | B2 | 3/2016 | Corbalis et al. |
| 9,311,789 | B1 | 4/2016 | Gwin |
| 9,312,907 | B2 | 4/2016 | Auchinleck et al. |
| 9,367,668 | B2 | 6/2016 | Flynt et al. |
| 9,409,054 | B2 | 8/2016 | Dugan |
| 9,420,956 | B2 | 8/2016 | Gopalakrishnan et al. |
| 9,443,205 | B2 | 9/2016 | Wall |
| 9,474,935 | B2 | 10/2016 | Abbondanza et al. |
| 9,480,873 | B2 | 11/2016 | Chuang |
| 9,481,428 | B2 | 11/2016 | Gros |
| 9,514,277 | B2 | 12/2016 | Hassing et al. |
| 9,566,472 | B2 | 2/2017 | Dugan |
| 9,579,056 | B2 | 2/2017 | Rosenbek et al. |
| 9,629,558 | B2 | 4/2017 | Yuen et al. |
| 9,640,057 | B1 | 5/2017 | Ross |
| 9,707,147 | B2 | 7/2017 | Levital et al. |
| 9,713,744 | B2 | 7/2017 | Suzuki |
| D794,142 | S | 8/2017 | Zhou |
| 9,717,947 | B2 | 8/2017 | Lin |
| 9,737,761 | B1 | 8/2017 | Govindarajan |
| 9,773,330 | B1 | 9/2017 | Douglas |
| 9,782,621 | B2 | 10/2017 | Chiang et al. |
| 9,802,076 | B2 | 10/2017 | Murray et al. |
| 9,802,081 | B2 | 10/2017 | Ridgel et al. |
| 9,813,239 | B2 | 11/2017 | Chee et al. |
| 9,826,908 | B2 | 11/2017 | Wu |
| 9,827,445 | B2 | 11/2017 | Marcos et al. |
| 9,849,337 | B2 | 12/2017 | Roman et al. |
| 9,868,028 | B2 | 1/2018 | Shin |
| 9,872,087 | B2 | 1/2018 | DelloStritto et al. |
| 9,872,637 | B2 | 1/2018 | Kording et al. |
| 9,914,053 | B2 | 3/2018 | Dugan |
| 9,919,198 | B2 | 3/2018 | Romeo et al. |
| 9,937,382 | B2 | 4/2018 | Dugan |
| 9,939,784 | B1 | 4/2018 | Berardinelli |
| 9,974,478 | B1 | 5/2018 | Brokaw |
| 9,977,587 | B2 | 5/2018 | Mountain |
| 9,993,181 | B2 | 6/2018 | Ross |
| 9,997,082 | B2 | 6/2018 | Kaleal |
| 10,004,946 | B2 | 6/2018 | Ross |
| 10,026,052 | B2 | 7/2018 | Brown et al. |
| 10,055,550 | B2 | 8/2018 | Goetz |
| 10,058,473 | B2 | 8/2018 | Oshima et al. |
| 10,074,148 | B2 | 9/2018 | Cashman et al. |
| 10,089,443 | B2 | 10/2018 | Miller et al. |
| 10,111,643 | B2 | 10/2018 | Shulhauser et al. |
| 10,130,311 | B1 | 11/2018 | De Sapio et al. |
| 10,137,328 | B2 | 11/2018 | Baudhuin |
| 10,143,395 | B2 | 12/2018 | Chakravarthy et al. |
| 10,155,134 | B2 | 12/2018 | Dugan |
| 10,159,872 | B2 | 12/2018 | Sasaki et al. |
| 10,173,094 | B2 | 1/2019 | Gomberg et al. |
| 10,173,095 | B2 | 1/2019 | Gomberg et al. |
| 10,173,096 | B2 | 1/2019 | Gomberg et al. |
| 10,173,097 | B2 | 1/2019 | Gomberg et al. |
| 10,182,726 | B2 | 1/2019 | Ahmed et al. |
| 10,198,928 | B1 | 2/2019 | Ross et al. |
| 10,226,663 | B2 | 3/2019 | Gomberg et al. |
| 10,231,664 | B2 | 3/2019 | Ganesh |
| 10,244,990 | B2 | 4/2019 | Hu et al. |
| 10,322,315 | B2 | 6/2019 | Foley et al. |
| 10,325,070 | B2 | 6/2019 | Beale et al. |
| 10,327,697 | B1 | 6/2019 | Stein et al. |
| 10,362,940 | B2 | 7/2019 | Tran |
| 10,369,021 | B2 | 8/2019 | Zoss et al. |
| 10,380,866 | B1 | 8/2019 | Ross et al. |
| 10,413,222 | B1 | 9/2019 | Kayyall |
| 10,424,033 | B2 | 9/2019 | Romeo |

| | | | |
|---|---|---|---|
| 10,430,552 | B2 | 10/2019 | Mihai |
| D866,957 | S | 11/2019 | Ross et al. |
| 10,468,131 | B2 | 11/2019 | Macoviak et al. |
| 10,475,323 | B1 | 11/2019 | Ross |
| 10,475,537 | B2 | 11/2019 | Purdie et al. |
| 10,492,977 | B2 | 12/2019 | Kapure et al. |
| 10,507,358 | B2 | 12/2019 | Kinnunen et al. |
| 10,542,914 | B2 | 1/2020 | Forth et al. |
| 10,546,467 | B1 | 1/2020 | Luciano, Jr. et al. |
| 10,569,122 | B2 | 2/2020 | Johnson |
| 10,572,626 | B2 | 2/2020 | Balram |
| 10,576,331 | B2 | 3/2020 | Kuo |
| 10,625,114 | B2 | 4/2020 | Ercanbrack |
| 10,646,746 | B1 | 5/2020 | Gomberg et al. |
| 10,660,534 | B2 | 5/2020 | Lee et al. |
| 10,678,890 | B2 | 6/2020 | Bitran et al. |
| 10,685,092 | B2 | 6/2020 | Paparella et al. |
| 10,741,285 | B2 | 8/2020 | Moturu |
| 10,777,200 | B2 | 9/2020 | Will et al. |
| D899,605 | S | 10/2020 | Ross et al. |
| 10,792,495 | B2 | 10/2020 | Izvorski et al. |
| 10,814,170 | B2 | 10/2020 | Wang et al. |
| 10,857,426 | B1 | 12/2020 | Neumann |
| 10,867,695 | B2 | 12/2020 | Neagle |
| 10,874,905 | B2 | 12/2020 | Belson et al. |
| D907,143 | S | 1/2021 | Ach et al. |
| 10,881,911 | B2 | 1/2021 | Kwon et al. |
| 10,902,944 | B1 | 1/2021 | Casey |
| 10,918,332 | B2 | 2/2021 | Belson et al. |
| 10,931,643 | B1 | 2/2021 | Neumann |
| 10,987,176 | B2 | 4/2021 | Poltaretskyi et al. |
| 10,991,463 | B2 | 4/2021 | Kutzko et al. |
| 11,000,735 | B2 | 5/2021 | Orady et al. |
| 11,045,709 | B2 | 6/2021 | Putnam |
| 11,065,170 | B2 | 7/2021 | Yang et al. |
| 11,065,527 | B2 | 7/2021 | Putnam |
| 11,069,436 | B2 | 7/2021 | Mason et al. |
| 11,071,597 | B2 | 7/2021 | Posnack et al. |
| 11,075,000 | B2 | 7/2021 | Mason et al. |
| D928,635 | S | 8/2021 | Hacking et al. |
| 11,087,865 | B2 | 8/2021 | Mason et al. |
| 11,094,400 | B2 | 8/2021 | Riley et al. |
| 11,101,028 | B2 | 8/2021 | Mason et al. |
| 11,107,591 | B1 | 8/2021 | Mason |
| 11,139,060 | B2 | 10/2021 | Mason et al. |
| 11,185,735 | B2 | 11/2021 | Arn et al. |
| 11,185,738 | B1 | 11/2021 | McKirdy et al. |
| D939,096 | S | 12/2021 | Lee |
| D939,644 | S | 12/2021 | Ach et al. |
| D940,797 | S | 1/2022 | Ach et al. |
| D940,891 | S | 1/2022 | Lee |
| 11,229,727 | B2 | 1/2022 | Tatonetti |
| 11,229,788 | B1 | 1/2022 | John |
| 11,265,234 | B2 | 3/2022 | Guaneri et al. |
| 11,270,795 | B2 | 3/2022 | Mason et al. |
| 11,272,879 | B2 | 3/2022 | Wiedenhoefer et al. |
| 11,278,766 | B2 | 3/2022 | Lee |
| 11,282,599 | B2 | 3/2022 | Mason et al. |
| 11,282,604 | B2 | 3/2022 | Mason et al. |
| 11,282,608 | B2 | 3/2022 | Mason et al. |
| 11,284,797 | B2 | 3/2022 | Mason et al. |
| D948,639 | S | 4/2022 | Ach et al. |
| 11,295,848 | B2 | 4/2022 | Mason et al. |
| 11,309,085 | B2 | 4/2022 | Mason et al. |
| 11,317,975 | B2 | 5/2022 | Mason et al. |
| 11,325,005 | B2 | 5/2022 | Mason et al. |
| 11,328,807 | B2 | 5/2022 | Mason et al. |
| 11,331,537 | B1 | 5/2022 | Ketchell |
| 11,337,648 | B2 | 5/2022 | Mason |
| 11,347,829 | B1 | 5/2022 | Sclar et al. |
| 11,348,683 | B2 | 5/2022 | Guaneri et al. |
| 11,370,328 | B2 | 6/2022 | Main |
| 11,404,150 | B2 | 8/2022 | Guaneri et al. |
| 11,410,768 | B2 | 8/2022 | Mason et al. |
| 11,422,841 | B2 | 8/2022 | Jeong |
| 11,437,137 | B1 | 9/2022 | Harris |
| 11,495,355 | B2 | 11/2022 | McNutt et al. |
| 11,508,258 | B2 | 11/2022 | Nakashima et al. |
| 11,524,210 | B2 | 12/2022 | Kim et al. |

(56) References Cited

U.S. PATENT DOCUMENTS 11,527,326 B2 12/2022 McNair et al.
11,532,402 B2 12/2022 Farley et al.
11,534,654 B2 12/2022 Silcock et al.
D976,339 S 1/2023 Li
11,553,969 B1 1/2023 Lang et al.
11,621,067 B1 4/2023 Nolan
11,636,944 B2 4/2023 Hanrahan et al.
11,654,327 B2 5/2023 Phillips et al.
11,663,673 B2 5/2023 Pyles
11,673,024 B2 6/2023 Omid-Zohoor
11,701,548 B2 7/2023 Posnack et al.
11,756,666 B2 9/2023 Rosenberg
11,776,676 B2 10/2023 Savolainen
11,944,579 B2 4/2024 Sankai
11,957,960 B2 4/2024 Bissonnette et al.
12,004,871 B1 6/2024 Fazeli
12,020,511 B1 6/2024 Denton et al.
12,042,714 B1 7/2024 Campbell
12,057,210 B2 8/2024 Akinola et al.
12,176,091 B2 12/2024 Rosenberg
12,205,704 B2 1/2025 Hosoi et al.
2002/0010596 A1 1/2002 Matory
2002/0072452 A1 6/2002 Torkelson
2002/0123715 A1 9/2002 Sorenson
2002/0143279 A1 10/2002 Porter et al.
2002/0160883 A1 10/2002 Dugan
2002/0183599 A1 12/2002 Castellanos
2003/0013072 A1 1/2003 Thomas
2003/0036683 A1 2/2003 Kehr et al.
2003/0064860 A1 4/2003 Yamashita et al.
2003/0064863 A1 4/2003 Chen
2003/0083596 A1 5/2003 Kramer et al.
2003/0092536 A1 5/2003 Romanelli et al.
2003/0181832 A1 9/2003 Carnahan et al.
2004/0072652 A1 4/2004 Alessandri et al.
2004/0102931 A1 5/2004 Ellis et al.
2004/0106502 A1 6/2004 Sher
2004/0147969 A1 7/2004 Mann et al.
2004/0172093 A1 9/2004 Rummerfield
2004/0194572 A1 10/2004 Kim
2004/0197727 A1 10/2004 Sachdeva et al.
2004/0204959 A1 10/2004 Moreano et al.
2005/0015118 A1 1/2005 Davis et al.
2005/0020411 A1 1/2005 Andrews
2005/0043145 A1 2/2005 Anderson
2005/0043153 A1 2/2005 Krietzman
2005/0049122 A1 3/2005 Vallone et al.
2005/0085346 A1 4/2005 Johnson
2005/0085353 A1 4/2005 Johnson
2005/0143641 A1 6/2005 Tashiro
2005/0274220 A1 12/2005 Reboullet
2006/0003871 A1 1/2006 Houghton et al.
2006/0046905 A1 3/2006 Doody et al.
2006/0064329 A1 3/2006 Abolfathi et al.
2006/0129432 A1 6/2006 Choi et al.
2006/0199700 A1 9/2006 LaStayo et al.
2006/0247095 A1 11/2006 Rummerfield
2006/0277074 A1 12/2006 Einav
2007/0042868 A1 2/2007 Fisher et al.
2007/0118389 A1 5/2007 Shipon
2007/0118406 A1 5/2007 Killin et al.
2007/0136099 A1 6/2007 Neligh
2007/0137307 A1 6/2007 Gruben et al.
2007/0173392 A1 7/2007 Stanford
2007/0194939 A1 8/2007 Alvarez et al.
2007/0271065 A1 11/2007 Gupta et al.
2007/0287597 A1 12/2007 Cameron
2008/0021834 A1 1/2008 Holla et al.
2008/0077619 A1 3/2008 Gilley et al.
2008/0082356 A1 4/2008 Friedlander et al.
2008/0096726 A1 4/2008 Riley et al.
2008/0103023 A1* 5/2008 Chung ................ G11B 27/034
482/3
2008/0153592 A1 6/2008 James-Herbert
2008/0161166 A1 7/2008 Lo
2008/0161733 A1 7/2008 Einav et al.
2008/0183500 A1 7/2008 Banigan
2008/0281633 A1 11/2008 Burdea et al.
2008/0300914 A1 12/2008 Karkanias et al.
2008/0312040 A1 12/2008 Ochi
2008/0319330 A1 12/2008 Juntunen
2009/0011907 A1 1/2009 Radow et al.
2009/0037334 A1 2/2009 Hsu
2009/0058635 A1 3/2009 LaLonde et al.
2009/0070138 A1 3/2009 Langheier et al.
2009/0157617 A1 6/2009 Herlocker
2009/0211395 A1 8/2009 Mule
2009/0270227 A1 10/2009 Ashby et al.
2009/0287503 A1 11/2009 Angell et al.
2009/0299766 A1 12/2009 Friedlander et al.
2010/0048358 A1 2/2010 Tchao et al.
2010/0062818 A1 3/2010 Haughay, Jr.
2010/0076786 A1 3/2010 Dalton et al.
2010/0121160 A1 5/2010 Stark et al.
2010/0173747 A1 7/2010 Chen et al.
2010/0216168 A1 8/2010 Heinzman et al.
2010/0234184 A1 9/2010 Le Page et al.
2010/0248899 A1 9/2010 Bedell et al.
2010/0248905 A1 9/2010 Lu
2010/0262052 A1 10/2010 Lunau et al.
2010/0268304 A1 10/2010 Matos
2010/0293003 A1 11/2010 Abbo
2010/0298102 A1 11/2010 Bosecker et al.
2010/0332583 A1 12/2010 Szabo
2011/0010188 A1 1/2011 Yoshikawa et al.
2011/0047108 A1 2/2011 Chakrabarty et al.
2011/0082007 A1 4/2011 Birrell
2011/0087137 A1 4/2011 Hanoun
2011/0119212 A1 5/2011 De Bruin et al.
2011/0172059 A1 7/2011 Watterson et al.
2011/0195819 A1 8/2011 Shaw et al.
2011/0218462 A1 9/2011 Smith
2011/0218814 A1 9/2011 Coats
2011/0275483 A1 11/2011 Dugan
2011/0281249 A1 11/2011 Gammell et al.
2011/0306846 A1 12/2011 Osorio
2012/0041771 A1 2/2012 Cosentino et al.
2012/0065987 A1 3/2012 Farooq et al.
2012/0116258 A1 5/2012 Lee
2012/0130196 A1 5/2012 Jain et al.
2012/0130197 A1 5/2012 Kugler et al.
2012/0167709 A1 7/2012 Chen et al.
2012/0183939 A1 7/2012 Aragones et al.
2012/0190502 A1 7/2012 Paulus et al.
2012/0232438 A1 9/2012 Cataldi et al.
2012/0248346 A1 10/2012 Chowdhary
2012/0253241 A1 10/2012 Levital
2012/0259648 A1 10/2012 Mallon et al.
2012/0259649 A1 10/2012 Mallon et al.
2012/0278759 A1 11/2012 Curl et al.
2012/0295240 A1 11/2012 Walker et al.
2012/0296455 A1 11/2012 Ohnemus et al.
2012/0310667 A1 12/2012 Altman et al.
2013/0066647 A1 3/2013 Andrie
2013/0079925 A1 3/2013 Alaklabi et al.
2013/0083054 A1 4/2013 Bayouk
2013/0108594 A1 5/2013 Martin-Rendon et al.
2013/0110545 A1 5/2013 Smallwood
2013/0123071 A1 5/2013 Rhea
2013/0123667 A1 5/2013 Komatireddy et al.
2013/0137550 A1 5/2013 Skinner et al.
2013/0137552 A1 5/2013 Kemp et al.
2013/0158368 A1 6/2013 Pacione
2013/0165195 A1 6/2013 Watterson
2013/0171599 A1 7/2013 Bleich
2013/0173305 A1 7/2013 Hyde
2013/0178334 A1 7/2013 Brammer
2013/0211281 A1 8/2013 Ross et al.
2013/0211774 A1* 8/2013 Bentley .................. G01P 13/00
702/145
2013/0253943 A1 9/2013 Lee et al.
2013/0274069 A1 10/2013 Watterson et al.
2013/0296987 A1 11/2013 Rogers et al.
2013/0318027 A1 11/2013 Almogy et al.

(56) References Cited

U.S. PATENT DOCUMENTS

2013/0332616 A1 12/2013 Landwehr
2013/0345025 A1 12/2013 van der Merwe
2014/0006042 A1 1/2014 Keefe et al.
2014/0011640 A1 1/2014 Dugan
2014/0031174 A1 1/2014 Huang
2014/0038781 A1 2/2014 Foley et al.
2014/0062900 A1 3/2014 Kaula et al.
2014/0073486 A1 3/2014 Ahmed et al.
2014/0074179 A1 3/2014 Heldman et al.
2014/0089836 A1 3/2014 Damani et al.
2014/0108035 A1 4/2014 Akbay
2014/0113261 A1 4/2014 Akiba
2014/0113768 A1 4/2014 Lin et al.
2014/0135173 A1 5/2014 Watterson
2014/0149129 A1 5/2014 Getchius
2014/0155129 A1 6/2014 Dugan
2014/0163439 A1 6/2014 Uryash et al.
2014/0170607 A1 6/2014 Hsiao
2014/0172442 A1 6/2014 Broderick
2014/0172460 A1 6/2014 Kohli
2014/0172514 A1 6/2014 Schumann et al.
2014/0188009 A1 7/2014 Lange et al.
2014/0194250 A1 7/2014 Reich et al.
2014/0194251 A1 7/2014 Reich et al.
2014/0200414 A1 7/2014 Osorio
2014/0207264 A1 7/2014 Quy
2014/0207486 A1 7/2014 Carty et al.
2014/0228649 A1 8/2014 Rayner et al.
2014/0246499 A1 9/2014 Proud et al.
2014/0256511 A1 9/2014 Smith
2014/0257837 A1 9/2014 Walker et al.
2014/0274565 A1 9/2014 Boyette et al.
2014/0274622 A1 9/2014 Leonhard
2014/0275816 A1 9/2014 Sandmore
2014/0309083 A1 10/2014 Dugan
2014/0322686 A1 10/2014 Kang
2014/0347265 A1 11/2014 Aimone et al.
2014/0372133 A1 12/2014 Austrum et al.
2015/0025816 A1 1/2015 Ross
2015/0045700 A1 2/2015 Cavanagh et al.
2015/0046192 A1 2/2015 Raduchel
2015/0051721 A1 2/2015 Cheng
2015/0065213 A1 3/2015 Dugan
2015/0088544 A1 3/2015 Goldberg
2015/0094192 A1 4/2015 Skwortsow et al.
2015/0099458 A1 4/2015 Weisner et al.
2015/0099952 A1 4/2015 Lain et al.
2015/0111644 A1 4/2015 Larson
2015/0112230 A1 4/2015 Iglesias
2015/0112702 A1 4/2015 Joao et al.
2015/0130830 A1 5/2015 Nagasaki
2015/0141200 A1 5/2015 Murray et al.
2015/0142142 A1 5/2015 Campana Aguilera et al.
2015/0149217 A1 5/2015 Kaburagi
2015/0151162 A1 6/2015 Dugan
2015/0157918 A1 6/2015 Tracy
2015/0157938 A1 6/2015 Domansky et al.
2015/0161331 A1 6/2015 Oleynik
2015/0161876 A1 6/2015 Castillo
2015/0174446 A1 6/2015 Chiang
2015/0196804 A1 7/2015 Koduri
2015/0199494 A1 7/2015 Koduri
2015/0217056 A1 8/2015 Kadavy et al.
2015/0251074 A1 9/2015 Ahmed et al.
2015/0257679 A1 9/2015 Ross
2015/0265209 A1 9/2015 Zhang
2015/0273272 A1 10/2015 Wang
2015/0290061 A1 10/2015 Stafford et al.
2015/0331997 A1 11/2015 Joao
2015/0335950 A1 11/2015 Eder
2015/0335951 A1 11/2015 Eder
2015/0339442 A1 11/2015 Oleynik
2015/0341812 A1 11/2015 Dion et al.
2015/0351664 A1 12/2015 Ross
2015/0351665 A1 12/2015 Ross
2015/0359467 A1 12/2015 Tran
2015/0360069 A1 12/2015 Marti et al.
2015/0379232 A1 12/2015 Mainwaring et al.
2015/0379430 A1 12/2015 Dirac et al.
2016/0004820 A1 1/2016 Moore
2016/0007885 A1 1/2016 Basta
2016/0009338 A1 1/2016 Biderman
2016/0015995 A1 1/2016 Leung et al.
2016/0023081 A1 1/2016 Popa-Simil et al.
2016/0045170 A1 2/2016 Migita
2016/0081594 A1 3/2016 Gaddipati
2016/0084869 A1 3/2016 Yuen
2016/0086500 A1 3/2016 Kaleal, III
2016/0096073 A1 4/2016 Rahman et al.
2016/0117471 A1 4/2016 Belt et al.
2016/0132643 A1 5/2016 Radhakrishna et al.
2016/0143593 A1 5/2016 Fu et al.
2016/0151670 A1 6/2016 Dugan
2016/0158534 A1 6/2016 Guarraia et al.
2016/0166833 A1 6/2016 Bum
2016/0166881 A1 6/2016 Ridgel et al.
2016/0193306 A1 7/2016 Rabovsky et al.
2016/0197918 A1 7/2016 Turgeman et al.
2016/0232321 A1 8/2016 Silverman
2016/0250519 A1 9/2016 Watterson
2016/0275259 A1 9/2016 Nolan et al.
2016/0287166 A1 10/2016 Tran
2016/0294837 A1 10/2016 Turgeman
2016/0302666 A1 10/2016 Shaya
2016/0302721 A1 10/2016 Wiedenhoefer et al.
2016/0317869 A1 11/2016 Dugan
2016/0322078 A1 11/2016 Bose et al.
2016/0325140 A1 11/2016 Wu
2016/0332028 A1 11/2016 Melnik
2016/0345841 A1 12/2016 Jang et al.
2016/0361025 A1 12/2016 Reicher et al.
2016/0361597 A1 12/2016 Cole et al.
2017/0000422 A1 1/2017 Moturu et al.
2017/0004260 A1 1/2017 Moturu et al.
2017/0011179 A1 1/2017 Arshad et al.
2017/0017760 A1 1/2017 Freese et al.
2017/0032092 A1 2/2017 Mink et al.
2017/0033375 A1 2/2017 Ohmori et al.
2017/0042467 A1 2/2017 Herr et al.
2017/0043160 A1 2/2017 Goodall et al.
2017/0046488 A1 2/2017 Pereira
2017/0065851 A1 3/2017 Deluca et al.
2017/0069223 A1 3/2017 Cramer et al.
2017/0080281 A1 3/2017 Hartman
2017/0080320 A1 3/2017 Smith
2017/0091422 A1 3/2017 Kumar et al.
2017/0095670 A1 4/2017 Ghaffari et al.
2017/0095692 A1 4/2017 Chang et al.
2017/0095693 A1 4/2017 Chang et al.
2017/0097964 A1 4/2017 Sorrentino
2017/0100637 A1 4/2017 Princen et al.
2017/0106242 A1 4/2017 Dugan
2017/0113092 A1 4/2017 Johnson
2017/0128769 A1 5/2017 Long et al.
2017/0132947 A1 5/2017 Maeda et al.
2017/0136296 A1 5/2017 Barrera et al.
2017/0136297 A1 5/2017 Penie
2017/0136298 A1 5/2017 Bae
2017/0143261 A1 5/2017 Wiedenhoefer et al.
2017/0143262 A1 5/2017 Kurunmaki
2017/0147752 A1 5/2017 Toru
2017/0147789 A1 5/2017 Wiedenhoefer et al.
2017/0148297 A1 5/2017 Ross
2017/0168555 A1 6/2017 Munoz et al.
2017/0169177 A1 6/2017 Beale
2017/0173391 A1 6/2017 Wiebe
2017/0181698 A1 6/2017 Wiedenhoefer et al.
2017/0190052 A1 7/2017 Jaekel et al.
2017/0200264 A1 7/2017 Park
2017/0203157 A1 7/2017 Volkerink
2017/0209766 A1 7/2017 Riley et al.
2017/0228517 A1 8/2017 Saliman et al.
2017/0235882 A1 8/2017 Orlov et al.
2017/0235906 A1 8/2017 Dorris et al.

(56) References Cited

U.S. PATENT DOCUMENTS

| | | | |
|---|---|---|---|
| 2017/0243028 | A1 | 8/2017 | LaFever et al. |
| 2017/0258370 | A1 | 9/2017 | Plotnik-Peleg et al. |
| 2017/0262604 | A1 | 9/2017 | Francois |
| 2017/0265800 | A1 | 9/2017 | Auchinleck et al. |
| 2017/0266501 | A1 | 9/2017 | Sanders et al. |
| 2017/0277841 | A1 | 9/2017 | Shankar et al. |
| 2017/0278209 | A1 | 9/2017 | Olsen et al. |
| 2017/0282015 | A1 | 10/2017 | Wicks et al. |
| 2017/0283508 | A1 | 10/2017 | Demopulos et al. |
| 2017/0291067 | A1 | 10/2017 | Jang et al. |
| 2017/0296861 | A1 | 10/2017 | Burkinshaw |
| 2017/0300654 | A1 | 10/2017 | Stein et al. |
| 2017/0312614 | A1 | 11/2017 | Tran et al. |
| 2017/0323481 | A1 | 11/2017 | Tran et al. |
| 2017/0329917 | A1 | 11/2017 | McRaith et al. |
| 2017/0329933 | A1 | 11/2017 | Brust |
| 2017/0333755 | A1 | 11/2017 | Rider |
| 2017/0337033 | A1 | 11/2017 | Duyan et al. |
| 2017/0337334 | A1 | 11/2017 | Stanczak |
| 2017/0344726 | A1 | 11/2017 | Duffy et al. |
| 2017/0347923 | A1 | 12/2017 | Roh |
| 2017/0352157 | A1 | 12/2017 | Madabhushi |
| 2017/0360586 | A1 | 12/2017 | Dempers et al. |
| 2017/0361165 | A1 | 12/2017 | Miller et al. |
| 2017/0367606 | A1 | 12/2017 | Lee |
| 2017/0368413 | A1 | 12/2017 | Shavit |
| 2018/0017806 | A1 | 1/2018 | Wang et al. |
| 2018/0028896 | A1 | 2/2018 | Ray |
| 2018/0036591 | A1 | 2/2018 | King et al. |
| 2018/0036593 | A1 | 2/2018 | Ridgel et al. |
| 2018/0052962 | A1 | 2/2018 | Van Der Koijk et al. |
| 2018/0052968 | A1 | 2/2018 | Hickle et al. |
| 2018/0056104 | A1 | 3/2018 | Cromie et al. |
| 2018/0056130 | A1 | 3/2018 | Bitran et al. |
| 2018/0060494 | A1 | 3/2018 | Dias et al. |
| 2018/0070864 | A1 | 3/2018 | Schuster |
| 2018/0071565 | A1 | 3/2018 | Gomberg et al. |
| 2018/0071566 | A1 | 3/2018 | Gomberg et al. |
| 2018/0071569 | A1 | 3/2018 | Gomberg et al. |
| 2018/0071570 | A1 | 3/2018 | Gomberg et al. |
| 2018/0071571 | A1 | 3/2018 | Gomberg et al. |
| 2018/0071572 | A1 | 3/2018 | Gomberg et al. |
| 2018/0071583 | A1* | 3/2018 | Paiz ................... A63B 24/0075 |
| 2018/0075205 | A1 | 3/2018 | Moturu et al. |
| 2018/0078149 | A1 | 3/2018 | Fonte et al. |
| 2018/0078182 | A1 | 3/2018 | Chen |
| 2018/0078843 | A1 | 3/2018 | Tran et al. |
| 2018/0085615 | A1 | 3/2018 | Astolfi et al. |
| 2018/0085630 | A1* | 3/2018 | Capell .................... G16H 20/30 |
| 2018/0089385 | A1 | 3/2018 | Gupta |
| 2018/0096111 | A1 | 4/2018 | Wells et al. |
| 2018/0099178 | A1 | 4/2018 | Schaefer et al. |
| 2018/0102190 | A1 | 4/2018 | Hogue et al. |
| 2018/0103859 | A1 | 4/2018 | Provenzano |
| 2018/0108430 | A1 | 4/2018 | Vo |
| 2018/0113985 | A1 | 4/2018 | Gandy et al. |
| 2018/0116741 | A1 | 5/2018 | Garcia Kilroy et al. |
| 2018/0117417 | A1 | 5/2018 | Davis |
| 2018/0130555 | A1 | 5/2018 | Chronis et al. |
| 2018/0133551 | A1 | 5/2018 | Chang |
| 2018/0140927 | A1 | 5/2018 | Kito |
| 2018/0169476 | A1 | 6/2018 | Shimada |
| 2018/0177612 | A1 | 6/2018 | Trabish et al. |
| 2018/0178061 | A1 | 6/2018 | O'Larte et al. |
| 2018/0199855 | A1 | 7/2018 | Odame et al. |
| 2018/0200577 | A1 | 7/2018 | Dugan |
| 2018/0214729 | A1* | 8/2018 | Rubin ................ A63B 24/0087 |
| 2018/0220935 | A1 | 8/2018 | Tadano et al. |
| 2018/0228682 | A1 | 8/2018 | Bayerlein et al. |
| 2018/0232492 | A1 | 8/2018 | Al-Alul et al. |
| 2018/0236307 | A1 | 8/2018 | Hyde et al. |
| 2018/0240552 | A1 | 8/2018 | Tuyl et al. |
| 2018/0250075 | A1 | 9/2018 | Cho |
| 2018/0253991 | A1 | 9/2018 | Tang et al. |
| 2018/0255110 | A1 | 9/2018 | Dowlatkhah et al. |
| 2018/0256079 | A1 | 9/2018 | Yang et al. |
| 2018/0256939 | A1 | 9/2018 | Malcolm |
| 2018/0263530 | A1 | 9/2018 | Jung |
| 2018/0263535 | A1 | 9/2018 | Cramer |
| 2018/0263552 | A1 | 9/2018 | Graman et al. |
| 2018/0264312 | A1 | 9/2018 | Pompile et al. |
| 2018/0271432 | A1 | 9/2018 | Auchinleck et al. |
| 2018/0272184 | A1 | 9/2018 | Vassilaros et al. |
| 2018/0272190 | A1 | 9/2018 | Miura |
| 2018/0280784 | A1 | 10/2018 | Romeo et al. |
| 2018/0285463 | A1 | 10/2018 | Choi et al. |
| 2018/0290017 | A1 | 10/2018 | Fung |
| 2018/0296143 | A1 | 10/2018 | Anderson et al. |
| 2018/0296157 | A1 | 10/2018 | Bleich et al. |
| 2018/0318122 | A1 | 11/2018 | LeCursi et al. |
| 2018/0326243 | A1 | 11/2018 | Badi et al. |
| 2018/0330058 | A1 | 11/2018 | Bates |
| 2018/0330810 | A1 | 11/2018 | Gamarnik |
| 2018/0330824 | A1 | 11/2018 | Athey et al. |
| 2018/0348759 | A1 | 12/2018 | Freeman |
| 2018/0353812 | A1 | 12/2018 | Lannon et al. |
| 2018/0358119 | A1 | 12/2018 | Bhushan |
| 2018/0360340 | A1 | 12/2018 | Rehse et al. |
| 2018/0361203 | A1 | 12/2018 | Wang |
| 2018/0366225 | A1 | 12/2018 | Mansi et al. |
| 2018/0373844 | A1 | 12/2018 | Ferrandez-Escamez et al. |
| 2019/0005195 | A1 | 1/2019 | Peterson |
| 2019/0009135 | A1 | 1/2019 | Wu |
| 2019/0009136 | A1 | 1/2019 | Lee |
| 2019/0019163 | A1 | 1/2019 | Batey et al. |
| 2019/0019573 | A1 | 1/2019 | Lake et al. |
| 2019/0019578 | A1 | 1/2019 | Vaccaro |
| 2019/0025995 | A1 | 1/2019 | Williams |
| 2019/0030415 | A1 | 1/2019 | Volpe, Jr. |
| 2019/0031284 | A1 | 1/2019 | Fuchs |
| 2019/0046794 | A1 | 2/2019 | Goodall et al. |
| 2019/0060708 | A1 | 2/2019 | Fung |
| 2019/0065970 | A1 | 2/2019 | Bonutti et al. |
| 2019/0066832 | A1 | 2/2019 | Kang et al. |
| 2019/0076701 | A1 | 3/2019 | Dugan |
| 2019/0080802 | A1 | 3/2019 | Ziobro et al. |
| 2019/0083846 | A1 | 3/2019 | Eder |
| 2019/0088356 | A1 | 3/2019 | Oliver et al. |
| 2019/0090744 | A1 | 3/2019 | Mahfouz |
| 2019/0096534 | A1 | 3/2019 | Joao |
| 2019/0105551 | A1 | 4/2019 | Ray |
| 2019/0108912 | A1 | 4/2019 | Spurlock, III |
| 2019/0111299 | A1 | 4/2019 | Radcliffe et al. |
| 2019/0115097 | A1 | 4/2019 | Macoviak et al. |
| 2019/0117156 | A1 | 4/2019 | Howard et al. |
| 2019/0118038 | A1 | 4/2019 | Tana et al. |
| 2019/0118066 | A1 | 4/2019 | Cardona |
| 2019/0122770 | A1 | 4/2019 | Pengetnze |
| 2019/0126099 | A1 | 5/2019 | Hoang |
| 2019/0132948 | A1 | 5/2019 | Longinotti-Buitoni et al. |
| 2019/0134308 | A1 | 5/2019 | Newberry |
| 2019/0134454 | A1 | 5/2019 | Mahoney et al. |
| 2019/0137988 | A1 | 5/2019 | Cella et al. |
| 2019/0143191 | A1 | 5/2019 | Ran et al. |
| 2019/0143193 | A1 | 5/2019 | Kim |
| 2019/0145774 | A1 | 5/2019 | Ellis |
| 2019/0146740 | A1 | 5/2019 | Yuen |
| 2019/0163876 | A1 | 5/2019 | Remme et al. |
| 2019/0167988 | A1 | 6/2019 | Shahriari et al. |
| 2019/0172587 | A1 | 6/2019 | Park et al. |
| 2019/0175988 | A1 | 6/2019 | Volterrani et al. |
| 2019/0183715 | A1 | 6/2019 | Kapure et al. |
| 2019/0192880 | A1 | 6/2019 | Hibbard |
| 2019/0200920 | A1 | 7/2019 | Tien et al. |
| 2019/0209022 | A1 | 7/2019 | Sobol |
| 2019/0209891 | A1 | 7/2019 | Fung |
| 2019/0214119 | A1 | 7/2019 | Wachira et al. |
| 2019/0223797 | A1 | 7/2019 | Tran |
| 2019/0224528 | A1 | 7/2019 | Omid-Zohoor et al. |
| 2019/0228856 | A1 | 7/2019 | Leifer |
| 2019/0232108 | A1 | 8/2019 | Kovach et al. |
| 2019/0240103 | A1 | 8/2019 | Hepler et al. |
| 2019/0240541 | A1 | 8/2019 | Denton et al. |
| 2019/0244540 | A1 | 8/2019 | Errante et al. |

(56) References Cited

U.S. PATENT DOCUMENTS

2019/0247718 A1 8/2019 Blevins
2019/0251723 A1 8/2019 Coppersmith
2019/0261959 A1 8/2019 Frankel
2019/0269343 A1 9/2019 Ramos Murguialday et al.
2019/0274523 A1 9/2019 Bates et al.
2019/0275368 A1 9/2019 Maroldi
2019/0283247 A1 9/2019 Chang
2019/0290191 A1 9/2019 Leppäluoto et al.
2019/0304584 A1 10/2019 Savolainen
2019/0307983 A1 10/2019 Goldman
2019/0314681 A1 10/2019 Yang
2019/0344123 A1* 11/2019 Rubin .................. A63B 21/153
2019/0354632 A1 11/2019 Mital et al.
2019/0362242 A1 11/2019 Pillai et al.
2019/0366146 A1 12/2019 Tong et al.
2019/0371472 A1 12/2019 Blanchard
2019/0385199 A1 12/2019 Bender et al.
2019/0388728 A1 12/2019 Wang et al.
2019/0392936 A1 12/2019 Arric et al.
2019/0392939 A1 12/2019 Basta et al.
2020/0005928 A1 1/2020 Daniel
2020/0015736 A1 1/2020 Alhathal
2020/0034665 A1 1/2020 Ghanta
2020/0034707 A1 1/2020 Kivatinos et al.
2020/0038703 A1 2/2020 Cleary et al.
2020/0051446 A1 2/2020 Rubinstein et al.
2020/0054922 A1 2/2020 Azaria
2020/0066390 A1 2/2020 Svendrys et al.
2020/0085300 A1 3/2020 Kwatra et al.
2020/0090802 A1 3/2020 Maron
2020/0093418 A1 3/2020 Kluger et al.
2020/0098463 A1 3/2020 Arunachalam et al.
2020/0121987 A1 4/2020 Loh
2020/0129237 A1 4/2020 Erdem
2020/0129808 A1 4/2020 Fomin
2020/0139194 A1 5/2020 Min
2020/0143922 A1 5/2020 Chekroud et al.
2020/0151595 A1 5/2020 Jayalath et al.
2020/0151646 A1 5/2020 De La Fuente Sanchez
2020/0152339 A1 5/2020 Pulitzer et al.
2020/0160044 A1 5/2020 Sur
2020/0160198 A1 5/2020 Reeves et al.
2020/0170876 A1 6/2020 Kapure et al.
2020/0176098 A1 6/2020 Lucas et al.
2020/0188774 A1 6/2020 Fung
2020/0197744 A1 6/2020 Schweighofer
2020/0221975 A1 7/2020 Basta et al.
2020/0237291 A1 7/2020 Raja
2020/0237452 A1 7/2020 Wolf et al.
2020/0254310 A1 8/2020 Triplett
2020/0261763 A1 8/2020 Park
2020/0267487 A1 8/2020 Siva
2020/0275886 A1 9/2020 Mason
2020/0289045 A1 9/2020 Hacking et al.
2020/0289046 A1 9/2020 Hacking et al.
2020/0289879 A1 9/2020 Hacking et al.
2020/0289880 A1 9/2020 Hacking et al.
2020/0289881 A1 9/2020 Hacking et al.
2020/0289889 A1 9/2020 Hacking et al.
2020/0293712 A1 9/2020 Potts et al.
2020/0303063 A1 9/2020 Sharma et al.
2020/0312447 A1 10/2020 Bohn et al.
2020/0320454 A1 10/2020 Almashor
2020/0334972 A1 10/2020 Gopalakrishnan
2020/0338394 A1 10/2020 Neumann
2020/0346072 A1 11/2020 Shah
2020/0350076 A1 11/2020 Brown
2020/0353314 A1 11/2020 Messinger
2020/0357299 A1 11/2020 Patel et al.
2020/0365256 A1 11/2020 Hayashitani et al.
2020/0376327 A1 12/2020 Bissonnette
2020/0391080 A1 12/2020 Powers
2020/0395112 A1 12/2020 Ronner
2020/0398083 A1 12/2020 Adelsheim
2020/0401224 A1 12/2020 Cotton
2020/0402638 A1 12/2020 Song et al.
2020/0402662 A1 12/2020 Esmailian et al.
2020/0410374 A1 12/2020 White
2020/0410893 A1 12/2020 Ridington
2020/0411162 A1 12/2020 Lien et al.
2020/0411170 A1 12/2020 Brown
2021/0005224 A1 1/2021 Rothschild et al.
2021/0005319 A1 1/2021 Otsuki et al.
2021/0008413 A1 1/2021 Asikainen et al.
2021/0015560 A1 1/2021 Boddington et al.
2021/0027889 A1 1/2021 Neil et al.
2021/0035674 A1 2/2021 Volosin et al.
2021/0050086 A1 2/2021 Rose et al.
2021/0065855 A1 3/2021 Pepin et al.
2021/0074178 A1 3/2021 Ilan et al.
2021/0076981 A1 3/2021 Hacking et al.
2021/0077860 A1 3/2021 Posnack et al.
2021/0077884 A1 3/2021 De Las Casas Zolezzi et al.
2021/0082554 A1 3/2021 Kalia et al.
2021/0093891 A1 4/2021 Sheng
2021/0098099 A1 4/2021 Neumann
2021/0098129 A1 4/2021 Neumann
2021/0101051 A1 4/2021 Posnack et al.
2021/0106899 A1* 4/2021 Willardson ............ A63B 22/06
2021/0113890 A1 4/2021 Posnack et al.
2021/0125696 A1 4/2021 Liu et al.
2021/0127974 A1 5/2021 Mason et al.
2021/0128080 A1 5/2021 Mason et al.
2021/0128255 A1 5/2021 Mason et al.
2021/0128978 A1 5/2021 Gilstrom et al.
2021/0134412 A1 5/2021 Guaneri et al.
2021/0134425 A1 5/2021 Mason et al.
2021/0134427 A1 5/2021 Mason et al.
2021/0134428 A1 5/2021 Mason et al.
2021/0134429 A1 5/2021 Mason
2021/0134430 A1 5/2021 Mason et al.
2021/0134432 A1 5/2021 Mason et al.
2021/0134456 A1 5/2021 Posnack et al.
2021/0134457 A1 5/2021 Mason et al.
2021/0134458 A1 5/2021 Mason et al.
2021/0134463 A1 5/2021 Mason et al.
2021/0138304 A1 5/2021 Mason et al.
2021/0142875 A1 5/2021 Mason et al.
2021/0142893 A1 5/2021 Guaneri et al.
2021/0142898 A1 5/2021 Mason et al.
2021/0142903 A1 5/2021 Mason et al.
2021/0144074 A1 5/2021 Guaneri et al.
2021/0186419 A1 6/2021 Van Ee et al.
2021/0187348 A1 6/2021 Phillips et al.
2021/0202090 A1 7/2021 ODonovan et al.
2021/0202103 A1 7/2021 Bostic et al.
2021/0205660 A1 7/2021 Shavit
2021/0217516 A1 7/2021 Nash
2021/0236020 A1 8/2021 Matijevich et al.
2021/0236903 A1 8/2021 Briel
2021/0240853 A1 8/2021 Carlson
2021/0241137 A1 8/2021 Jain et al.
2021/0244998 A1 8/2021 Hacking et al.
2021/0245003 A1 8/2021 Turner
2021/0251562 A1 8/2021 Jain
2021/0272677 A1 9/2021 Barbee
2021/0275025 A1 9/2021 Hickle
2021/0291010 A1* 9/2021 Miller .................. A61H 1/0237
2021/0343384 A1 11/2021 Purushothaman et al.
2021/0345879 A1 11/2021 Mason et al.
2021/0345975 A1 11/2021 Mason et al.
2021/0350888 A1 11/2021 Guaneri et al.
2021/0350898 A1 11/2021 Mason et al.
2021/0350899 A1 11/2021 Mason et al.
2021/0350901 A1 11/2021 Mason et al.
2021/0350902 A1 11/2021 Mason et al.
2021/0350914 A1 11/2021 Guaneri et al.
2021/0350926 A1 11/2021 Mason et al.
2021/0354002 A1 11/2021 Schaefer
2021/0361514 A1 11/2021 Choi et al.
2021/0366587 A1 11/2021 Mason et al.
2021/0369536 A1 12/2021 Mooney
2021/0375425 A1 12/2021 Zhang
2021/0383008 A1 12/2021 Manasse

(56) References Cited

U.S. PATENT DOCUMENTS

2021/0383909 A1 12/2021 Mason et al.
2021/0387054 A1 12/2021 Schaefer
2021/0391091 A1 12/2021 Mason
2021/0394011 A1 12/2021 Neuhaus et al.
2021/0398668 A1 12/2021 Chock et al.
2021/0406738 A1 12/2021 O'Donncha et al.
2021/0407670 A1 12/2021 Mason et al.
2021/0407681 A1 12/2021 Mason et al.
2022/0000556 A1 1/2022 Casey et al.
2022/0015838 A1 1/2022 Posnack et al.
2022/0016480 A1 1/2022 Bissonnette et al.
2022/0016482 A1 1/2022 Bissonnette
2022/0016484 A1 1/2022 Bissonnett et al.
2022/0016485 A1 1/2022 Bissonnette
2022/0016486 A1 1/2022 Bissonnette et al.
2022/0020469 A1 1/2022 Tanner
2022/0028511 A1 1/2022 Neumann
2022/0044806 A1 2/2022 Sanders et al.
2022/0047921 A1 2/2022 Bissonnette et al.
2022/0066548 A1 3/2022 Helot
2022/0079690 A1 3/2022 Mason et al.
2022/0080256 A1 3/2022 Arn et al.
2022/0096006 A1 3/2022 Wu et al.
2022/0105384 A1 4/2022 Hacking et al.
2022/0105385 A1 4/2022 Hacking et al.
2022/0105390 A1 4/2022 Yuasa
2022/0115133 A1 4/2022 Mason et al.
2022/0117514 A1 4/2022 Kuhn et al.
2022/0118218 A1 4/2022 Bense et al.
2022/0122724 A1 4/2022 Durlach et al.
2022/0126169 A1 4/2022 Mason
2022/0133576 A1 5/2022 Choi et al.
2022/0148725 A1 5/2022 Mason et al.
2022/0158916 A1 5/2022 Mason et al.
2022/0165398 A1 5/2022 Avila-Hernandez et al.
2022/0176039 A1 6/2022 Lintereur et al.
2022/0181004 A1 6/2022 Zilca et al.
2022/0193491 A1 6/2022 Mason
2022/0230729 A1 7/2022 Mason et al.
2022/0238222 A1 7/2022 Neuberg
2022/0238223 A1 7/2022 Mason
2022/0258935 A1 8/2022 Kraft
2022/0262483 A1 8/2022 Rosenberg et al.
2022/0262504 A1 8/2022 Bratty et al.
2022/0266094 A1 8/2022 Mason et al.
2022/0270738 A1 8/2022 Mason et al.
2022/0273985 A1 9/2022 Jeong et al.
2022/0273986 A1 9/2022 Mason
2022/0288460 A1 9/2022 Mason
2022/0288461 A1 9/2022 Ashley et al.
2022/0288462 A1 9/2022 Ashley et al.
2022/0293257 A1 9/2022 Guaneri et al.
2022/0300787 A1 9/2022 Wall et al.
2022/0304881 A1 9/2022 Choi et al.
2022/0304882 A1 9/2022 Choi
2022/0305291 A1 9/2022 Hibbard
2022/0305328 A1 9/2022 Choi et al.
2022/0314072 A1 10/2022 Bissonnette et al.
2022/0314074 A1 10/2022 Bissonnette
2022/0314075 A1 10/2022 Mason et al.
2022/0323826 A1 10/2022 Khurana
2022/0327714 A1 10/2022 Cook et al.
2022/0327807 A1 10/2022 Cook et al.
2022/0328181 A1 10/2022 Mason et al.
2022/0330823 A1 10/2022 Janssen
2022/0331663 A1 10/2022 Mason
2022/0336077 A1 10/2022 Chen et al.
2022/0338761 A1 10/2022 Maddahi et al.
2022/0339052 A1 10/2022 Kim
2022/0339501 A1 10/2022 Mason et al.
2022/0342969 A1 10/2022 Watterson et al.
2022/0346703 A1 11/2022 Abdo et al.
2022/0370851 A1 11/2022 Guidarelli et al.
2022/0384010 A1 12/2022 Kanayama
2022/0384012 A1 12/2022 Mason
2022/0392591 A1 12/2022 Guaneri et al.
2022/0395232 A1 12/2022 Locke
2022/0401783 A1 12/2022 Choi
2022/0415469 A1 12/2022 Mason
2022/0415471 A1 12/2022 Mason
2023/0001268 A1 1/2023 Bissonnette et al.
2023/0013530 A1 1/2023 Mason
2023/0014598 A1 1/2023 Mason et al.
2023/0022981 A1 1/2023 Bhushan
2023/0029639 A1 2/2023 Roy
2023/0047253 A1 2/2023 Gnanasambandam et al.
2023/0048040 A1 2/2023 Hacking et al.
2023/0051751 A1 2/2023 Hacking et al.
2023/0055078 A1 2/2023 Malcolm
2023/0058605 A1 2/2023 Mason
2023/0060039 A1 2/2023 Mason
2023/0072368 A1 3/2023 Mason
2023/0078793 A1 3/2023 Mason
2023/0119461 A1 4/2023 Mason
2023/0190100 A1 6/2023 Stump
2023/0197240 A1 6/2023 Rosenberg
2023/0201656 A1 6/2023 Hacking et al.
2023/0207097 A1 6/2023 Mason
2023/0207124 A1 6/2023 Walsh et al.
2023/0215539 A1 7/2023 Rosenberg et al.
2023/0215552 A1 7/2023 Khotilovich et al.
2023/0218950 A1 7/2023 Belson
2023/0245747 A1 8/2023 Rosenberg et al.
2023/0245748 A1 8/2023 Rosenberg et al.
2023/0245750 A1 8/2023 Rosenberg et al.
2023/0245751 A1 8/2023 Rosenberg et al.
2023/0249599 A1 8/2023 Nicola
2023/0253089 A1 8/2023 Rosenberg et al.
2023/0255555 A1 8/2023 Sundaram et al.
2023/0263428 A1 8/2023 Hull et al.
2023/0274813 A1 8/2023 Rosenberg et al.
2023/0282329 A1 9/2023 Mason et al.
2023/0298718 A1 9/2023 Robinson
2023/0356025 A1 11/2023 Rosenberg
2023/0364471 A1 11/2023 Choi et al.
2023/0364472 A1 11/2023 Posnack
2023/0368886 A1 11/2023 Rosenberg
2023/0377710 A1 11/2023 Chen et al.
2023/0377711 A1 11/2023 Rosenberg
2023/0377712 A1 11/2023 Rosenberg
2023/0386639 A1 11/2023 Rosenberg
2023/0390627 A1 12/2023 Bolton
2023/0395231 A1 12/2023 Rosenberg
2023/0395232 A1 12/2023 Rosenberg
2024/0024731 A1 1/2024 Rosenberg
2024/0058651 A1 2/2024 Bissonnette
2024/0127924 A1 4/2024 Rosenberg
2024/0136041 A1 4/2024 Rosenberg
2024/0177846 A1 5/2024 Gnanasambandam
2024/0203580 A1 6/2024 Mason
2024/0339192 A1 10/2024 Rosenberg

FOREIGN PATENT DOCUMENTS

CN 101964151 A 2/2011
CN 201889024 U 7/2011
CN 202220794 U 5/2012
CN 102670381 A 9/2012
CN 103263336 A 8/2013
CN 103390357 A 11/2013
CN 103473631 A 12/2013
CN 103488880 A 1/2014
CN 103501328 A 1/2014
CN 103721343 A 4/2014
CN 203677851 U 7/2014
CN 104335211 A 2/2015
CN 105263448 A 1/2016
CN 105620643 A 6/2016
CN 105683977 A 6/2016
CN 103136447 B 8/2016
CN 105894088 A 8/2016
CN 105930668 A 9/2016
CN 205626871 U 10/2016
CN 106127646 A 11/2016

(56) References Cited

FOREIGN PATENT DOCUMENTS

| | | | |
|---|---|---|---|
| CN | 106236502 | A | 12/2016 |
| CN | 106510985 | A | 3/2017 |
| CN | 106621195 | A | 5/2017 |
| CN | 106845077 | A | 6/2017 |
| CN | 107025373 | A | 8/2017 |
| CN | 107066819 | A | 8/2017 |
| CN | 107430641 | A | 12/2017 |
| CN | 107551475 | A | 1/2018 |
| CN | 107736982 | A | 2/2018 |
| CN | 107930021 | A | 4/2018 |
| CN | 108078737 | A | 5/2018 |
| CN | 207429102 | U | 6/2018 |
| CN | 208224811 | A | 12/2018 |
| CN | 109191954 | A | 1/2019 |
| CN | 109248432 | A | 1/2019 |
| CN | 109308940 | A | 2/2019 |
| CN | 109363887 | A | 2/2019 |
| CN | 109431742 | A | 3/2019 |
| CN | 208573971 | U | 3/2019 |
| CN | 110148472 | A | 8/2019 |
| CN | 110201358 | A | 9/2019 |
| CN | 110215188 | A | 9/2019 |
| CN | 110322957 | A | 10/2019 |
| CN | 110613585 | A | 12/2019 |
| CN | 110721438 | A | 1/2020 |
| CN | 110808092 | A | 2/2020 |
| CN | 110931103 | A | 3/2020 |
| CN | 110993057 | A | 4/2020 |
| CN | 210384372 | U | 4/2020 |
| CN | 111084618 | A | 5/2020 |
| CN | 111105859 | A | 5/2020 |
| CN | 111111110 | A | 5/2020 |
| CN | 111199787 | A | 5/2020 |
| CN | 210447971 | U | 5/2020 |
| CN | 111329674 | A | 6/2020 |
| CN | 111370088 | A | 7/2020 |
| CN | 111460305 | A | 7/2020 |
| CN | 111544834 | A | 8/2020 |
| CN | 111714832 | A | 9/2020 |
| CN | 111790111 | A | 10/2020 |
| CN | 211635070 | U | 10/2020 |
| CN | 211798556 | U | 10/2020 |
| CN | 111973956 | A | 11/2020 |
| CN | 212067582 | U | 12/2020 |
| CN | 212141371 | U | 12/2020 |
| CN | 112190440 | A | 1/2021 |
| CN | 112289425 | A | 1/2021 |
| CN | 212522890 | U | 2/2021 |
| CN | 212624809 | U | 2/2021 |
| CN | 212730865 | U | 3/2021 |
| CN | 112603295 | A | 4/2021 |
| CN | 213049207 | U | 4/2021 |
| CN | 213077324 | U | 4/2021 |
| CN | 213190965 | U | 5/2021 |
| CN | 213220742 | U | 5/2021 |
| CN | 213823322 | U | 7/2021 |
| CN | 213851851 | U | 8/2021 |
| CN | 213994716 | U | 8/2021 |
| CN | 113384850 | A | 9/2021 |
| CN | 113421642 | A | 9/2021 |
| CN | 214232565 | U | 9/2021 |
| CN | 113499572 | A | 10/2021 |
| CN | 113521655 | A | 10/2021 |
| CN | 214388673 | U | 10/2021 |
| CN | 214763119 | U | 11/2021 |
| CN | 214806540 | U | 11/2021 |
| CN | 214913108 | U | 11/2021 |
| CN | 215025723 | U | 12/2021 |
| CN | 215084603 | U | 12/2021 |
| CN | 215136488 | U | 12/2021 |
| CN | 113885361 | A | 1/2022 |
| CN | 114049961 | A | 2/2022 |
| CN | 114203274 | A | 3/2022 |
| CN | 216258145 | U | 4/2022 |
| CN | 216366476 | U | 4/2022 |
| CN | 216497237 | U | 5/2022 |
| CN | 114632302 | A | 6/2022 |
| CN | 114694824 | A | 7/2022 |
| CN | 114898832 | A | 8/2022 |
| CN | 217246501 | U | 8/2022 |
| CN | 114983760 | A | 9/2022 |
| CN | 114983761 | A | 9/2022 |
| CN | 115006789 | A | 9/2022 |
| CN | 115089917 | A | 9/2022 |
| CN | 217472652 | U | 9/2022 |
| CN | 110270062 | B | 10/2022 |
| CN | 217612764 | U | 10/2022 |
| CN | 115337599 | A | 11/2022 |
| CN | 115382062 | A | 11/2022 |
| CN | 115487042 | A | 12/2022 |
| CN | 218187703 | U | 1/2023 |
| CN | 218187717 | U | 1/2023 |
| CN | 218420859 | U | 2/2023 |
| CN | 115954081 | A | 4/2023 |
| DE | 95019 | C | 1/1897 |
| DE | 7628633 | U1 | 12/1977 |
| DE | 8519150 | U1 | 10/1985 |
| DE | 3732905 | A1 | 7/1988 |
| DE | 19619820 | A1 | 12/1996 |
| DE | 29620008 | U1 | 2/1997 |
| DE | 19947926 | A1 | 4/2001 |
| DE | 102007025664 | A1 | 12/2008 |
| DE | 102018202497 | A1 | 8/2018 |
| DE | 102018211212 | A1 | 1/2019 |
| DE | 102019108425 | B3 | 8/2020 |
| EP | 199600 | A2 | 10/1986 |
| EP | 0383137 | A2 | 8/1990 |
| EP | 634319 | A2 | 1/1995 |
| EP | 0919259 | A1 | 6/1999 |
| EP | 1034817 | A1 | 9/2000 |
| EP | 1159989 | A1 | 12/2001 |
| EP | 1391179 | A1 | 2/2004 |
| EP | 1968028 | | 9/2008 |
| EP | 2564904 | A1 | 3/2013 |
| EP | 2575064 | A1 | 4/2013 |
| EP | 1909730 | B1 | 4/2014 |
| EP | 2815242 | A4 | 12/2014 |
| EP | 2869805 | A | 5/2015 |
| EP | 2997951 | A1 | 3/2016 |
| EP | 2688472 | B1 | 4/2016 |
| EP | 3264303 | A1 | 1/2018 |
| EP | 3323473 | A1 | 5/2018 |
| EP | 3547322 | A1 | 10/2019 |
| EP | 3627514 | A1 | 3/2020 |
| EP | 3671700 | A1 | 6/2020 |
| EP | 3688537 | A1 | 8/2020 |
| EP | 3731733 | A1 | 11/2020 |
| EP | 3984508 | A1 | 4/2022 |
| EP | 3984509 | A1 | 4/2022 |
| EP | 3984510 | A1 | 4/2022 |
| EP | 3984511 | A1 | 4/2022 |
| EP | 3984512 | A1 | 4/2022 |
| EP | 3984513 | A1 | 4/2022 |
| EP | 4054699 | A1 | 9/2022 |
| EP | 4112033 | A1 | 1/2023 |
| FR | 2527541 | A2 | 12/1983 |
| FR | 3127393 | A1 | 3/2023 |
| GB | 141664 | A | 11/1920 |
| GB | 2336140 | A | 10/1999 |
| GB | 2372459 | A | 8/2002 |
| GB | 2512431 | A | 10/2014 |
| GB | 2591542 | B | 3/2022 |
| IN | 23/2009 | | 5/2009 |
| IN | 201811043670 | A | 7/2018 |
| JP | 2000005339 | A | 1/2000 |
| JP | 2003225875 | A | 8/2003 |
| JP | 2005227928 | A | 8/2005 |
| JP | 2005227928 | A1 | 8/2005 |
| JP | 2009112336 | A | 5/2009 |
| JP | 2013515995 | A | 5/2013 |
| JP | 2014104139 | A | 6/2014 |
| JP | 3193662 | U | 10/2014 |
| JP | 3198173 | U | 6/2015 |
| JP | 5804063 | B2 | 11/2015 |

(56) References Cited

FOREIGN PATENT DOCUMENTS

| | | | |
|---|---|---|---|
| JP | 6454071 | B2 | 1/2019 |
| JP | 2019028647 | A | 2/2019 |
| JP | 2019134909 | A | 8/2019 |
| JP | 6573739 | B1 | 9/2019 |
| JP | 6659831 | B2 | 3/2020 |
| JP | 2020057082 | A | 4/2020 |
| JP | 6710357 | B1 | 6/2020 |
| JP | 6775757 | B1 | 10/2020 |
| JP | 2021027917 | A | 2/2021 |
| JP | 2021040882 | A | 3/2021 |
| JP | 6871379 | B2 | 5/2021 |
| JP | 2022521378 | A | 4/2022 |
| JP | 3238491 | U | 7/2022 |
| JP | 7198364 | B2 | 12/2022 |
| JP | 7202474 | B2 | 1/2023 |
| JP | 7231750 | B2 | 3/2023 |
| JP | 7231751 | B2 | 3/2023 |
| JP | 7231752 | B2 | 3/2023 |
| KR | 20020009724 | A | 2/2002 |
| KR | 200276919 | Y1 | 5/2002 |
| KR | 20020065253 | A | 8/2002 |
| KR | 20040082259 | A | 9/2004 |
| KR | 100582596 | B1 | 5/2006 |
| KR | 101042258 | B1 | 6/2011 |
| KR | 101258250 | B1 | 4/2013 |
| KR | 101325581 | B1 | 11/2013 |
| KR | 20140128630 | A | 11/2014 |
| KR | 20150017693 | A | 2/2015 |
| KR | 20150078191 | A | 7/2015 |
| KR | 101580071 | B1 | 12/2015 |
| KR | 101647620 | B1 | 8/2016 |
| KR | 20160093990 | A | 8/2016 |
| KR | 20170038837 | A | 4/2017 |
| KR | 20170086922 | A | 7/2017 |
| KR | 20180004928 | A | 1/2018 |
| KR | 20190016727 | A | 2/2019 |
| KR | 20190029175 | A | 3/2019 |
| KR | 20190056116 | A | 5/2019 |
| KR | 101988167 | B1 | 6/2019 |
| KR | 101969392 | B1 | 8/2019 |
| KR | 102038055 | B1 | 10/2019 |
| KR | 102043239 | B1 | 11/2019 |
| KR | 102055279 | B1 | 12/2019 |
| KR | 20200019548 | A | 2/2020 |
| KR | 102088333 | B1 | 3/2020 |
| KR | 20200025290 | A | 3/2020 |
| KR | 20200029180 | A | 3/2020 |
| KR | 102097190 | B1 | 4/2020 |
| KR | 102116664 | B1 | 5/2020 |
| KR | 102116968 | B1 | 5/2020 |
| KR | 20200056233 | A | 5/2020 |
| KR | 102120828 | B1 | 6/2020 |
| KR | 102121586 | B1 | 6/2020 |
| KR | 102142713 | B1 | 8/2020 |
| KR | 102162522 | B1 | 10/2020 |
| KR | 20200119665 | A | 10/2020 |
| KR | 102173553 | B1 | 11/2020 |
| KR | 102180079 | B1 | 11/2020 |
| KR | 102188766 | B1 | 12/2020 |
| KR | 102196793 | B1 | 12/2020 |
| KR | 20210006212 | A | 1/2021 |
| KR | 102224188 | B1 | 3/2021 |
| KR | 102224618 | B1 | 3/2021 |
| KR | 102246049 | B1 | 4/2021 |
| KR | 102246050 | B1 | 4/2021 |
| KR | 102246051 | B1 | 4/2021 |
| KR | 102246052 | B1 | 4/2021 |
| KR | 20210052028 | A | 5/2021 |
| KR | 102264498 | B1 | 6/2021 |
| KR | 102352602 | B1 | 1/2022 |
| KR | 102352603 | B1 | 1/2022 |
| KR | 102352604 | B1 | 1/2022 |
| KR | 20220004639 | A | 1/2022 |
| KR | 102387577 | B1 | 4/2022 |
| KR | 102421437 | B1 | 7/2022 |
| KR | 20220102207 | A | 7/2022 |
| KR | 102427545 | B1 | 8/2022 |
| KR | 102467495 | B1 | 11/2022 |
| KR | 102467496 | B1 | 11/2022 |
| KR | 102469723 | B1 | 11/2022 |
| KR | 102471990 | B1 | 11/2022 |
| KR | 20220145989 | A | 11/2022 |
| KR | 20220156134 | A | 11/2022 |
| KR | 102502744 | B1 | 2/2023 |
| KR | 20230019349 | A | 2/2023 |
| KR | 20230019350 | A | 2/2023 |
| KR | 20230026556 | A | 2/2023 |
| KR | 20230026668 | A | 2/2023 |
| KR | 20230040526 | | 3/2023 |
| KR | 20230050506 | A | 4/2023 |
| KR | 20230056118 | A | 4/2023 |
| KR | 102528503 | B1 | 5/2023 |
| KR | 102531930 | B1 | 5/2023 |
| KR | 102532766 | B1 | 5/2023 |
| KR | 102539190 | B1 | 6/2023 |
| PL | P.401020 | | 4/2014 |
| RU | 2154460 | C2 | 8/2000 |
| RU | 2014131288 | A | 2/2016 |
| RU | 2738571 | C1 | 12/2020 |
| TW | M474545 | U | 3/2014 |
| TW | I442956 | B | 7/2014 |
| TW | M638437 | U | 3/2023 |
| WO | 1998009687 | A1 | 3/1998 |
| WO | 9912468 | | 3/1999 |
| WO | 0149235 | A2 | 7/2001 |
| WO | 0151083 | A2 | 7/2001 |
| WO | 2001050387 | A1 | 7/2001 |
| WO | 2001056465 | A1 | 8/2001 |
| WO | 02062211 | A2 | 8/2002 |
| WO | 02093312 | A2 | 11/2002 |
| WO | 2003043494 | A1 | 5/2003 |
| WO | 2005018453 | A1 | 3/2005 |
| WO | 2005074369 | A2 | 8/2005 |
| WO | 2006004430 | A2 | 1/2006 |
| WO | 2006012694 | A1 | 2/2006 |
| WO | 2007102709 | A1 | 9/2007 |
| WO | 2008114291 | A1 | 9/2008 |
| WO | 2008140780 | A1 | 11/2008 |
| WO | 2009003170 | A1 | 12/2008 |
| WO | 2009008968 | A1 | 1/2009 |
| WO | 2010009278 | A2 | 1/2010 |
| WO | 2011025322 | A2 | 3/2011 |
| WO | 2012128801 | A1 | 9/2012 |
| WO | 2013002568 | A2 | 1/2013 |
| WO | 2023164292 | A1 | 3/2013 |
| WO | 2013122839 | A1 | 8/2013 |
| WO | 2014011447 | A1 | 1/2014 |
| WO | 2014039567 | A1 | 3/2014 |
| WO | 2014163976 | A1 | 10/2014 |
| WO | 2015026744 | A1 | 2/2015 |
| WO | 2015065298 | A1 | 5/2015 |
| WO | 2015082555 | A1 | 6/2015 |
| WO | 2016151364 | A1 | 9/2016 |
| WO | 2016154318 | A1 | 9/2016 |
| WO | 2017030781 | A1 | 2/2017 |
| WO | 2017166074 | A1 | 5/2017 |
| WO | 2017091691 | A1 | 6/2017 |
| WO | 2017165238 | A1 | 9/2017 |
| WO | 2018027080 | A1 | 2/2018 |
| WO | 2018081795 | A1 | 5/2018 |
| WO | 2018171853 | A1 | 9/2018 |
| WO | 2019022706 | A1 | 1/2019 |
| WO | 2019106003 | A1 | 6/2019 |
| WO | 2019143940 | A1 | 7/2019 |
| WO | 2020014710 | A2 | 1/2020 |
| WO | 2020075190 | A1 | 4/2020 |
| WO | 2020130979 | A1 | 6/2020 |
| WO | 2020149815 | A2 | 7/2020 |
| WO | 2020158904 | A1 | 8/2020 |
| WO | 2020229705 | A1 | 11/2020 |
| WO | 2020245727 | A1 | 12/2020 |
| WO | 2020249855 | A1 | 12/2020 |
| WO | 2020252599 | A1 | 12/2020 |
| WO | 2020256577 | A1 | 12/2020 |

(56) References Cited

FOREIGN PATENT DOCUMENTS

| | | | |
|---|---|---|---|
| WO | 2021021447 | A1 | 2/2021 |
| WO | 2021022003 | A1 | 2/2021 |
| WO | 2021038980 | A1 | 3/2021 |
| WO | 2021055427 | A1 | 3/2021 |
| WO | 2021061061 | A1 | 4/2021 |
| WO | 2021090267 | A1 | 5/2021 |
| WO | 2021138620 | A1 | 7/2021 |
| WO | 2021216881 | A1 | 10/2021 |
| WO | 2021236961 | A1 | 11/2021 |
| WO | 2022047006 | A1 | 3/2022 |
| WO | 2022092493 | A1 | 5/2022 |
| WO | 2022092494 | A1 | 5/2022 |
| WO | 2022212883 | A1 | 10/2022 |
| WO | 2022212921 | A1 | 10/2022 |
| WO | 2022216498 | A1 | 10/2022 |
| WO | 2022251420 | A1 | 12/2022 |
| WO | 2023008680 | A1 | 2/2023 |
| WO | 2023008681 | A1 | 2/2023 |
| WO | 2023022319 | A1 | 2/2023 |
| WO | 2023022320 | A1 | 2/2023 |
| WO | 2023052695 | A1 | 4/2023 |
| WO | 2023091496 | A1 | 5/2023 |
| WO | 2023215155 | A1 | 11/2023 |
| WO | 2023230075 | A1 | 11/2023 |
| WO | 2024013267 | A1 | 1/2024 |
| WO | 2024107807 | A1 | 5/2024 |

OTHER PUBLICATIONS

Chu Hin Yee, "Physical Activity, Sedentary Behaviour and Health: From Measurements to Recommendations, " 2018, 255 pages.

HCL Fitness, HCI Fitness PhysioTrainer Pro, 2017, retrieved on Aug. 19, 2021, 7 pages, https://www.amazon.com/HCI-Fitness-Physio Trainer-Electronically-Controlled/dp/B0759YMW78/.

International Searching Authority, International Preliminary Report on Patentability of International Application No. PCT/US2017/50895, Date of Mailing Dec. 11, 2018, 52 pages.

International Searching Authority, Search Report and Written Opinion for International Application No. PCT/US2017/50895, Date of Mailing Jan. 12, 2018, 6 pages.

International Searching Authority, Search Report and Written Opinion for International Application No. PCT/US2020/021876, Date of Mailing May 28, 2020, 8 pages.

International Searching Authority, Search Report and Written Opinion for International Application No. PCT/US2020/051008, Date of Mailing Dec. 10, 2020, 9 pages.

International Searching Authority, Search Report and Written Opinion for International Application No. PCT/US2020/056661, Date of Mailing Feb. 12, 2021, 12 pages.

International Searching Authority, Search Report and Written Opinion for International Application No. PCT/US2021/032807, Date of Mailing Sep. 6, 2021, 11 pages.

Matrix, R3xm Recumbent Cycle, retrieved on Aug. 4, 2020, 7 pages, https://www.matrixfitness.com/en/cardio/cycles/r3xm-recumbent.

ROM3 Rehab, ROM3 Rehab System, Apr. 20, 2015, retrieved on Aug. 31, 2018, 12 pages, https://vimeo.com/125438463.

Marios et al., "The effect of tele-monitoring on exercise training adherence, functional capacity, quality of life and glycemic control in patients with type II diabetes," Journal of Sports Science and Medicine, Mar. 2012, vol. 11, 6 pages.

"Abidi, Samina; A Knowledge-Modeling Approach to Integrate Multiple Clinical Practice Guidelines to Provide Evidence-Based Clinical Decision Support for Managing Comorbid Conditions; Journal of Medical Systems 41.12:1-19. Springer Nature B.V. (Dec. 2017) (Year: 2017)".

Fuller, Carole G.; Diagnosis and treatment considerations with comorbid developmentally disabled populations; Journal of Clinical Psychology 54.1: 1-10. John VWey and Sons Inc. (Jan. 1998) (Year: 1998).

He, Jianxing et al. The practical implementation of artificial intelligence technologies in medicine. Nature Medicine; New York vol. 25, Iss. 1. Jan. 2019. (Year: 2019).

cG. Acampora, D. J. Cook, P. Rashidi and A. V. Vasilakos, "A Survey on Ambient Intelligence in Healthcare," in Proceedings of the IEEE, vol. 101, No. 12, pp. 2470-2494, Dec. 2013, doi: 10.1109/JPROC20132262913. (Year: 2013).

H. Demirkan, "A Smart Healthcare Systems Framework," in IT Professional, vol. 15, No. 5, pp. 38-45, Sep.-Oct. 2013, doi: 10.1109/MITP.2013.35. (Year: 2013).

W. Rashwan, J. Fowler and A. Arisha, "A Multi-Method Scheduling Framework for Medical Staff," 2018 Winter Simulation Conference (WSC), Gothenburg, Sweden, 2018, pp. 1464-1475, doi: 10.1109/WSC.2018.8632247. (Year: 2018).

International Search Report and Written Opinion for PCT/US2023/014137, dated Jun. 9, 2023, 13 pages.

Website for "Esino 2022 Physical Therapy Equipments Arm Fitness Indoor Trainer Leg Spin Cycle Machine Exercise Bike for Elderly," https://www.made-in-china.com/showroom/esinogroup/product-detailYdZtwGhCMKVR/China-Esino-2022-Physical-Therapy-Equipments-Arm-Fitness-Indoor-Trainer-Leg-Spin-Cycle-Machine-Exercise-Bike-for-Elderly.html, retrieved on Aug. 29, 2023, 5 pages.

Abedtash, "An Interoperable Electronic Medical Record-Based Platform For Personalized Predictive Analytics", ProQuest LLC, Jul. 2017, 185 pages.

Alcaraz et al., "Machine Learning as Digital Therapy Assessment for Mobile Gait Rehabilitation," 2018 IEEE 28th International Workshop on Machine Learning for Signal Processing (MLSP), Aalborg, Denmark, 2018, 6 pages.

Androutsou et al., "A Smartphone Application Designed to Engage the Elderly in Home-Based Rehabilitation," Frontiers in Digital Health, Sep. 2020, vol. 2, Article 15, 13 pages.

Silva et al., "SapoFitness: A mobile health application for dietary evaluation," 2011 IEEE 13th International Conference on U e-Health Networking, Applications and Services, Columbia, MO, USA, 2011, 6 pages.

Wang et al., "Interactive wearable systems for upper body rehabilitation: a systematic review," Journal of NeuroEngineering and Rehabilitation, 2017, 21 pages.

Marzolini et al., "Eligibility, Enrollment, and Completion of Exercise-Based Cardiac Rehabilitation Following Stroke Rehabilitation: What Are the Barriers?," Physical Therapy, vol. 100, No. 1, 2019, 13 pages.

Nijjar et al., "Randomized Trial of Mindfulness-Based Stress Reduction in Cardiac Patients Eligible for Cardiac Rehabilitation," Scientific Reports, 2019, 12 pages.

Lara et al., "Human-Robot Sensor Interface for Cardiac Rehabilitation," IEEE International Conference on Rehabilitation Robotics, Jul. 2017, 8 pages.

Ishraque et al., "Artificial Intelligence-Based Rehabilitation Therapy Exercise Recommendation System," 2018 IEEE MIT Undergraduate Research Technology Conference (URTC), Cambridge, MA, USA, 2018, 5 pages.

Zakari et al., "Are There Limitations to Exercise Benefits in Peripheral Arterial Disease?," Frontiers in Cardiovascular Medicine, Nov. 2018, vol. 5, Article 173, 12 pages.

You et al., "Including Blood Vasculature into a Game-Theoretic Model of Cancer Dynamics," Games 2019, 10, 13, 22 pages.

Jeong et al., "Computer-assisted upper extremity training using interactive biking exercise (iBikE) platform," Sep. 2012, 34th Annual International Conference of the IEEE EMBS, 5 pages.

Gerbild et al., "Physical Activity to Improve Erectile Dysfunction: A Systematic Review of Intervention Studies," Sexual Medicine, 2018, 15 pages.

Website for "Pedal Exerciser", p. 1, retrieved on Sep. 9, 2022 from https://www.vivehealth.com/collections/physical-therapy-equipment/products/pedalexerciser.

Website for "Functional Knee Brace with ROM", p. 1, retrieved on Sep. 9, 2022 from http://medicalbrace.gr/en/product/functional-knee-brace-with-goniometer-mbtelescopicknee/.

Website for "ComfySplints Goniometer Knee", pp. 1-5, retrieved on Sep. 9, 2022 from https://www.comfysplints.com/product/knee-splints/.

(56) References Cited

OTHER PUBLICATIONS

Website for “BMI FlexEze Knee Corrective Orthosis (KCO)”, pp. 1-4, retrieved on Sep. 9, 2022 from https://orthobmi.com/products/bmi-flexeze%C2%AE-knee-corrective-orthosis-kco.
Website for “Neoprene Knee Brace with goniometer—Patella Rom MB.4070”, pp. 1-4, retrieved on Sep. 9, 2022 from https://www.fortuna.com.gr/en/product/neoprene-knee-brace-with-goniometer-patella-rom-mb-4070/.
Kuiken et al., “Computerized Biofeedback Knee Goniometer: Acceptance and Effect on Exercise Behavior in Post-total Knee Arthroplasty Rehabilitation,” Biomedical Engineering Faculty Research and Publications, 2004, pp. 1-10.
Ahmed et al., “Artificial intelligence with multi-functional machine learning platform development for better healthcare and precision medicine,” Database, 2020, pp. 1-35.
Davenport et al., “The potential for artificial intelligence in healthcare,” Digital Technology, Future Healthcare Journal, 2019, pp. 1-5, vol. 6, No. 2.
Website for “OxeFit XS1”, pp. 1-3, retrieved on Sep. 9, 2022 from https://www.oxefit.com/xs1.
Website for “Preva Mobile”, pp. 1-6, retrieved on Sep. 9, 2022 from https://www.precor.com/en-us/resources/introducing-preva-mobile.
WEBSITE for “J-Bike”, pp. 1-3, retrieved on Sep. 9, 2022 from https://www.magneticdays.com/en/cycling-for- physical-rehabilitation.
Website for “Excy”, pp. 1-12, retrieved on Sep. 9, 2022 from https://excy.com/portable-exercise-rehabilitation-excy-xcs-pro/.
Website for “OxeFit XP1”, pp. 1, retrieved on Sep. 9, 2022 from https://www.oxefit.com/xp1.
Malloy, Online Article “AI-enabled EKGs find difference between numerical age and biological age significantly affects health, longevity”, Website: https://newsnetwork.mayoclinic.org/discussion/ai-enabled-ekgs-find-difference-between-numerical-age-and-biological-age-significantly-affects-health-longevity/, Mayo Clinic News Network, May 20, 2021, retrieved: Jan. 23, 2023, p. 1-4.
Jeong et al., “Computer-assisted upper extremity training using interactive biking exercise (iBikE) platform,” Sep. 2012, pp. 1-5, 34th Annual International Conference of the IEEE EMBS.
Barrett et al., “Artificial intelligence supported patient self-care in chronic heart failure: a paradigm shift from reactive to predictive, preventive and personalised care,” EPMA Journal (2019), pp. 445-464.
Oerkild et al., “Home-based cardiac rehabilitation is an attractive alternative to No. cardiac rehabilitation for elderly patients with coronary heart disease: results from a randomised clinical trial,” BMJ Open Accessible Medical Research, Nov. 22, 2012, pp. 1-9.
Bravo-Escobar et al., “Effectiveness and safety of a home-based cardiac rehabilitation programme of mixed surveillance in patients with ischemic heart disease at moderate cardiovascular risk: A randomised, controlled clinical trial,” BMC Cardiovascular Disorders, 2017, pp. 1-11, vol. 17:66.
Thomas et al., “Home-Based Cardiac Rehabilitation,” Circulation, 2019, pp. e69-e89, vol. 140.
Thomas et al., “Home-Based Cardiac Rehabilitation,” Journal of the American College of Cardiology, Nov. 1, 2019, pp. 133-153, vol. 74.
Thomas et al., “Home-Based Cardiac Rehabilitation,” HHS Public Access, Oct. 2, 2020, pp. 1-39.
Dittus et al., “Exercise-Based Oncology Rehabilitation: Leveraging the Cardiac Rehabilitation Model,” Journal of Cardiopulmonary Rehabilitation and Prevention, 2015, pp. 130-139, vol. 35.
Chen et al., “Home-based cardiac rehabilitation improves quality of life, aerobic capacity, and readmission rates in patients with chronic heart failure,” Medicine, 2018, pp. 1-5 Vol. 97:4.
Lima de Melo Ghisi et al., “A systematic review of patient education in cardiac patients: Do they increase knowledge and promote health behavior change?,” Patient Education and Counseling, 2014, pp. 1-15.
Fang et al., “Use of Outpatient Cardiac Rehabilitation Among Heart Attack Survivors—20 States and the District of Columbia, 2013 and Four States, 2015,” Morbidity and Mortality Weekly Report, vol. 66, No. 33, Aug. 25, 2017, pp. 869-873.
Beene et al., “AI and Care Delivery: Emerging Opportunities for Artificial Intelligence to Transform How Care Is Delivered,” Nov. 2019, American Hospital Association, pp. 1-12.
Jeong et al., “Remotely controlled biking is associated with improved adherence to prescribed cycling speed,” Technology and Health Care 23, 2015, 7 pages.
Laustsen et al., “Telemonitored exercise-based cardiac rehabilitation improves physical capacity and health-related quality of life,” Journal of Telemedicine and Telecare, 2020, DOI: 10.1177/1357633X18792808, 9 pages.
Blasiak et al., “CURATE.AI: Optimizing Personalized Medicine with Artificial Intelligence, ”SLAS Technology: Translating Life Sciences Innovation, 2020, 11 pages.
Jennifer Bresnick, “What is the Role of Natural Language Processing in Healthcare?”, pp. 1-7, published Aug. 18, 2016, retrieved on Feb. 1, 2022 from https://healthitanalytics.com/ featu res/what-is-the-role-of-natural-language-processing-in-healthcare.
Alex Bellec, “Part-of-Speech tagging tutorial with the Keras Deep Learning library,” pp. 1-16, published Mar. 27, 2018, retrieved on Feb. 1, 2022 from https://becominghuman.ai/part-of-speech-tagging-tutorial-with-the-keras-deep-learning-library-d7f93fa05537.
Kavita Ganesan, All you need to know about text preprocessing for NLP and Machine Learning, pp. 1-14, published Feb. 23, 2019, retrieved on Feb. 1, 2022 from https:// towardsdatascience.com/all-you-need-to-know-about-text-preprocessing-for-nlp-and-machine-learning-bcl c5765ff67.
Badreesh Shetty, “Natural Language Processing (NPL) for Machine Learning,” pp. 1-13, published Nov. 24, 2018, retrieved on Feb. 1, 2022 from https://towardsdatascience. com/natural-language-processing-nlp-for-machine-learning-d44498845d5b.
Boulanger Pierre et al., “A Low-cost Virtual Reality Bike for Remote Cardiac Rehabilitation”, Dec. 7, 2017, Advances in Biometrics: International Conference, ICB 2007, Seoul, Korea, pp. 155-166.
Yin Chieh et al., “A Virtual Reality-Cycling Training System for Lower Limb Balance Improvement”, BioMed Research International, vol. 2016, pp. 1-10.
Ruiz Ivan et al., “Towards a physical rehabilitation system using a telemedicine approach”, Computer Methods in Biomechanics and Biomedical Engineering: Imaging & Visualization, vol. 8, No. 6, Jul. 28, 2020, pp. 671-680, XP055914810.
De Canniere Helene et al., “Wearable Monitoring and Interpretable Machine Learning Can Objectively Track Progression in Patients during Cardiac Rehabilitation”, Sensors, vol. 20, No. 12, Jun. 26, 2020, XP055914617, pp. 1-15.
Shen et al, “Intelligent inverse treatment planning via deep reinforcement learning, a proof-of-principle study in high dose-rate brachytherapy for cervical cancer,” pp. 1-17, May 29, 2019, Phys. Med. Biol. vol. 64, No. 115013.
Fraass et al, “The impact of treatment complexity and computer-control delivery technology on treatment delivery errors,” pp. 651-659, Oct. 1, 1998, International Journal of Radiation Oncology Biology Physics, vol. 42, Issue 3, https://doi.org/:10.1016/s0360-3016(98)00244-2. PMID: 9806527.
Marchal-Crespo et al, “Review of control strategies for robotic movement training after neurologic injury,” pp. 1-15, Jun. 16, 2009, Journal of NeuroEngineering and Rehabilitation, vol. 6, No. 20, https://doi.org/10.1186/1743-0003-6-20.
Karboub et al., “A Machine Learning Based Discharge Prediction of Cardiovascular Diseases Patients in Intensive Care Units.,” pp. 1-23, May 24, 2022, Healthcare (Basel, Switzerland) MDPI, vol. 10(6), No. 966, https://doi. org/10.3390/healthcare10060966.
Chrif et al, “Control design for a lower-limb paediatric therapy device using linear motor technology,” pp. 119-127, Jun. 9, 2017, Biomedical Usignal Processing and Control, vol. 38, https://www.sciencedirect.com/science/article/pii/S1746809417301027.
International Preliminary Report on Patentability of International Application No. PCT/2024/022550, Date of Mailing Sep. 20, 2025, 7 pages.

(56) References Cited

OTHER PUBLICATIONS

Ahmed et al., "Artificial Intelligence With Multi-Functional Machine Learning Platform Development for Better Healthcare and Precision Medicine," Database (Oxford), 2020, pp. 1-35, vol. 2020.
Davenport et al., "The Potential for Artificial Intelligence in Healthcare," Future Healthcare Journal, 2019, pp. 94-98, vol. 6, No. 2.
Capecci et al. 2016, "Physical rehabilitation exercises assessment based on Hidden Semi-Marlkov Model by Kinect v2," 2016 IEEE-EMBS International Conference on Biomedical and Health Informatics (BHI), Las Vegas, NV, USA, 2016, pp. 256-259, doi: 10.1109/BH 1.2016. 7 455883.
Cespedes et al. 2020, "Social Human-Robot Interaction for Gait Rehabilitation," in IEEE Transactions on Neural Systems and Rehabilitation Engineering, vol. 28, No. 6, pp. 1299-1307, Jun. 2020, doi: 10.1109/TNSRE.2020.2987428.
Jamil, Faisal, et al. "Towards secure fitness framework based on IoT-enabled blockchain network integrated with machine learning algorithms." Sensors 21.5 (2021): 1640. (Year: 2021).
Lown, et al. "Machine Learning Detection of Atrial Fibrillation Using Wearable Technology," Jan. 24, 2020; https://doi.org/10.1371/journal.pen.0227401 (year 2020).
Dzierzanowski et al. 1985, "Gaitspert: An Expert System for the Evaluation of Abnormal Human Locomotion Arising from Stroke," in IEEE Transactions on Biomedical Engineering, vol. BME-32, No. 11, pp. 935-942, Nov. 1985, doi: 10.1109/TBME.1985.325626.
Ona et al. 2018, "Review of Robotics in Neurorehabilitation: Towards an Automated Process for Upper Limb,"J Healthc Eng. Apr. 2018 ;2018:9758939. doi: 10.1155/2018/9758939. PMID: 29707189; PMCID: PMC5901488.
Treadmill Reviews, "All About Using iFit with your Treadmill", (Jul. 9, 2019) (Year: 2019).
Nissim N, Boland MR, Tatonetti NP, Elovici Y, Hripcsak G, Shahar Y, Moskovitch R. Improving condition severity classification with an efficient active learning based framework. J Biomed Inform. Jun. 2016;61 :44-54. doi: 10.1016/j.jbi.2016.03.016. Epub Mar. 22, 2016. PMID: 27016383; PMCID: PMC5486916. (Year: 2016).
Jennie Dusheck, "Wearable sensors can tell when you are getting sick", (Jan. 12, 2017) (Year: 2017).
Anton et al., "A Telerehabilitation System for the Selection, Evaluation and Remote Management of Therapies," Sensors, vol. 18, No. 5, Article 1459 (2018)) (Year: 2018).
Joudaki et al., "Using Data Mining to Detect Health Care Fraud and Abuse: A Review of Literature", Global Journal of Health Science, vol. 7, No. 1, 2015 (Year: 2015).

* cited by examiner

SYSTEM AND METHOD FOR USING ARTIFICIAL INTELLIGENCE AND A PAYMENT SYSTEM PERTAINING TO COMPONENTS OF MAPPED EXERCISES

CROSS-REFERENCE TO RELATED APPLICATIONS

This application is a continuation of U.S. patent application Ser. No. 18/259,708, filed Jun. 29, 2023, which is a national stage application of International Patent Application No. PCT/US2022/050120, filed Nov. 16, 2022, which claims priority to and the benefit of U.S. Prov. Pat. App. No. 63/280,835, filed Nov. 18, 2021. All applications are incorporated herein in their entirety for all purposes.

TECHNICAL FIELD

This disclosure relates in general to rehabilitation and, in particular, to a system, whether floor mounted or tabletop; apparatus, whether floor mounted or tabletop; and method for rehabilitation of, for example, the orthopedic joints of a user.

BACKGROUND

Remote medical assistance, or telemedicine, may aid a patient in performing various aspects of a rehabilitation regimen for a body part. The patient may use a patient interface in communication with an assistant interface for receiving the remote medical assistance via audio, visual, and/or audiovisual communications.

SUMMARY

Embodiments of a system, method and apparatus for rehabilitation exercise are disclosed. For example, a computer-implemented system may include an electromechanical machine and a processing device communicatively coupled to motors. The processing device executes instructions to receive data comprising a treatment plan including one or more prescribed exercises for a user to perform using the electromechanical machine; generates, based on the data, a motion profile for an assembly of the electromechanical machine, wherein the assembly is coupled to a carriage to enable movement along a length of an arm, wherein the carriage is coupled to each cable of the first set of cables; executes a transformation function to implement a desired virtual apparatus model using the electromechanical machine, wherein, to implement the desired virtual apparatus model, the transformation function maps the motion profile to one or more coordinates in a domain; and controls, using the desired virtual apparatus model, the one or more motors of the electromechanical machine.

In one embodiment, a computer-implemented system may include an electromechanical machine including one or more motors mounted to a body and spaced apart from each other, and a first set of cables, each coupled to a respective one of the motors. The system may include a processing device communicatively coupled to the one or more motors, wherein the processing device executes instructions implementing a control system to receive data comprising a treatment plan. The treatment plan includes one or more prescribed exercises for a user to perform using the electromechanical machine. The processing device may generate, based on the data and certain criteria, a motion profile for an assembly of the electromechanical machine. The motion profile includes a movement shape of one or more portions of the electromechanical machine. The processing device may execute a transformation function to implement, using the electromechanical machine, a desired virtual apparatus model, wherein, to implement the desired virtual apparatus model, the transformation function maps the motion profile to one or more coordinates in a domain. The processing device may control, using the desired virtual apparatus model, the one or more motors of the electromechanical machine.

In one embodiment, a computer-implemented system includes an electromechanical machine including one or more motors mounted to a body and spaced apart from each other, and a first set of cables, each coupled to a respective one of the motors. The system includes a processing device communicatively coupled to the one or more motors, wherein the processing device executes instructions implementing a control system to receive first data comprising information pertaining to motion of one or more pedals of the electromechanical machine. The motion is associated with one or more users performing one or more treatment plans. The processing device may receive second data comprising information pertaining to one or more characteristics of the one or more users performing the treatment plan. The characteristics comprise performance information, measurement information, personal information, or some combination thereof. The processing device may identify one or more correlations between at least some of the first data and at least some of the second data, and may generate, based on the one or more treatment plans and the one or more correlations, one or more motion profiles for an assembly of the electromechanical machine.

In one embodiment, a computer-implemented system may include an electromechanical machine including one or more motors mounted to a body and spaced apart from each other, and a first set of cables, each coupled to a respective one of the motors. The system may include a processing device communicatively coupled to the one or more motors, wherein the processing device executes instructions implementing a control system to receive data comprising a treatment plan including one or more prescribed exercises for a user to perform using the electromechanical machine, generate, based on the data, a motion profile for an assembly of the electromechanical machine, and determine, based on a prescribed exercise of the one or more prescribed exercises, one or more components to include to enable the user to perform, using the electromechanical machine, the prescribed exercise. The processing device may validate, based on the one or more components and configuration information pertaining to the electromechanical machine, whether the motion profile associated with the prescribed exercise is achievable with respect to a threshold achievement level. Responsive to determining that the motion profile associated with the prescribed exercise is unachievable with respect to the threshold achievement level, the processing device may determine, based on the one or more components and the configuration information, at least one missing component needed to achieve, with respect to the threshold achievement level, the motion profile for the prescribed exercise.

In one embodiment, a computer-implemented system may include an electromechanical machine including one or more motors mounted to a body and spaced apart from each other, and a first set of cables, each coupled to a respective one of the motors. The system includes a processing device communicatively coupled to the one or more motors, wherein the processing device executes instructions implementing a control system to receive data including a treatment plan including one or more prescribed exercises for a user to perform using the electromechanical machine, generate, using a treatment machine description language and based on one or more desired goals of a user, a virtual apparatus model of the electromechanical machine, wherein the virtual apparatus model is generated by a trained machine learning model, and generate, using the virtual apparatus model and the data, a motion profile. The processing device may control, using the motion profile, the one or more motors.

BRIEF DESCRIPTION OF THE DRAWINGS

So that the manner in which the features and advantages of the embodiments are attained and can be understood in more detail, a more particular description can be had by reference to the embodiments that are illustrated in the appended drawings. However, the drawings illustrate only some embodiments and are not to be considered limiting in scope since there can be other equally effective embodiments. It shall be noted that some of the details and/or features shown in the drawings herein may not be drawn to scale for clarity purposes.

The use of the same reference symbols in different drawings indicates similar or identical items.

NOTATION AND NOMENCLATURE

Figure 1:
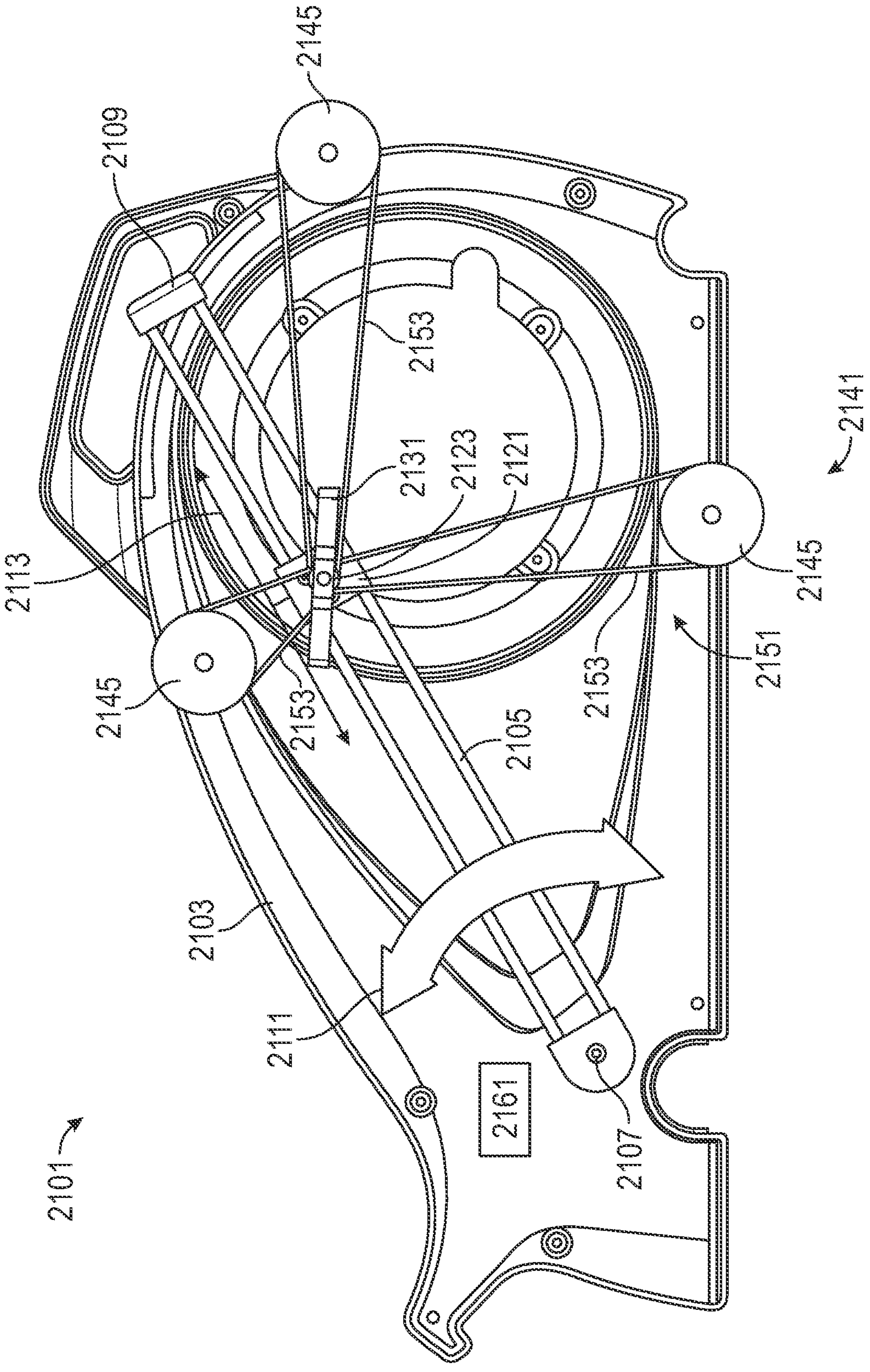
FIG. 1 is a schematic side view of an embodiment of a rehabilitation machine.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . " unless otherwise stated. Also, the term "couple" or "couples" is intended to mean either an indirect or direct connection unless specified. Thus, if not more specific, "a first device is coupled to a second device" is intended to mean that that connection between the first device and the second device may be through a direct connection or through an indirect connection via other devices and connections.

The terminology used herein is for the purpose of describing particular example embodiments only, and is not intended to be limiting. As used herein, the singular forms "a," "an," and "the" may be intended to include the plural forms as well, unless the context clearly indicates otherwise. For example, "a processor" programmed to perform certain actions can mean "more than one processors" that collectively perform the certain actions. The method steps, processes, and operations described herein are not to be construed as necessarily requiring their performance in the particular order discussed or illustrated, unless specifically identified as an order of performance. It is also to be understood that additional or alternative steps may be employed.

The terms first, second, third, etc. may be used herein to describe various elements, components, regions, layers and/or sections; however, these elements, components, regions, layers and/or sections should not be limited by these terms. These terms may be only used to distinguish one element, component, region, layer, or section from another region, layer, or section. Terms such as "first," "second," and other numerical terms, when used herein, do not imply a sequence or order unless clearly indicated by the context. Thus, a first element, component, region, layer, or section discussed below could be termed a second element, component, region, layer, or section without departing from the teachings of the example embodiments. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C. In another example, the phrase "one or more" when used with a list of items means there may be one item or any suitable number of items exceeding one.

Spatially relative terms, such as "inner," "outer," "beneath," "below," "lower," "above," "upper," "top," "bottom," and the like, may be used herein. These spatially relative terms can be used for ease of description to describe one element's or feature's relationship to another element(s) or feature(s) as illustrated in the figures. The spatially relative terms may also be intended to encompass different orientations of the device in use, or operation, in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptions used herein interpreted accordingly.

A "treatment plan" may include one or more treatment protocols, and each treatment protocol includes one or more treatment sessions. Each treatment session comprises several session periods, with each session period including a particular exercise for treating the body part of the patient. For example, a treatment plan for post-operative rehabilitation after a knee surgery may include an initial treatment protocol with twice daily stretching sessions for the first 3 days after surgery and a more intensive treatment protocol with active exercise sessions performed 4 times per day starting 4 days after surgery. A treatment plan may also include information pertaining to a medical procedure to perform on the patient, a treatment protocol for the patient using a treatment apparatus, a diet regimen for the patient, a medication regimen for the patient, a sleep regimen for the patient, additional regimens, or some combination thereof.

The terms telemedicine, telehealth, telemed, teletherapeutic, remote medicine, etc. may be used interchangeably herein. The term "condition" may be used to refer to a disease or other attribute of the user.

As used herein, the term "healthcare professional" may include a medical professional (e.g., such as a doctor, a nurse, a therapist, and the like), an exercise professional (e.g., such as a coach, a trainer, a nutritionist, and the like), or another professional sharing at least one of medical and exercise attributes (e.g., such as an exercise physiologist, a physical therapist, an occupational therapist, and the like). As used herein, and without limiting the foregoing, a "healthcare professional" may be a human being, a robot, a virtual assistant, a virtual assistant in virtual and/or augmented reality, or an artificially intelligent entity, such entity including a software program, integrated software and hardware, or hardware alone.

As used herein, the terms treatment apparatus, exercise apparatus, exercise device, treatment device, machine, electromechanical machine, electromechanical device, workout device, workout apparatus, rehabilitation apparatus, rehabilitation device, rehabilitation machine, prehabilitation apparatus, prehabilitation device, and/or prehabilitation machine may be used interchangeably herein. For example, an exercise bike, stationary bike, treadmill, rowing machine, elliptical machine, stair mill (aka stair climber), and the like can all be referred to as a treatment apparatus, exercise apparatus, exercise device, treatment device, machine, electromechanical machine, electromechanical device, workout device, workout apparatus, rehabilitation apparatus, rehabilitation device, rehabilitation machine, prehabilitation apparatus, prehabilitation device, and/or prehabilitation machine. In the interest of brevity, the term "machine," "electromechanical machine," or "treatment apparatus" are often used throughout and are intended to cover any one or more of these devices.

As used herein, the term a sudden movement or "jerk" may refer to moving the portion of the treatment apparatus very quickly (or as quickly as possible) from an initial position to a second stationary position.

Any term used herein to characterize a variance (e.g., such as difference, differential, etc.) referenced anywhere in this disclosure, including, without limitation, the differential data, may be characterized or described by an absolute number or number of units (e.g., "3", "5 inches", "25 degrees" "0.15 radians" and the like), by a percentage difference (e.g., "20% more", "15% less"), by a percentage point difference (e.g., "5.3 percentage points less than (or greater than)), by a parametrically ranked difference (e.g., "2nd highest vs. 5th highest", therefore, e.g., 2 ranks higher than 5), by a qualitatively described difference (e.g., "very different", "somewhat different", "equal", "more than", "better than", "less than", "worse than" and the like), or by any other means of expressing or describing a difference).

As used herein, the term "motion profile" may refer to a specification of movement of a portion of an electromechanical machine. The specification may describe a shape (e.g., circular, elliptical, rectangular, square, oval, any geometrical shape, etc.) of a movement path for the portion to follow. The motion profile may specify which portion is to move, when the portion is to move, how the portion is to move (e.g., which components cause the movement of the portion), etc. The motion profile may specify various operating parameters of the portion of the electromechanical machine, such as a range of motion, a speed, an acceleration, an amount of resistive force to provide, and the like. The motion profile may specify various coordinates in an n-dimensional domain, where the coordinates represent points through which the portion is to move during operation.

DETAILED DESCRIPTION

The following discussion is directed to various embodiments of the present disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Determining a treatment plan for a patient having certain characteristics (e.g., vital-sign or other measurements; performance; demographic; geographic; diagnostic; measurement- or test-based; medically historic; behavioral historic; cognitive; etiologic; cohort-associative; differentially diagnostic; surgical, physically therapeutic, pharmacologic and other treatment(s) recommended; etc.) may be a technically challenging problem. For example, a multitude of information may be considered when determining a treatment plan, which may result in inefficiencies and inaccuracies in the treatment plan selection process. In a rehabilitative setting, some of the multitude of information considered may include characteristics of the patient such as personal information, performance information, and measurement information. The personal information may include, e.g., demographic, psychographic or other information, such as an age, weight, gender, height, body mass index, medical condition, one or more comorbidities, the values or descriptive results of tests which comprise blood, tissue, radiologic or other assays, personal or familial medication history, injury, medical procedure, medication prescribed, or some combination thereof. The performance information may include, e.g., an elapsed time of using an exercise apparatus, an amount of force exerted on a portion of the exercise apparatus, a range of motion achieved on the exercise apparatus, a movement speed of a portion of the exercise apparatus, an indication of a plurality of pain levels using the exercise apparatus, or some combination thereof. The measurement information may include, e.g., a vital sign, a respiration rate, a heartrate, a temperature, a blood pressure, blood oxygen level (SpO2) or some combination thereof. It may be desirable to process the characteristics of a multitude of patients, the treatment plans performed for those patients, and the results of the treatment plans for those patients.

Further, another technical problem may involve distally treating, via a computing device during a telemedicine or telehealth session, a patient from a location different than a location at which the patient is located. An additional technical problem is controlling or enabling the control of, from the different location, an exercise apparatus used by the patient at the location at which the patient is located. Oftentimes, when a patient undergoes rehabilitative surgery (e.g., knee surgery), a physical therapist or other medical professional may prescribe an exercise apparatus to the patient to use to perform a treatment protocol at their residence or any mobile location or temporary domicile. A healthcare professional may refer to a doctor, physician assistant, nurse, chiropractor, dentist, physical therapist, acupuncturist, physical trainer, or the like. A medical professional may refer to any person with a credential, license, degree, or the like in the field of medicine, physical therapy, rehabilitation, or the like.

When the healthcare professional is located in a different location from the patient and the exercise apparatus, it may be technically challenging for the healthcare professional to monitor the patient's actual progress (as opposed to relying on the patient's word about their progress) using the exercise apparatus, modify the treatment plan according to the patient's progress, adapt the exercise apparatus to the personal characteristics of the patient as the patient performs the treatment plan, and the like.

Additionally, or alternatively, the two or more healthcare professionals may treat the patient (e.g., for the same condition, different conditions, related conditions, and the like). For example, an orthopedic surgeon, a physical therapist, and/or one or more other healthcare professionals may cooperatively or independently treat or be responsible for treatment of the patient for the same condition or a related condition. Such healthcare professionals may be located remotely from the patient and/or one another. Accordingly, systems and methods, such as those described herein, that coordinate schedules of the two or more healthcare professionals to provide treatment to the patient via a telemedicine session, may be desirable.

Accordingly, embodiments of the present disclosure pertain to using artificial intelligence and/or machine learning to assign patients to cohorts and to dynamically control an exercise apparatus based on the assignment during an adaptive telemedical session. In some embodiments, numerous treatment apparatuses may be provided to patients. The exercise apparatuses may be used by the patients to perform treatment plans in their residences, at a gym, at a rehabilitative center, at a hospital, or any suitable location, including permanent or temporary domiciles.

Figure 2:
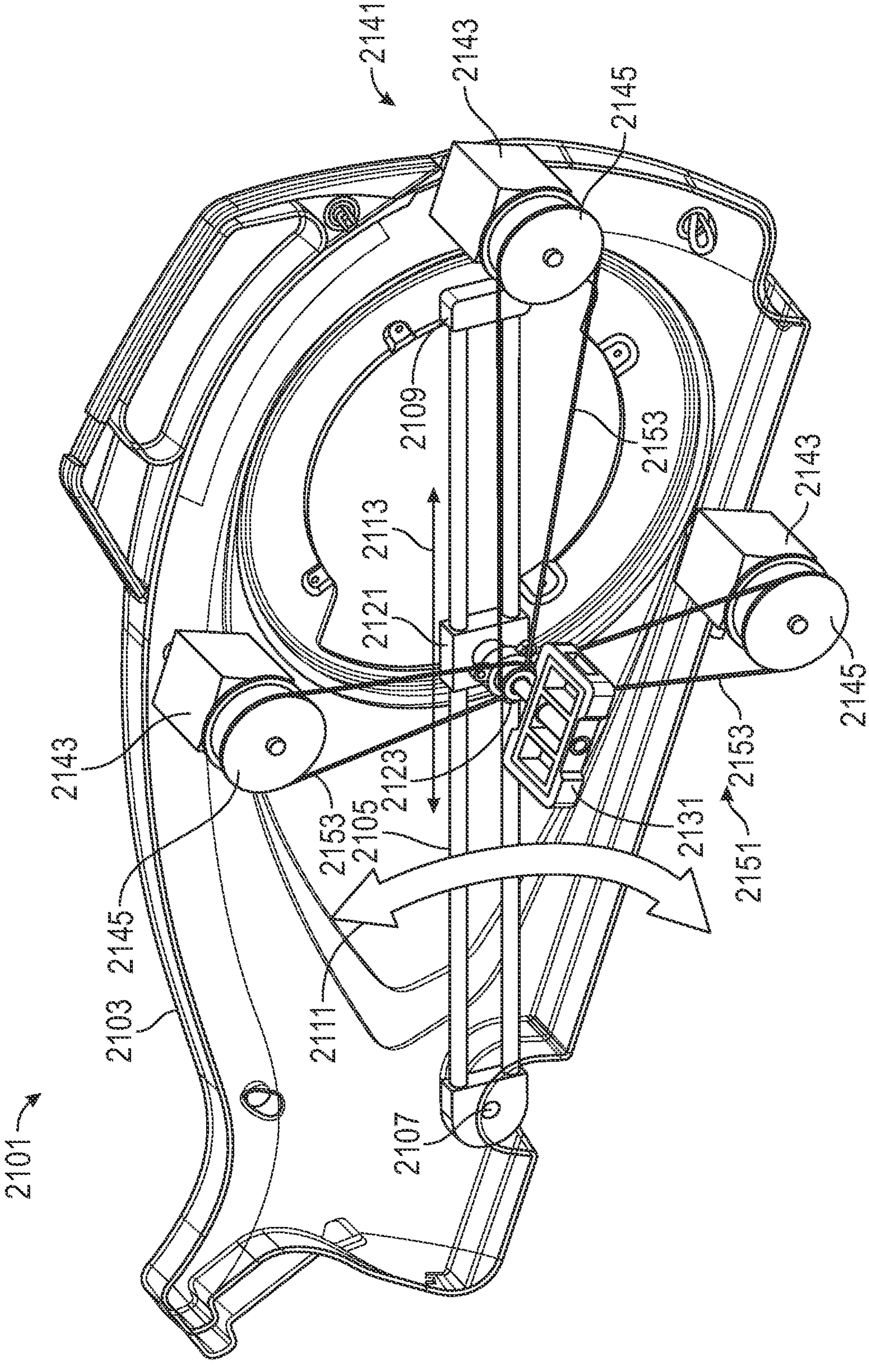
FIG. 2 is a schematic isometric view of an embodiment of the rehabilitation machine of FIG. 1.

Embodiments of a system, method and apparatus for joint rehabilitation and exercise are disclosed in FIGS. 1-13. For example, FIGS. 1 and 2 depict an embodiment of a machine 2101 that includes a body 2103 and an arm 2105, such as one arm 2105 on each major side of the body 2103. In FIGS. 1 and 2, only one of the arms 2105 is shown for ease of illustration.

Each arm 2105 can have a proximal end 2107 and a distal end 2109. Versions of the proximal end 2107 can be pivotally mounted (see arrow 2111) to the body 2103. The distal end 2109 can be free to move relative to the body 2103. In one example, the machine 2101 does not have a seat for the user to sit on while using the machine 2101. In this version, the user must be seated away from the machine 2101 on a separate seat (not shown) to use the machine 2101.

Embodiments of the machine 2101 can further include a carriage 2121 slidably mounted (see arrow 2113) to respective ones of the arms 2105. Each carriage 2121 can move along a length of a respective one of the arms 2105. The range of motion of the carriages 2121 relative to the arms 2105 can be for a portion of the arms 2105, or almost an entire length of the arms 2105.

In some versions, a pedal assembly 2131, such as one pedal assembly 2131 on each major side of the body 2103, can be included. The pedal assembly 2131 can be rotatably coupled to one of the carriages 2121. The pedal assembly 2131 can move with the carriage 2121 along the length of the arm 2105. Each pedal assembly 2131 can be configured to support a foot of the user of the machine 2101.

Examples of the machine 2101 can include a set 2141 of motors 2143, such as one set 2141 of motors 2143 on each side of the body 2103. The motors 2143 can be mounted to the body 2103. The motors 2143 also can be spaced apart from each other and spaced apart from the distal end 2109 of the arm 2105, such as in the configurations depicted in the drawings. The distal end 2109 of the arm can be free of contact with the motors 2143 over an entire range of motion of the arm 2105 relative to the body 2103.

Some embodiments of the motors 2143 are coupled together. Versions can include a flexible linkage, such as a chain, timing chain or a set 2151 of cables 22153, such as one set 2151 of cables 2153 on each respective side of the body 2103. Examples of the cables 2153 can include each cable 2153 being coupled to a respective one of the motors 2143 and to the respective carriage 2121.

Versions of the machine 2101 can include a control system 2161. Embodiments of the control system 2161 can selectively extend and/or retract the cables 2153 by using the respective motors 2143. Such motion can cause one or more of the pedal assemblies 2131, carriages 2121 and arms 2105 to move relative to the body 2103.

In some examples, the control system 2161 can articulate the pedal assemblies 2131 in prescribed pedaling patterns for a user of the machine. For example, the prescribed pedaling patterns can include ones that are circular, elliptical, oval, square, leg press, stair stepping, vertical up and down, etc. Examples of the control system 2161 also can be configured to control a repetitive speed and resistance of the pedal assemblies 2131 in each of the prescribed pedaling patterns. The pedal assemblies 2131 can be configured to be independently articulated by the control system 161. For example, the pedal assemblies 2131 can be simultaneously articulated in different ones of the prescribed pedaling patterns, as desired.

Embodiments of the control system 2161 can limit a range of motion of each pedal assembly 2131 to an area defined by and within locations of the motors 2143. Essentially, this can be equivalent to the area inside the largest circle shown in FIG. 1. Other versions of the control system 2161 can permit a range of motion of each pedal assembly 2131 to extend beyond an area defined by and within locations of the motors 2143. This example could include the area outside of the largest circle shown in FIG. 1. More detailed information about the control system is included below.

In some versions, each motor 2143 can be a servo motor. In one example, the set 2141 of motors 2143 comprises exactly three motors 2143 that are arranged in a triangular pattern on a side of the body 2103. Embodiments of each motor 2143 can include a respective pulley 2145 that is rotatably coupled thereto and coupled to a respective one of the cables 2153. In addition, the carriage 2121 can include one or more pulleys 2123. Each pulley 2123 can be coupled to a respective one of the cables 2153. In an example, each of the cables 2153 can be a steel cable.

Figure 13:
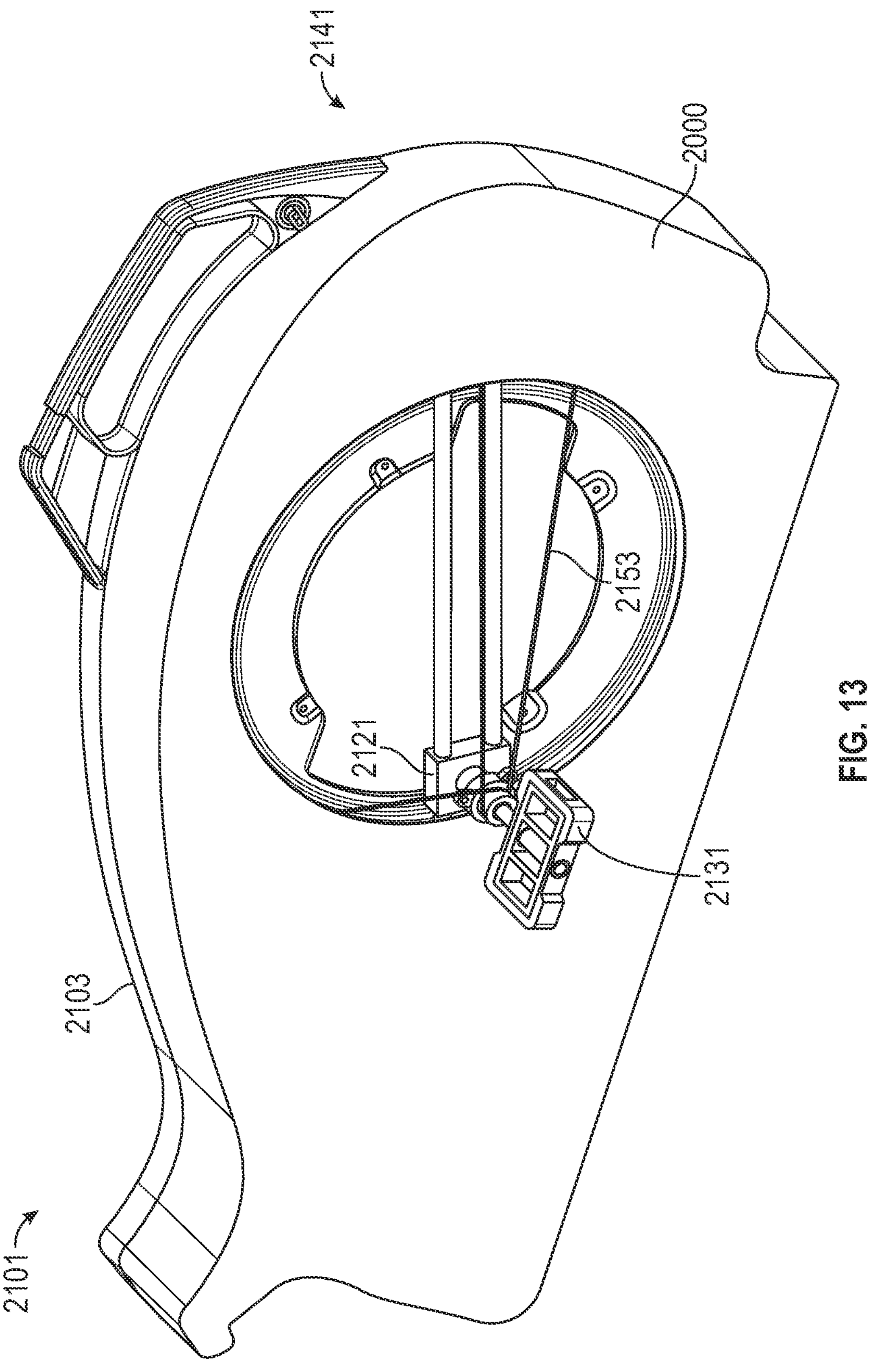
FIG. 13 is a schematic isometric view of another embodiment of the rehabilitation machine.

In some embodiments of the machine 2101, the arms 2104, motors 2143 and cables 2153 can be shrouded to avoid and obstruct pinch points for the user of the machine 2101. This feature can prevent incidental contact with the user. For example, FIG. 13 depicts a schematic, isometric view of another embodiment of the rehabilitation machine 2101. This version is very similar to that of FIG. 2, and further includes a cowling or shroud 2000 that covers most or even all of the moving parts of the rehabilitation machine 2101, such as the motors 2141, pulleys 2145, etc. The depiction in FIG. 13 is merely representative and is not limiting as to how much the shroud 2000 can cover the moving parts. As with the other embodiments, this example has the same equipment on both the left and right sides of the rehabilitation machine 2101. Only one side is shown for ease of illustration. This embodiment can include many, if not all, of the components described for the other embodiments.

Now turning to FIG. 3, a block diagram schematically depicts a computer-implemented system 10, hereinafter called "the system" for managing a treatment plan. Managing the treatment plan may include using an artificial intelligence engine to recommend treatment plans and/or provide excluded treatment plans that should not be recommended to a patient.

The system 10 also includes a server 30 configured to store (e.g., write to an associated memory) and to provide data related to managing the treatment plan. The server 30 may include one or more computers and may take the form of a distributed and/or virtualized computer or computers. The server 30 also includes a first communication interface 32 configured to communicate with the clinician interface 20 via a first network 34. In some embodiments, the first network 34 may include wired and/or wireless network connections such as Wi-Fi, Bluetooth, ZigBee, Near-Field Communications (NFC), cellular data network, etc. The server 30 includes a first processor 36 and a first machine-readable storage memory 38, which may be called a "memory" for short, holding first instructions 40 for performing the various actions of the server 30 for execution by the first processor 36. The server 30 is configured to store data regarding the treatment plan. For example, the memory 38 includes a system data store 42 configured to hold system data, such as data pertaining to treatment plans for treating one or more patients. The server 30 is also configured to store data regarding performance by a patient in following a treatment plan. For example, the memory 38 includes a patient data store 44 configured to hold patient data, such as data pertaining to the one or more patients, including data representing each patient's performance within the treatment plan.

Additionally or alternatively, the characteristics (e.g., personal, performance, measurement, etc.) of the users, the treatment plans followed by the user, the level of compliance with the treatment plans, and the results of the treatment plans may use correlations and other statistical or probabilistic measures to enable the partitioning of or to partition the treatment plans into different patient cohort-equivalent databases in the patient data store 44. For example, the data for a first cohort of first patients having a first similar injury, a first similar medical condition, a first similar medical procedure performed, a first treatment plan followed by the first patient, and a first result of the treatment plan may be stored in a first patient database. The data for a second cohort of second patients having a second similar injury, a second similar medical condition, a second similar medical procedure performed, a second treatment plan followed by the second patient, and a second result of the treatment plan may be stored in a second patient database. Any single characteristic or any combination of characteristics may be used to separate the cohorts of patients. In some embodiments, the different cohorts of patients may be stored in different partitions or volumes of the same database. There is no specific limit to the number of different cohorts of patients allowed, other than as limited by mathematical combinatoric and/or partition theory.

This characteristic data, treatment plan data, and results data may be obtained from numerous treatment apparatuses and/or computing devices and/or digital storage media over time and stored in the data store 44. The characteristic data, treatment plan data, and results data may be correlated in the patient-cohort databases in the patient data store 44. The characteristics of the people may include personal information, performance information, and/or measurement information.

In addition to the historical information about other people stored in the patient cohort-equivalent databases, real-time or near-real-time information based on the current patient's characteristics about a current patient being treated may be stored in an appropriate patient cohort-equivalent database. The characteristics of the patient may be determined to match or be similar to the characteristics of another person in a particular cohort (e.g., cohort A) and the patient may be assigned to that cohort.

In some embodiments, the server 30 may execute an artificial intelligence (AI) engine 11 that uses one or more machine learning models 13 to perform at least one of the embodiments disclosed herein. The server 30 may include a training engine 9 capable of generating the one or more machine learning models 13. The machine learning models 13 may be trained to assign people to certain cohorts based on their characteristics, select treatment plans using real-time and historical data correlations involving patient cohort-equivalents, and control an electromechanical machine 101, among other things. The machine learning models 13 may be trained to generate, based on data associated with a diagnosis of users, initial treatment plans to be performed on the electromechanical machine 101 by the users. For example, the machine learning models 13 may be trained to provide a visual stimulus, audio stimulus, or haptic stimulus.

The machine learning models 13 may also be configured, for example, to display on a user interface or otherwise inform the user of a goal for the day, where the goal is dependent upon the generated treatment plan. For example, the machine learning models may be configured to request a measurement of a vital sign of the user, a respiration rate of the user, a heartrate of the user, a heart rhythm of a user, an oxygen saturation level of the user, a sugar level of the user, a composition of blood of the user, cerebral activity of the user, cognitive activity of the user, a lung capacity of the user, a temperature of the user, a blood pressure of the user, an eye movement of the user, a degree of dilation of an eye of the user, a reaction time, a sound produced by the user, a perspiration rate of the user, an elapsed time of using the electromechanical machine 101, an amount of force exerted on a portion of the electromechanical machine 101, a range of motion achieved on the electromechanical machine 101, a movement speed of a portion of the electromechanical machine 101, a pressure exerted on a portion of the electromechanical machine 101, a movement acceleration of a portion of the electromechanical machine 101, a sudden movement (such as a jerk) of a portion of the electromechanical machine 101, a torque level of a portion of the electromechanical machine 101, and an indication of a plurality of pain levels experienced by the user when using the electromechanical machine 101. The requested metric may require an input of sensor data or, in some embodiment, may only require manual entry by the user. In some embodiments, the metrics that the machine learning models 13 are trained to monitor are related to the underlying condition or attribute of the user. In other embodiments, the metric that the machine learning models 13 are trained to monitor are related to an underlying condition of the user.

The one or more machine learning models 13 may be generated by the training engine 9 and may be implemented in computer instructions executable by one or more processing devices of the training engine 9 and/or the servers 30. To generate the one or more machine learning models 13, the training engine 9 may train the one or more machine learning models 13. The one or more machine learning models 13 may be used by the artificial intelligence engine 11.

The training engine 9 may be a rackmount server, a router computer, a personal computer, a portable digital assistant, a smartphone, a laptop computer, a tablet computer, a netbook, a desktop computer, an Internet of Things (IoT) device, any other suitable computing device, or a combination thereof. The training engine 9 may be cloud-based or a real-time software platform, and it may include privacy software or protocols, and/or security software or protocols.

To train the one or more machine learning models 13, the training engine 9 may use a training data set of a corpus of the characteristics (e.g., medical diagnoses, attributes, a measurement of a vital sign of the user, a respiration rate of the user, a heartrate of the user, a heart rhythm of a user, an oxygen saturation level of the user, a sugar level of the user, a composition of blood of the user, cerebral activity of the user, cognitive activity of the user, a lung capacity of the user, a temperature of the user, a blood pressure of the user, an eye movement of the user, a degree of dilation of an eye of the user, a reaction time, a sound produced by the user, a perspiration rate of the user, an elapsed time of using the electromechanical machine 101, an amount of force exerted on a portion of the electromechanical machine 101, a range of motion achieved on the electromechanical machine 101, a speed measurement of a portion of the electromechanical machine 101, a pressure exerted on a portion of the electromechanical machine 101, an acceleration of a portion of the electromechanical machine 101, a movement jerk of a portion of the electromechanical machine 101, a torque level of a portion of the electromechanical machine 101, an indication of a plurality of pain levels experienced by the user when using the electromechanical machine 101, etc.) of the people that used the electromechanical machine 101 to perform treatment plans, the details (e.g., treatment protocol including exercises, amount of time to perform the exercises, how often to perform the exercises, a schedule of exercises, parameters/configurations/settings of the electromechanical machine 101 throughout each step of the treatment plan, etc.) of the treatment plans performed by the people using the electromechanical machine 101, and the results of the treatment plans performed by the people. The one or more machine learning models 13 may be trained to match patterns of characteristics of a patient with characteristics of other people assigned to a particular cohort. The term "match" may refer to an exact match, a correlative match, a substantial match, etc. The one or more machine learning models 13 may be trained to receive the characteristics of a patient as input, map the characteristics to characteristics of people assigned to a cohort, and select a treatment plan from that cohort. The one or more machine learning models 13 may also be trained to control, based on the treatment plan, treatment apparatus 70. The one or more machine learning models 13 may also be trained to provide one or more treatment plan options to a healthcare professional to select from and to control the electromechanical machine 101.

Different machine learning models 13 may be trained to recommend different treatment plans for different desired results. For example, one machine learning model may be trained to recommend treatment plans for most effective recovery, while another machine learning model may be trained to recommend treatment plans based on speed of recovery.

In some embodiments, to train the one or more machine learning models 13, the training engine 9 may use a training data set of a corpus of input data (e.g., electromechanical machines represented in a treatment machine description language and desired goals (e.g., treatment plans)) for users. The input data may be labeled as being associated with output data comprising virtual models of desired electromechanical machines and motion profiles, wherein such virtual models are configured to enable achievement the desired goals. In some embodiments, the virtual models may include a list of components needed to perform certain prescribed exercises to achieve the desired goals. In some embodiments, the electromechanical machine prescribed or associated with the user may lack one or more of the components in the list of components. In any such instance, a recommendation may be generated and output to a computing device and the recommendation may include information associated with purchasing or obtaining the missing component such that the user can use the electromechanical machine to perform the prescribed exercise.

In some embodiments, the training engine 9 may train the one or more machine learning models 13 using a corpus of training data, wherein the training data includes labeled treatment plans (e.g., prescribed exercises). The labels of the treatment plans may be associated with certain motion profiles capable of being implementing by using an electromechanical machine 101. To implement a desired virtual electromechanical machine (e.g., desired virtual apparatus model), and by performing one or more transformation functions, the machine learning models may be trained to generate the motion profiles. In order to implement a particular motion profile, the transformation functions may graph in an n-dimensional coordinate plane movement coordinates for the carriage and assembly to follow. To implement the motion profile of the carriage and assembly, the machine learning models 13 may be trained to receive the motion profiles and to generate control instructions to control the motors such that the motors control the cables.

In some embodiments, the machine learning models 13 may be trained to transform the motion profile of the carriage and assembly based on certain criteria. For example, the training data may include inputs of criteria related to one or more muscle groups to be exercised, one or more user characteristics, one or more desired goals, etc., wherein the criteria are mapped to outputs related to motion profiles that have a likelihood (e.g., a degree of probability) of satisfying the certain criteria.

In some embodiments, sensors (e.g., camera, force sensor, motion sensor, proximity sensor, etc.) may be used to monitor the user's result as the user performs prescribed exercises having certain motion profiles. The one or more results may be correlated with the one or more motion profiles. Based on a given correlation, the machine learning models 13 may be retrained to update one or more features of the machine learning models 13. For example, if a certain motion profile leads to an undesirable result, then one or more features (e.g., weights, hidden layer, objective functions, activation functions, etc.) of the machine learning models 13 may be modified such that a different subsequent motion profile associated with a better user result is output.

Using training data that includes training inputs and corresponding target outputs, the one or more machine learning models 13 may refer to model artifacts created by the training engine 9. The training engine 9 may find patterns in the training data wherein such patterns map the training input to the target output, and generate the machine learning models 13 that capture these patterns. In some embodiments, the artificial intelligence engine 11, the database 33, and/or the training engine 9 may reside on another component (e.g., assistant interface 94, clinician interface 20, etc.) depicted in FIG. 3.

The one or more machine learning models 13 may comprise, e.g., a single level of linear or non-linear operations (e.g., a support vector machine [SVM]) or the machine learning models 13 may be a deep network, i.e., a machine learning model comprising multiple levels of non-linear operations. Examples of deep networks are neural networks including generative adversarial networks, convolutional neural networks, recurrent neural networks with one or more hidden layers, and fully connected neural networks (e.g., each neuron may transmit its output signal to the input of the remaining neurons, as well as to itself). For example, the machine learning model may include numerous layers and/or hidden layers that perform calculations (e.g., dot products) using various neurons.

The system 10 also includes a patient interface 50 configured to communicate information to a patient and to receive feedback from the patient. Specifically, the patient interface includes an input device 52 and an output device 54, which may be collectively called a patient user interface 52, 54. The input device 52 may include one or more devices, such as a keyboard, a mouse, a touch screen input, a gesture sensor, and/or a microphone and processor configured for voice recognition. The output device 54 may take one or more different forms including, for example, a computer monitor or display screen on a tablet, smartphone, or a smart watch. The output device 54 may include other hardware and/or software components such as a projector, virtual reality capability, augmented reality capability, etc. The output device 54 may incorporate various visual, audio, or other presentation technologies. For example, the output device 54 may include a non-visual display, such as an audio signal, which may include spoken language and/or other sounds such as tones, chimes, and/or melodies, which may signal different conditions and/or directions. The output device 54 may comprise one or more different display screens presenting various data and/or interfaces or controls for use by the patient. The output device 54 may include graphics, which may be presented by a web-based interface and/or by a computer program or application (App.). In some embodiments, the patient interface 50 may include functionality provided by or similar to existing voice-based assistants such as Siri by Apple, Alexa by Amazon, Google Assistant, or Bixby by Samsung.

Figure 3:
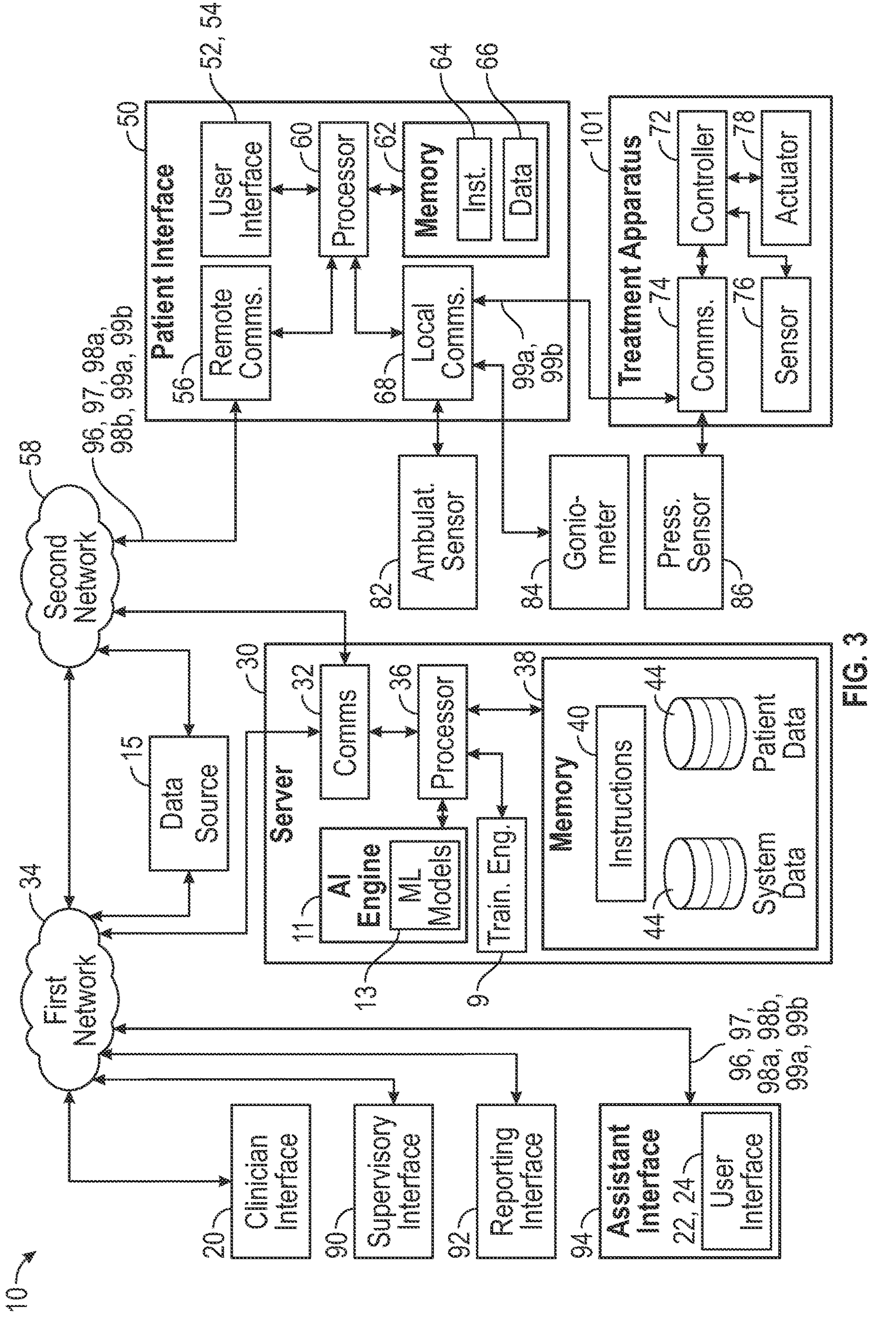
FIG. 3 generally illustrates a block diagram of an embodiment of a computer-implemented system for managing a treatment plan according to the principles of the present disclosure.

As generally illustrated in FIG. 3, the patient interface 50 includes a second communication interface 56, which may also be called a remote communication interface configured to communicate with the server 30 and/or the clinician interface 20 via a second network 58. In some embodiments, the second network 58 may include a local area network (LAN), such as an Ethernet network. In some embodiments, the second network 58 may include the Internet, and communications between the patient interface 50 and the server 30 and/or the clinician interface 20 may be secured via encryption, such as, for example, by using a virtual private network (VPN). In some embodiments, the second network 58 may include wired and/or wireless network connections such as Wi-Fi, Bluetooth, ZigBee, Near-Field Communications (NFC), cellular data network, etc. In some embodiments, the second network 58 may be the same as and/or operationally coupled to the first network 34.

The patient interface 50 includes a second processor 60 and a second machine-readable storage memory 62 holding second instructions 64 for execution by the second processor 60 for performing various actions of patient interface 50. The second machine-readable storage memory 62 also includes a local data store 66 configured to hold data, such as data pertaining to a treatment plan and/or patient data, such as data representing a patient's performance within a treatment plan. The patient interface 50 also includes a local communication interface 68 configured to communicate with various devices for use by the patient in the vicinity of the patient interface 50. The local communication interface 68 may include wired and/or wireless communications. In some embodiments, the local communication interface 68 may include a local wireless network such as Wi-Fi, Bluetooth, ZigBee, Near-Field Communications (NFC), cellular data network, etc.

The system 10 also includes an electromechanical machine 101 configured to be manipulated by the patient and/or to manipulate a body part of the patient for performing activities according to the treatment plan. In some embodiments, the electromechanical machine 101 may take the form of an exercise and rehabilitation apparatus configured to perform and/or to aid in the performance of a rehabilitation regimen, which may be an orthopedic rehabilitation regimen, and the treatment includes rehabilitation of a body part of the patient, such as a joint or a bone or a muscle group. The electromechanical machine 101 may be any suitable medical, rehabilitative, therapeutic, etc. apparatus configured to be controlled distally via another computing device to treat a patient and/or exercise the patient. The electromechanical machine 101 may be an electromechanical machine including one or more weights, an electromechanical bicycle, an electromechanical spin-wheel, a smart-mirror, a treadmill, a stair stepping machine, a rowing machine, a weight lifting machine, a pull up machine, an interactive environment system or the like. The body part may include, for example, a spine, a hand, a foot, a knee, or a shoulder. The body part may include a part of a joint, a bone, or a muscle group, such as one or more vertebrae, a tendon, or a ligament. As generally illustrated in FIG. 3, the electromechanical machine 101 includes a controller 72, which may include one or more processors, computer memory, and/or other components. The electromechanical machine 101 also includes a fourth communication interface 74 configured to communicate with the patient interface 50 via the local communication interface 68. The electromechanical machine 101 also includes one or more internal sensors 76 and an actuator 78, such as a motor. The actuator 78 may be used, for example, for moving the patient's body part and/or for resisting forces by the patient.

The internal sensors 76 may measure one or more operating characteristics of the electromechanical machine 101 such as, for example, a force, a position, a speed, and/or a velocity. In some embodiments, the internal sensors 76 may include a position sensor configured to measure at least one of a linear motion or an angular motion of a body part of the patient. For example, an internal sensor 76 in the form of a position sensor may measure a distance that the patient is able to move a part of the electromechanical machine 101, where such distance may correspond to a range of motion that the patient's body part is able to achieve. In some embodiments, the internal sensors 76 may include a force sensor configured to measure a force applied by the patient. For example, an internal sensor 76 in the form of a force sensor may measure a force or weight the patient is able to apply, using a particular body part, to the electromechanical machine 101.

The system 10 generally illustrated in FIG. 3 also includes an ambulation sensor 82, which communicates with the server 30 via the local communication interface 68 of the patient interface 50. The ambulation sensor 82 may track and store a number of steps taken by the patient. In some embodiments, the ambulation sensor 82 may take the form of a wristband, wristwatch, or smart watch. In some embodiments, the ambulation sensor 82 may be integrated within a phone, such as a smartphone.

The system 10 generally illustrated in FIG. 3 also includes a goniometer 84 (e.g., AccuMotion®, AccuAngle®, etc.), which communicates with the server 30 via the local communication interface 68 of the patient interface 50. The goniometer 84 measures an angle of the patient's body part. For example, the goniometer 84 may measure the angle of flex of a patient's hip, knee, ankle, elbow, wrist, shoulder or other joints.

The system 10 generally illustrated in FIG. 3 also includes a pressure sensor 86, which communicates with the server 30 via the local communication interface 68 of the patient interface 50. The pressure sensor 86 measures an amount of pressure or weight applied by a body part of the patient. For example, pressure sensor 86 may measure an amount of force applied by a patient's hand or foot when pedaling a stationary bike, either pushing or pulling by the user.

The system 10 generally illustrated in FIG. 3 also includes a supervisory interface 90 which may be similar or identical to the clinician interface 20. In some embodiments, the supervisory interface 90 may have enhanced functionality beyond what is provided on the clinician interface 20. The supervisory interface 90 may be configured for use by a person having responsibility for the treatment plan, such as an orthopedic surgeon.

The system 10 generally illustrated in FIG. 3 also includes a reporting interface 92 which may be similar or identical to the clinician interface 20. In some embodiments, the reporting interface 92 may have less functionality from what is provided on the clinician interface 20. For example, the reporting interface 92 may not have the ability to modify a treatment plan. Such a reporting interface 92 may be used, for example, by a biller to determine the use of the system 10 for billing purposes. In another example, the reporting interface 92 may not have the ability to display patient identifiable information, presenting only pseudonymized data and/or anonymized data for certain data fields concerning a data subject and/or for certain data fields concerning a quasi-identifier of the data subject. Such a reporting interface 92 may be used, for example, by a researcher to determine various effects of a treatment plan on different patients.

The system 10 includes an assistant interface 94 a healthcare professional, such as those described herein, to remotely communicate with the patient interface 50 and/or the electromechanical machine 101. Such remote communications may enable the assistant to provide assistance or guidance to a patient using the system 10. More specifically, the assistant interface 94 is configured to communicate a telemedicine signal 96, 97, **98*a*, 98*b*, 99*a*, 99*b* with the patient interface 50 via a network connection such as, for example, via the first network 34 and/or the second network 58. The telemedicine signal 96, 97, 98*a*, 98*b*, 99*a*, 99*b* comprises one of an audio signal 96, an audiovisual signal 97, an interface control signal 98*a* for controlling a function of the patient interface 50, an interface monitor signal 98*b* for monitoring a status of the patient interface 50, an apparatus control signal 99*a* for changing an operating parameter of the electromechanical machine 101, and/or an apparatus monitor signal 99*b* for monitoring a status of the electromechanical machine 101. In some embodiments, each of the control signals 98*a*, 99*a* may be unidirectional, conveying commands from the assistant interface 94 to the patient interface 50. In some embodiments, in response to successfully receiving a control signal 98*a*, 99*a* and/or to communicate successful and/or unsuccessful implementation of the requested control action, an acknowledgement message may be sent from the patient interface 50 to the assistant interface 94. In some embodiments, each of the monitor signals 98*b*, 99*b* may be unidirectional, status-information commands from the patient interface 50 to the assistant interface 94. In some embodiments, an acknowledgement message may be sent from the assistant interface 94 to the patient interface 50 in response to successfully receiving one of the monitor signals 98*b*, 99*b***.

In some embodiments, the patient interface 50 may be configured as a pass-through for the apparatus control signals **99*a* and the apparatus monitor signals 99*b* between the electromechanical machine 101 and one or more other devices, such as the assistant interface 94 and/or the server 30. For example, the patient interface 50 may be configured to transmit an apparatus control signal 99*a* in response to an apparatus control signal 99*a* within the telemedicine signal 96, 97, 98*a*, 98*b*, 99*a*, 99*b* from the assistant interface 94**.

In some embodiments, the assistant interface 94 may be presented on a shared physical device as the clinician interface 20. For example, the clinician interface 20 may include one or more screens that implement the assistant interface 94. Alternatively or additionally, the clinician interface 20 may include additional hardware components, such as a video camera, a speaker, and/or a microphone, to implement aspects of the assistant interface 94.

In some embodiments, one or more portions of the telemedicine signal 96, 97, 98*a*, 98*b*, 99*a*, 99*b* may be generated from a prerecorded source (e.g., an audio recording, a video recording, or an animation) for presentation by the output device 54 of the patient interface 50. For example, a tutorial video may be streamed from the server 30 and presented upon the patient interface 50. Content from the prerecorded source may be requested by the patient via the patient interface 50. Alternatively, via a control on the assistant interface 94, the healthcare professional may cause content from the prerecorded source to be played on the patient interface 50.

The assistant interface 94 includes an assistant input device 22 and an assistant display 24, which may be collectively called an assistant user interface 22, 24. The assistant input device 22 may include one or more of a telephone, a keyboard, a mouse, a trackpad, or a touch screen, for example. Alternatively or additionally, the assistant input device 22 may include one or more microphones. In some embodiments, the one or more microphones may take the form of a telephone handset, headset, or wide-area microphone or microphones configured for the healthcare professional to speak to a patient via the patient interface 50. In some embodiments, assistant input device 22 may be configured to provide voice-based functionalities, with hardware and/or software configured to interpret spoken instructions by the assistant by using the one or more microphones. The assistant input device 22 may include functionality provided by or similar to existing voice-based assistants such as Siri by Apple, Alexa by Amazon, Google Assistant, or Bixby by Samsung. The assistant input device 22 may include other hardware and/or software components. The assistant input device 22 may include one or more general purpose devices and/or special-purpose devices.

The assistant display 24 may take one or more different forms including, for example, a computer monitor or display screen on a tablet, a smartphone, or a smart watch. The assistant display 24 may include other hardware and/or software components such as projectors, virtual reality capabilities, or augmented reality capabilities, etc. The assistant display 24 may incorporate various different visual, audio, or other presentation technologies. For example, the assistant display 24 may include a non-visual display, such as an audio signal, which may include spoken language and/or other sounds such as tones, chimes, melodies, and/or compositions, which may signal different conditions and/or directions. The assistant display 24 may comprise one or more different display screens presenting various data and/or interfaces or controls for use by the healthcare professional. The assistant display 24 may include graphics, which may be presented by a web-based interface and/or by a computer program or application (App.).

In some embodiments, the system 10 may provide computer translation of language from the assistant interface 94 to the patient interface 50 and/or vice-versa. The computer translation of language may include computer translation of spoken language and/or computer translation of text. Additionally or alternatively, the system 10 may provide voice recognition and/or spoken pronunciation of text. For example, the system 10 may convert spoken words to printed text and/or the system 10 may audibly speak language from printed text. The system 10 may be configured to recognize spoken words by any or all of the patient, the clinician, and/or the healthcare professional. In some embodiments, the system 10 may be configured to recognize and react to spoken requests or commands by the patient. For example, in response to a verbal command by the patient (which may be given in any one of several different languages), the system 10 may automatically initiate a telemedicine In some embodiments, the server 30 may generate aspects of the assistant display 24 for presentation by the assistant interface 94. For example, the server 30 may include a web server configured to generate the display screens for presentation upon the assistant display 24. For example, the artificial intelligence engine 11 may generate recommended treatment plans and/or excluded treatment plans for patients and generate the display screens including those recommended treatment plans and/or external treatment plans for presentation on the assistant display 24 of the assistant interface 94. In some embodiments, the assistant display 24 may be configured to present a virtualized desktop hosted by the server 30. In some embodiments, the server 30 may be configured to communicate with the assistant interface 94 via the first network 34. In some embodiments, the first network 34 may include a local area network (LAN), such as an Ethernet network. In some embodiments, the first network 34 may include the Internet, and communications between the server 30 and the assistant interface 94 may be secured via privacy enhancing technologies, such as, for example, by using encryption over a virtual private network (VPN). Alternatively or additionally, the server 30 may be configured to communicate with the assistant interface 94 via one or more networks independent of the first network 34 and/or other communication means, such as a direct wired or wireless communication channel. In some embodiments, the patient interface 50 and the electromechanical machine 101 may each operate from a patient location geographically separate from a location of the assistant interface 94. For example, the patient interface 50 and the electromechanical machine 101 may be used as part of an in-home rehabilitation system, which may be aided remotely by using the assistant interface 94 at a centralized location, such as a clinic or a call center.

In some embodiments, the assistant interface 94 may be one of several different terminals (e.g., computing devices) that may be grouped together, for example, in one or more call centers or at one or more clinicians' offices. In some embodiments, a plurality of assistant interfaces 94 may be distributed geographically. In some embodiments, a person may work as a healthcare professional remotely from any conventional office infrastructure. Such remote work may be performed, for example, where the assistant interface 94 takes the form of a computer and/or telephone. This remote work functionality may allow for work-from-home arrangements that may include part time and/or flexible work hours for a healthcare professional.

Figure 4:
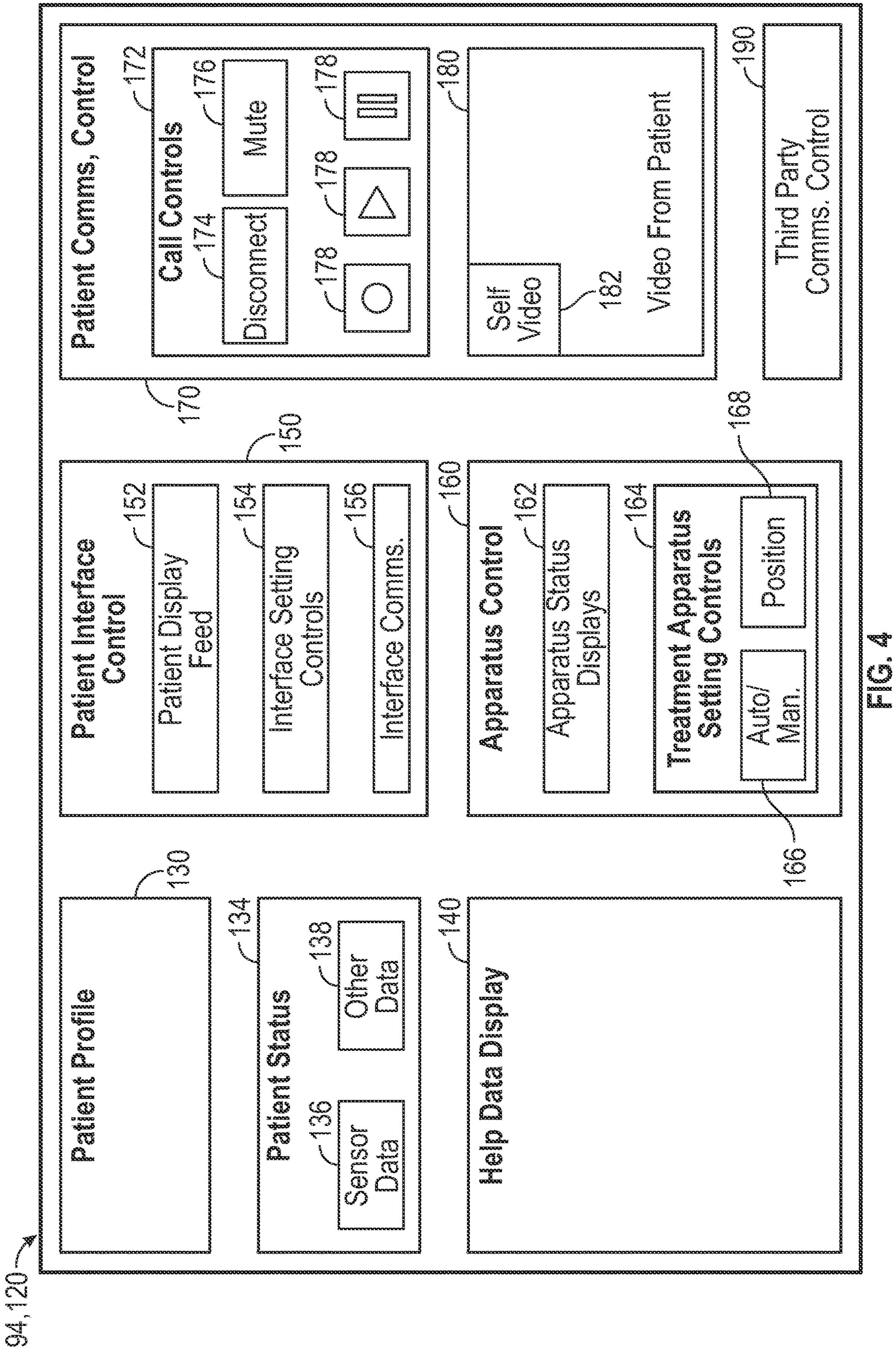
FIG. 4 generally illustrates an example embodiment of an overview display of an assistant interface according to the principles of the present disclosure.

FIG. 4 is an example embodiment of an overview display 120 of the assistant interface 94. Specifically, the overview display 120 presents several different controls and interfaces for the healthcare professional to remotely assist a patient with using the patient interface 50 and/or the electromechanical machine 101. This remote assistance functionality may also be called telemedicine or telehealth.

Figure 5:
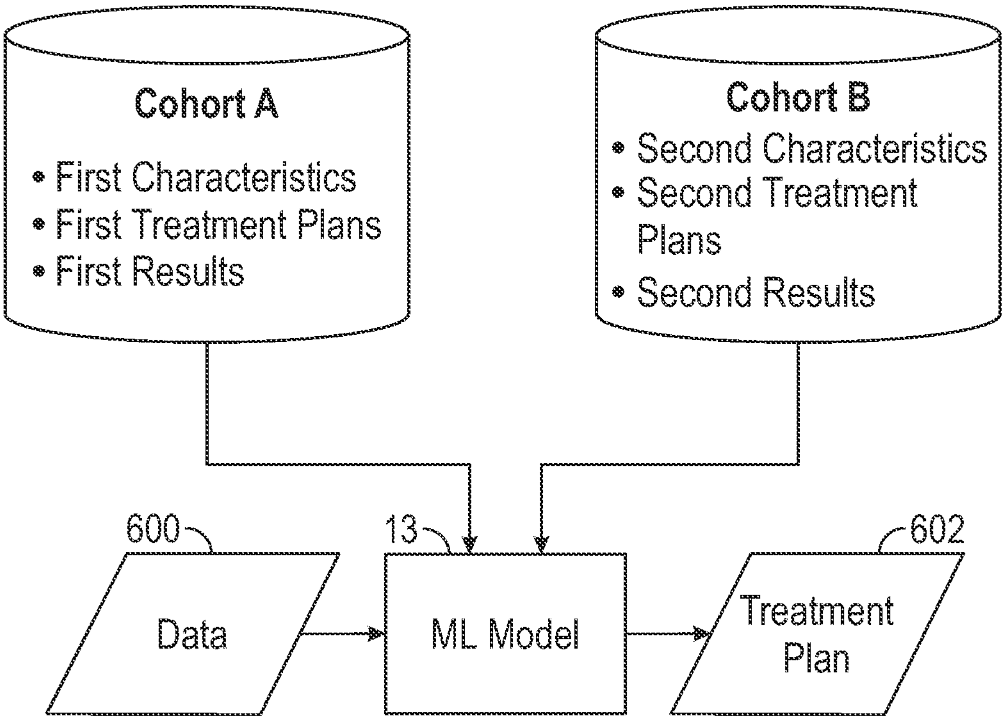
FIG. 5 generally illustrates an example block diagram of training a machine learning model to output, based on data pertaining to the patient, a treatment plan for the patient according to the principles of the present disclosure.

Specifically, the overview display 120 includes a patient profile display 130 presenting biographical information regarding a patient using the electromechanical machine 101. The patient profile display 130 may take the form of a portion or region of the overview display 120, as generally illustrated in FIG. 5, although the patient profile display 130 may take other forms, such as a separate screen or a popup window. In some embodiments, the patient profile display 130 may include a limited subset of the patient's biographical information. More specifically, the data presented upon the patient profile display 130 may depend upon the healthcare professional's need for that information. For example, a healthcare professional that is assisting the patient with a medical issue may be provided with medical history information regarding the patient, whereas a technician troubleshooting an issue with the electromechanical machine 101 may be provided with a much more limited set of information regarding the patient. The technician, for example, may be given only the patient's name. The patient profile display 130 may include pseudonym zed data and/or anonymized data or use any privacy enhancing technology to prevent confidential patient data from being communicated in a way that could violate patient confidentiality requirements. Such privacy enhancing technologies may enable compliance with laws, regulations, or other rules of governance such as, but not limited to, the Health Insurance Portability and Accountability Act (HIPAA), or the General Data Protection Regulation (GDPR), wherein the patient may be deemed a "data subject".

In some embodiments, the patient profile display 130 may present information regarding the treatment plan for the patient to follow in using the electromechanical machine 101. Such treatment plan information may be limited to a healthcare professional. For example, a healthcare professional assisting the patient with an issue regarding the treatment regimen may be provided with treatment plan information, whereas a technician troubleshooting an issue with the electromechanical machine 101 may not be provided with any information regarding the patient's treatment plan.

In some embodiments, one or more recommended treatment plans and/or excluded treatment plans may be presented in the patient profile display 130 to the healthcare professional. The one or more recommended treatment plans and/or excluded treatment plans may be generated by the artificial intelligence engine 11 of the server 30 and received from the server 30 in real-time during a telemedicine or telehealth session. An example of presenting the one or more recommended treatment plans and/or ruled-out treatment plans is described below with reference to FIG. 6.

The example overview display 120 generally illustrated in FIG. 4 also includes a patient status display 134 presenting status information regarding a patient using the electromechanical machine 101. The patient status display 134 may take the form of a portion or region of the overview display 120, as generally illustrated in FIG. 4, although the patient status display 134 may take other forms, such as a separate screen or a popup window. The patient status display 134 includes sensor data 136 from one or more of the external sensors 82, 84, 86, and/or from one or more internal sensors 76 of the electromechanical machine 101. In some embodiments, the patient status display 134 may include sensor data from one or more sensors of one or more wearable devices worn by the patient or spaced from the patient (i.e., the remote sensing devices 108) while using the electromechanical machine 101. The one or more wearable devices may include a watch, a bracelet, a necklace, a chest strap, vest and the like, such as any device adhered to the skin or body (e.g., ECG sensor). The one or more wearable devices may be configured to monitor a heartrate, a temperature, a blood pressure, one or more vital signs, and the like of the patient while the patient is using the electromechanical machine 101. The one or more remote sensing devices 108 may be configured to interact with or communicate with the wearable devices in order to more particularly identify attributes of the user. In some embodiments, the patient status display 134 may present other data 138 regarding the patient, such as last reported pain level, or progress within a treatment plan.

User access controls may be used to limit access, including what data is available to be viewed and/or modified, on any or all of the user interfaces 20, 50, 90, 92, 94 of the system 10. In some embodiments, user access controls may be employed to control what information is available to any given person using the system 10. For example, data presented on the assistant interface 94 may be controlled by user access controls, with permissions set depending on the healthcare professional/user's need for and/or qualifications to view that information.

The example overview display 120 generally illustrated in FIG. 4 also includes a help data display 140 presenting information for the healthcare professional to use in assisting the patient. The help data display 140 may take the form of a portion or region of the overview display 120, as generally illustrated in FIG. 4. The help data display 140 may take other forms, such as a separate screen or a popup window. The help data display 140 may include, for example, presenting answers to frequently asked questions regarding use of the patient interface 50 and/or the electromechanical machine 101. The help data display 140 may also include research data or best practices. In some embodiments, the help data display 140 may present scripts for answers or explanations in response to patient questions. In some embodiments, the help data display 140 may present flow charts or walk-throughs for the healthcare professional to use in determining a root cause and/or solution to a patient's problem. In some embodiments, the assistant interface 94 may present two or more help data displays 140, which may be the same or different, for simultaneous presentation of help data for use by the healthcare professional. for example, a first help data display may be used to present a troubleshooting flowchart to determine the source of a patient's problem, and a second help data display may present script information for the healthcare professional to read to the patient, such information to preferably include directions for the patient to perform some action, which may help to narrow down or solve the problem. In some embodiments, based upon inputs to the troubleshooting flowchart in the first help data display, the second help data display may automatically populate with script information.

The example overview display 120 generally illustrated in FIG. 4 also includes a patient interface control 150 presenting information regarding the patient interface 50, and/or to modify one or more settings of the patient interface 50. The patient interface control 150 may take the form of a portion or region of the overview display 120, as shown in FIG. 4. The patient interface control 150 may take other forms, such as a separate screen or a popup window. The patient interface control 150 may present information communicated to the assistant interface 94 via one or more of the interface monitor signals 98*b*. As generally illustrated in FIG. 4, the patient interface control 150 includes a display feed 152 of the display presented by the patient interface 50. In some embodiments, the display feed 152 may include a live copy of the display screen currently being presented to the patient by the patient interface 50. In other words, the display feed 152 may present an image of what is presented on a display screen of the patient interface 50. In some embodiments, the display feed 152 may include abbreviated information regarding the display screen currently being presented by the patient interface 50, such as a screen name or a screen number. The patient interface control 150 may include a patient interface setting control 154 for the healthcare professional to adjust or to control one or more settings or aspects of the patient interface 50. In some embodiments, the patient interface setting control 154 may cause the assistant interface 94 to generate and/or to transmit an interface control signal 98 for controlling a function or a setting of the patient interface 50.

In some embodiments, the patient interface setting control 154 may include collaborative browsing or co-browsing capability for the healthcare professional to remotely view and/or control the patient interface 50. For example, the patient interface setting control 154 may enable the healthcare professional to remotely enter text to one or more text entry fields on the patient interface 50 and/or to remotely control a cursor on the patient interface 50 using a mouse or touchscreen of the assistant interface 94.

In some embodiments, using the patient interface 50, the patient interface setting control 154 may allow the healthcare professional to change a setting that cannot be changed by the patient. For example, the patient interface 50 may be precluded from accessing a language setting to prevent a patient from inadvertently switching, on the patient interface 50, the language used for the displays, whereas the patient interface setting control 154 may enable the healthcare professional to change the language setting of the patient interface 50. In another example, the patient interface 50 may not be able to change a font size setting to a smaller size in order to prevent a patient from inadvertently switching the font size used for the displays on the patient interface 50 such that the display would become illegible to the patient, whereas the patient interface setting control 154 may provide for the healthcare professional to change the font size setting of the patient interface 50.

The example overview display 120 generally illustrated in FIG. 4 also includes an interface communications display 156 showing the status of communications between the patient interface 50 and one or more other devices 70, 82, 84, such as the electromechanical machine 101, the ambulation sensor 82, and/or the goniometer 84. The interface communications display 156 may take the form of a portion or region of the overview display 120, as generally illustrated in FIG. 4. The interface communications display 156 may take other forms, such as a separate screen or a popup window. The interface communications display 156 may include controls for the healthcare professional to remotely modify communications with one or more of the other devices 70, 82, 84. For example, the healthcare professional may remotely command the patient interface 50 to reset communications with one of the other devices 70, 82, 84, or to establish communications with a new one of the other devices 70, 82, 84. This functionality may be used, for example, where the patient has a problem with one of the other devices 70, 82, 84, or where the patient receives a new or a replacement one of the other devices 70, 82, 84.

The example overview display 120 generally illustrated in FIG. 4 also includes an apparatus control 160 for the healthcare professional to view and/or to control information regarding the electromechanical machine 101. The apparatus control 160 may take the form of a portion or region of the overview display 120, as generally illustrated in FIG. 4. The apparatus control 160 may take other forms, such as a separate screen or a popup window. The apparatus control 160 may include an apparatus status display 162 with information regarding the current status of the apparatus. The apparatus status display 162 may present information communicated to the assistant interface 94 via one or more of the apparatus monitor signals 99*b*. The apparatus status display 162 may indicate whether the electromechanical machine 101 is currently communicating with the patient interface 50. The apparatus status display 162 may present other current and/or historical information regarding the status of the electromechanical machine 101.

The apparatus control 160 may include an apparatus setting control 164 for the healthcare professional to adjust or control one or more aspects of the electromechanical machine 101. The apparatus setting control 164 may cause the assistant interface 94 to generate and/or to transmit an apparatus control signal 99 (e.g. which may be referred to as treatment plan input) for changing an operating parameter and/or one or more characteristics of the electromechanical machine 101, (e.g., a pedal radius setting, a resistance setting, a target RPM, other suitable characteristics of the treatment device 70, or a combination thereof). The apparatus setting control 164 may include a mode button 166 and a position control 168, which may be used in conjunction for the healthcare professional to place an actuator 78 of the electromechanical machine 101 in a manual mode, after which a setting, such as a position or a speed of the actuator 78, can be changed using the position control 168. The mode button 166 may provide for a setting, such as a position, to be toggled between automatic and manual modes. In some embodiments, one or more settings may be adjustable at any time, and without having an associated auto/manual mode. In some embodiments, the healthcare professional may change an operating parameter of the electromechanical machine 101, such as a pedal radius setting, while the patient is actively using the electromechanical machine 101. Such "on the fly" adjustment may or may not be available to the patient using the patient interface 50. In some embodiments, the apparatus setting control 164 may allow the healthcare professional to change a setting that cannot be changed by the patient using the patient interface 50. For example, the patient interface 50 may be precluded from changing a preconfigured setting, such as a height or a tilt setting of the electromechanical machine 101, whereas the apparatus setting control 164 may provide for the healthcare professional to change the height or tilt setting of the electromechanical machine 101.

The example overview display 120 generally illustrated in FIG. 4 also includes a patient communications control 170 for controlling an audio or an audiovisual communications session with the patient interface 50. The communications session with the patient interface 50 may comprise a live feed from the assistant interface 94 for presentation by the output device of the patient interface 50. The live feed may take the form of an audio feed and/or a video feed. In some embodiments, the patient interface 50 may be configured to provide two-way audio or audiovisual communications with a person using the assistant interface 94. Specifically, the communications session with the patient interface 50 may include bidirectional (two-way) video or audiovisual feeds, with each of the patient interface 50 and the assistant interface 94 presenting video of the other one. In some embodiments, the patient interface 50 may present video from the assistant interface 94, while the assistant interface 94 presents only audio or the assistant interface 94 presents no live audio or visual signal from the patient interface 50. In some embodiments, the assistant interface 94 may present video from the patient interface 50, while the patient interface 50 presents only audio or the patient interface 50 presents no live audio or visual signal from the assistant interface 94.

In some embodiments, the audio or an audiovisual communications session with the patient interface 50 may take place, at least in part, while the patient is performing the rehabilitation regimen upon the body part. The patient communications control 170 may take the form of a portion or region of the overview display 120, as shown in FIG. 4. The patient communications control 170 may take other forms, such as a separate screen or a popup window. The audio and/or audiovisual communications may be processed and/or directed by the assistant interface 94 and/or by another device or devices, such as a telephone system, or a videoconferencing system used by the healthcare professional while the healthcare professional uses the assistant interface 94. Alternatively or additionally, the audio and/or audiovisual communications may include communications with a third party. For example, the system 10 may enable the healthcare professional to initiate a 3-way conversation regarding use of a particular piece of hardware or software, with the patient and a subject matter expert, such as a medical professional or a specialist. The example patient communications control 170 generally illustrated in FIG. 4 includes call controls 172 for the healthcare professional to use in managing various aspects of the audio or audiovisual communications with the patient. The call controls 172 include a disconnect button 174 for the healthcare professional to end the audio or audiovisual communications session. The call controls 172 also include a mute button 176 to temporarily silence an audio or audiovisual signal from the assistant interface 94. In some embodiments, the call controls 172 may include other features, such as a hold button (not shown). The call controls 172 also include one or more record/playback controls 178, such as record, play, and pause buttons to control, with the patient interface 50, recording and/or playback of audio and/or video from the teleconference session (e.g., which may be referred to herein as the virtual conference room). The call controls 172 also include a video feed display 180 for presenting still and/or video images from the patient interface 94, and a self-video display 182 showing the current image of the healthcare professional using the assistant interface 94. The self-video display 182 may be presented as a picture-in-picture format, within a section of the video feed display 180, as generally illustrated in FIG. 4. Alternatively or additionally, the self-video display 182 may be presented separately and/or independently from the video feed display 180.

The example overview display 120 generally illustrated in FIG. 4 also includes a third party communications control 190 for use in conducting audio and/or audiovisual communications with a third party. The third-party communications control 190 may take the form of a portion or region of the overview display 120, as generally illustrated in FIG. 5. The third-party communications control 190 may take other forms, such as a display on a separate screen or a popup window. The third-party communications control 190 may include one or more controls, such as a contact list and/or buttons or controls to contact a third party regarding use of a particular piece of hardware or software, e.g., a subject matter expert, such as a healthcare professional or a specialist. The third-party communications control 190 may include conference calling capability for the third party to simultaneously communicate with both the healthcare professional via the assistant interface 94, and with the patient via the patient interface 50. For example, the system 10 may provide for the healthcare professional to initiate a 3-way conversation with the patient and the third party.

FIG. 5 generally illustrates an example block diagram of training a machine learning model 13 to output, based on data 600 pertaining to the patient, a treatment plan 602 for the patient according to the present disclosure. Data pertaining to other patients may be received by the server 30. The other patients may have used various treatment apparatuses to perform treatment plans. The data may include characteristics of the other patients, the details of the treatment plans performed by the other patients, and/or the results of performing the treatment plans (e.g., a percentage of recovery of a portion of the patients' bodies, an amount of recovery of a portion of the patients' bodies, an amount or percentage of increase or decrease in muscle strength of a portion of patients' bodies, an amount or percentage of increase or decrease in range of motion of a portion of patients' bodies, etc.).

The data related to the treatment plans may include prescribed exercises that were implemented by the electromechanical machines 101 used by the users. The prescribed exercises may be associated with certain motion profiles that enabled the prescribed exercises to be performed using the electromechanical machines 101. The data may include correlations, associations, and/or relations between the treatment plans (e.g., motion profiles of the prescribed exercises) and the results experienced by the users.

The training data used to train the machine learning model 13 may be preprocessed prior to being fed to the machine learning model 13. Preprocessing may refer to formatting the data. In some embodiments, the formatting may include transforming the data into a treatment machine description language, which may refer to a canonical data format that includes tag and value pairs and/or one or more grammar attributes. Due to its uniform format, the treatment machine description language may enable more efficient training of the machine learning model 13 and faster execution when the trained machine learning model 13 is subsequently run. The preprocessing may select characteristics and/or attributes of the data to be used for matching the data to desired outputs. The preprocessing may also include normalizing the data, eliminating duplicates of the data, making error corrections to the data, and the like. In some embodiments, the preprocessing may format the data received from any suitable source, such as extensible markup language (XML) files, databases, database collection objects (tables), flat files, comma separated values (CSV) files and other delimited files, text files, spreadsheet files, etc.

As depicted, the data has been assigned to different cohorts. Cohort A includes data for patients having similar first characteristics, first treatment plans, and first results. Cohort B includes data for patients having similar second characteristics, second treatment plans, and second results. For example, cohort A may include first characteristics of patients in their twenties without any medical conditions who underwent surgery for a broken limb; their treatment plans may include a certain treatment protocol (e.g., use the electromechanical machine 101 for 30 minutes 5 times a week for 3 weeks, wherein values for the properties, configurations, and/or settings of the electromechanical machine 101 are set to X (where X is a numerical value) for the first two weeks and to Y (where Y is a numerical value) for the last week).

Cohort A and cohort B may be included in a training dataset used to train the machine learning model 13. The machine learning model 13 may be trained to match a pattern between characteristics for each cohort and to output the treatment plan or a variety of possible treatment plans for selection by a healthcare provider. The output treatment plan may include one or more prescribed exercises with associated motion profiles to be implemented by the electromechanical machine 101. Accordingly, when the data 600 for a new patient is input into the trained machine learning model 13, the trained machine learning model 13 may match the characteristics included in the data 600 with characteristics in either cohort A or cohort B and output the appropriate treatment plan or plans 602. In some embodiments, the machine learning model 13 may be trained to output one or more excluded treatment plans that should not be performed by the new patient.

In some embodiments, the machine learning models 13 may be trained to output a virtual model of a desired electromechanical machine 101 capable of performing a prescribed exercise associated with achieving a desired goal. Accordingly, the training data may include inputs related to desired goals and treatment plans and outputs related to the virtual model of the desired electromechanical machine 101. The output may be in the treatment machine description language format. The virtual model may include one or more graphical representations of components used to enable performing the prescribed exercise. The graphical representations may be associated with one or more identifiers of the components used to enable the electromechanical machine 101 to perform the prescribed exercise.

Figure 6:
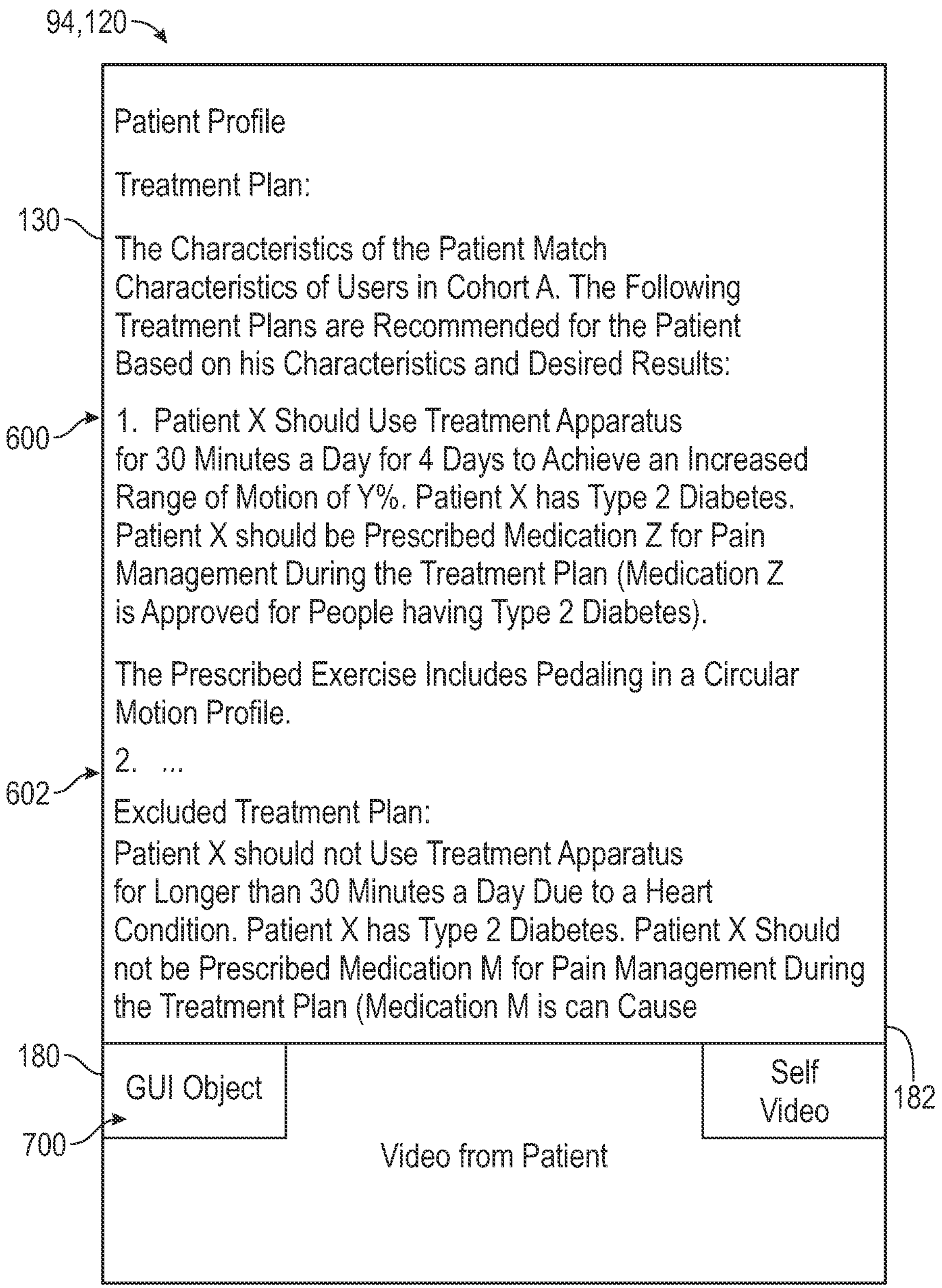
FIG. 6 generally illustrates an embodiment of an overview display of the assistant interface presenting in real-time during a telemedicine session recommended treatment plans according to the principles of the present disclosure.

FIG. 6 generally illustrates an embodiment of an overview display 120 of the assistant interface 94 presenting recommended treatment plans and excluded treatment plans in real-time during a telemedicine session according to the present disclosure. As depicted, the overview display 120 just includes sections for the patient profile 130 and the video feed display 180, including the self-video display 182. Any suitable configuration of controls and interfaces of the overview display 120 described with reference to FIG. 4 may be presented in addition to or instead of the patient profile 130, the video feed display 180, and the self-video display 182.

The healthcare professional using the assistant interface 94 (e.g., computing device) during the telemedicine session may be presented in the self-video 182 in a portion of the overview display 120 (e.g., user interface presented on a display screen 24 of the assistant interface 94) that also presents a video from the patient in the video feed display 180. Further, the video feed display 180 may also include a graphical user interface (GUI) object 700 (e.g., a button) that enables the healthcare professional to share, in real-time or near real-time during the telemedicine session, the recommended treatment plans and/or the excluded treatment plans with the patient on the patient interface 50. The healthcare professional may select the GUI object 700 to share the recommended treatment plans and/or the excluded treatment plans. As depicted, another portion of the overview display 120 includes the patient profile display 130.

The patient profile display 130 is presenting two example recommended treatment plans 600 and one example excluded treatment plan 602. As described herein, the treatment plans may be recommended in view of characteristics of the patient being treated. To generate the recommended treatment plans 600 the patient should follow to achieve a desired result, a pattern between the characteristics of the patient being treated and a cohort of other people who have used the electromechanical machine 101 to perform a treatment plan may be matched by one or more machine learning models 13 of the artificial intelligence engine 11. Each of the recommended treatment plans may be generated based on different desired results.

For example, as depicted, the patient profile display 130 presents "The characteristics of the patient match characteristics of users in Cohort A. The following treatment plans are recommended for the patient based on his characteristics and desired results." Then, the patient profile display 130 presents recommended treatment plans from cohort A, and each treatment plan provides different results.

As depicted, treatment plan "A" indicates "Patient X should use treatment apparatus for 30 minutes a day for 4 days to achieve an increased range of motion of Y %; Patient X has Type 2 Diabetes; and Patient X should be prescribed medication Z for pain management during the treatment plan (medication Z is approved for people having Type 2 Diabetes; The prescribed exercise includes pedaling in a circular motion profile)." Accordingly, the treatment plan generated achieves increasing the range of motion of Y %. As may be appreciated, the treatment plan also includes a recommended medication (e.g., medication Z) to prescribe to the patient to manage pain in view of a known medical disease (e.g., Type 2 Diabetes) of the patient. That is, the recommended patient medication not only does not conflict with the medical condition of the patient but thereby improves the probability of a superior patient outcome. The treatment plan also includes a prescribed exercise for the treatment apparatus that involves pedaling in a circular motion profile. This specific example and all such examples elsewhere herein are not intended to limit in any way the generated treatment plan from recommending multiple medications, or from handling the acknowledgement, view, diagnosis and/or treatment of comorbid conditions or diseases.

Recommended treatment plan "B" may specify, based on a different desired result of the treatment plan, a different treatment plan including a different treatment protocol for an electromechanical machine 101, a different medication regimen, etc.

As depicted, the patient profile display 130 may also present the excluded treatment plans 602. These types of treatment plans are shown to the healthcare professional using the assistant interface 94 to alert the healthcare professional not to recommend certain portions of a treatment plan to the patient. For example, the excluded treatment plan could specify the following: "Patient X should not use treatment apparatus for longer than 30 minutes a day due to a heart condition; Patient X has Type 2 Diabetes; and Patient X should not be prescribed medication M for pain management during the treatment plan (in this scenario, medication M can cause complications for people having Type 2 Diabetes). Specifically, the excluded treatment plan points out a limitation of a treatment protocol where, due to a heart condition, Patient X should not exercise for more than 30 minutes a day. The ruled-out treatment plan also points out that Patient X should not be prescribed medication M because it conflicts with the medical condition Type 2 Diabetes.

The healthcare professional may select the treatment plan for the patient on the overview display 120. For example, the healthcare professional may use an input peripheral (e.g., mouse, touchscreen, microphone, keyboard, etc.) to select from the treatment plans 600 for the patient. In some embodiments, during the telemedicine session, the healthcare professional may discuss the pros and cons of the recommended treatment plans 600 with the patient.

In any event, the healthcare professional may select the treatment plan for the patient to follow to achieve the desired result. The selected treatment plan may be transmitted to the patient interface 50 for presentation. The patient may view the selected treatment plan on the patient interface 50. In some embodiments, the healthcare professional and the patient may discuss during the telemedicine session the details (e.g., treatment protocol using treatment apparatus 70, diet regimen, medication regimen, etc.) in real-time or in near real-time. In some embodiments, the server 30 may control, based on the selected treatment plan and during the telemedicine session, the electromechanical machine 101 as the user uses the electromechanical machine 101.

Figure 7:
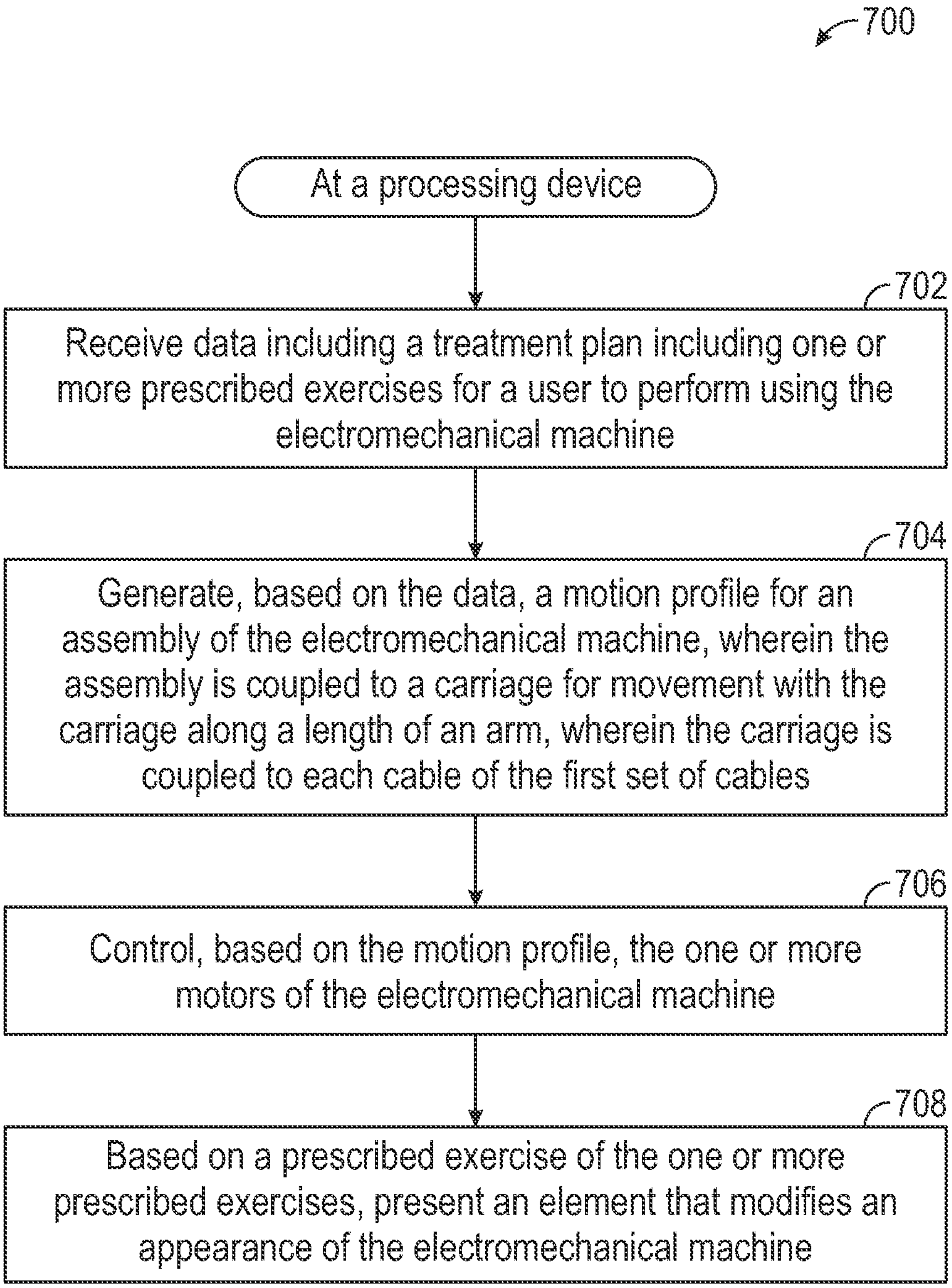
FIG. 7 is a flow diagram generally illustrating a method for generating a motion profile for an assembly of an electromechanical machine according to the principles of the present disclosure.

FIG. 7 is a flow diagram generally illustrating a method 700 for generating a motion profile for an assembly of an electromechanical machine according to the principles of the present disclosure. The method 700 is performed by processing logic that may include hardware (circuitry, dedicated logic, etc.), software, or a combination of both. The method 700 and/or each of its individual functions, routines, subroutines, operations, or methods (e.g., object-oriented programming) may be performed by one or more processors of a computing device (e.g., any component of FIG. 3, such as server 30 executing the artificial intelligence engine 11). In some embodiments, the method 700 may be performed by a single processing thread. Alternatively, the method 700 may be performed by two or more processing threads, each thread implementing one or more individual functions, routines, subroutines, object-oriented methods, or operations of the methods.

For simplicity of explanation, the method 700 is depicted and described as a series of operations. However, operations in accordance with this disclosure can occur in various orders and/or concurrently, and/or with other operations not presented and described herein. For example, the operations depicted in the method 700 may occur in combination with any other operation of any other method disclosed herein. Furthermore, not all illustrated operations may be required to implement the method 700 in accordance with the disclosed subject matter. In addition, those skilled in the art will understand and appreciate that the method 700 could alternatively be represented as a series of interrelated states via a state-based or event-based diagram.

In some embodiments, one or more machine learning models 13 may be generated and trained by the artificial intelligence engine 11 and/or the training engine 9 to perform one or more of the operations of the method 700. For example, to perform the one or more operations, the processing device may execute the one or more machine learning models 13. In some embodiments, the one or more machine learning models 13 may be iteratively retrained to select different features capable of enabling optimization of output. The features that may be modified may include a number of nodes included in each layer of the machine learning models 13, an objective function executed at each node, a number of layers, various weights associated with outputs of each node, and the like.

In some embodiments, as described herein, the electromechanical machine 101 may include one or more motors mounted to a body and spaced apart from each other, and a first set of cables, each coupled to a respective one of the motors. The electromechanical machine 101 may include an assembly coupled to a carriage for movement with the carriage along a length of an arm. The carriage may be coupled to each cable of the first set of cables. The assembly may include a pedal assembly and the pedal assembly is rotatably coupled to the carriage. In some embodiments, the assembly may include a handlebar assembly, a row assembly, a pedal assembly, a climbable assembly, a step assembly, a paddle assembly, a brace assembly, a lift assembly, a push assembly, a balance assembly, or some combination thereof.

Further, a processing device may be communicatively coupled to the one or more motors to transmit control signals to the one or more motors to control an operating parameter (e.g., speed, revolutions per minute, torque, etc.) of the motors. The processing device may execute computer instructions to implement a control system. In some embodiments, the processing device may be disposed in a computing device separate from the electromechanical machine 101, or the processing device may be disposed in the electromechanical machine 101.

At 702, the processing device may receive data including a treatment plan. The treatment plan may include one or more prescribed exercises for a user to perform using the electromechanical machine 101.

At 704, the processing device may generate, based on the data, a motion profile for an assembly of the electromechanical machine 101. The assembly may be coupled to a carriage for movement with the carriage along a length of an arm. The carriage may be coupled to each cable of the first set of cables. In some embodiments, the processing device may generate, using the artificial intelligence engine 11, a machine learning model 13 trained to generate the motion profile for the assembly.

In some embodiments, the processing device may execute a machine learning model 13 trained to control one or more spools of the first set of cables, one or more speeds of the one or more motors, one or more resistances provided by the one or more motors, one or more ranges of motion of the carriage and assembly, or some combination thereof. The spools may refer to one or more cylindrical-shaped objects (e.g., or any one or more suitably-shaped objects) that are configured to enable cables to wind around.

In some embodiments, using the electromechanical machine 101, the processing device may execute a transformation function to implement a desired virtual apparatus model. The transformation function may refer to a mathematical function that modifies another mathematical function to cause a graph associated with the other mathematical function to be modified. The transformation function may result in one or more coordinates being mapped to an n-dimensional plane or domain. The resulting graph that is made up of the coordinates may refer to a motion profile. The motion profile may include a line or a geometrical shape (e.g., circle, ellipse, rectangle, square, etc.).

The desired virtual apparatus model may refer to a virtual representation of a desired electromechanical machine 101. The desired virtual apparatus may implement one or more settings, parameters, operations, components, attributes, motion profiles, etc. For example, to simulate an elliptical machine, the desired virtual apparatus may implement a motion profile that causes the carriage and assembly to move in any type of motion, such as elliptical motion. To cause the electromechanical machine 101 to operate like the desired virtual apparatus, the desired virtual apparatus and/or one or more of its settings, parameters, operations, components, attributes, motion profiles, etc. may be transmitted to the electromechanical machine 101.

In some embodiments, a machine learning model 13 may be trained, based on identifying correlations between pedal motion and user impact, to determine a motion profile. For example, the user impact may refer to a result associated with using the motion profile to perform a treatment plan on the electromechanical machine 101. In some embodiments, the processing device may transform the motion profile of the carriage and/or assembly based on certain criteria, such as characteristics related to one or more muscle groups, user attributes (e.g., height, demographic, weight, age, etc.), one or more desired goals, or some combination thereof. For example, a motion profile correlated with achieving a certain result may be selected, determined, and/or generated if the user and/or healthcare professional desires the user to achieve that certain result by using the electromechanical machine 101.

At 706, the processing device may control, based on the motion profile, the one or more motors of the electromechanical machine 101.

At 708, based on a prescribed exercise of the one or more prescribed exercises, the processing device may present an element that modifies an appearance of the electromechanical machine 101. For example, a headset may be configured to present, based on a prescribed exercise of the one or more prescribed exercises, a virtual reality element that modifies an appearance of the electromechanical machine 101 in the headset. The virtual reality element may be a video, an image, an audible noise, a graphic, a setting, or the like. In another example, a display may be configured to present, based on a prescribed exercise of the one or more prescribed exercises, an augmented reality element that modifies on the display an appearance of the electromechanical machine 101. The augmented reality element may be a video, an image, a noise configured to be audible, a graphic, a setting, or the like.

Figure 8:
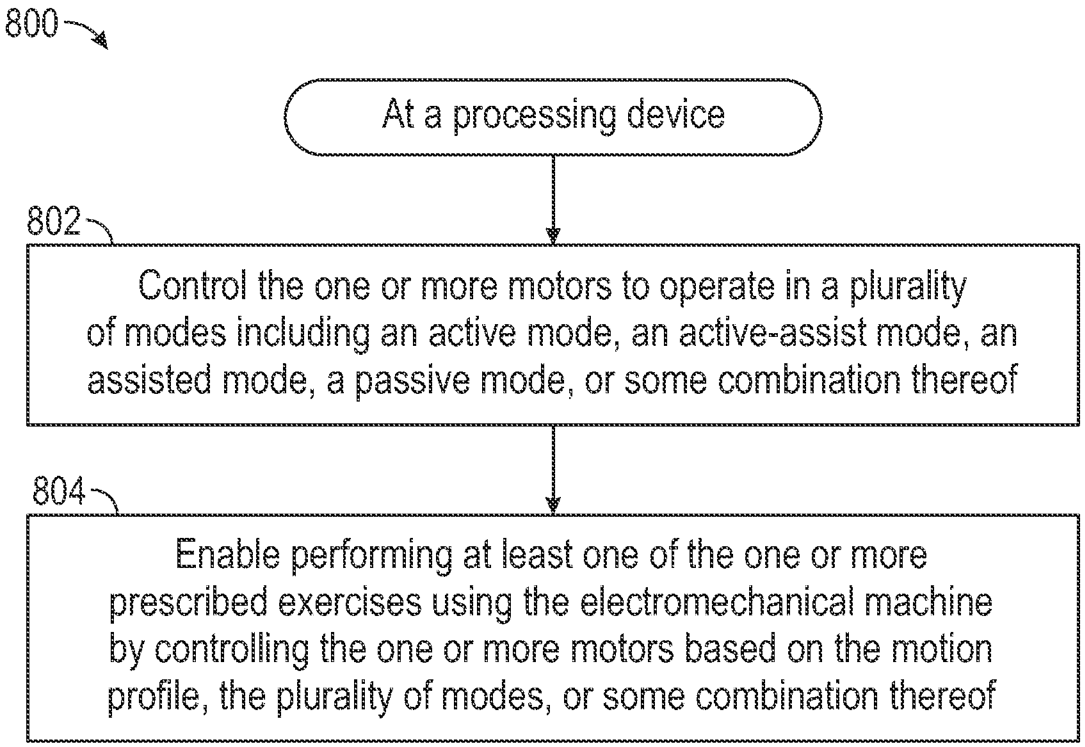
FIG. 8 is a flow diagram generally illustrating a method for controlling the electromechanical machine in one or more modes according to the principles of the present disclosure.

FIG. 8 is a flow diagram generally illustrating a method 800 for controlling the electromechanical machine in one or more modes according to the principles of the present disclosure. Method 800 includes operations performed by processors of a computing device (e.g., any component of FIG. 3, such as server 30 executing the artificial intelligence engine 11). In some embodiments, one or more operations of the method 800 may be implemented in computer instructions stored on a memory device and executed by a processing device. The method 800 may be performed in the same or a similar manner as described above in regard to method 700. The operations of the method 800 may be performed in some combination with any of the operations of any of the methods described herein.

In some embodiments, to perform one or more of the operations of the method 800, one or more machine learning models 13 may be generated and trained by the artificial intelligence engine 11 and/or the training engine 9. For example, to perform the one or more operations, the processing device may execute the one or more machine learning models 13. In some embodiments, the one or more machine learning models 13 may be iteratively retrained to select different features capable of enabling optimization of output. The features that may be modified may include a number (i.e., quantity) of nodes included in each layer of the machine learning models 13, an objective function executed at each node, a number (i.e., quantity) of layers, various weights associated with outputs of each node, and the like.

At 802, the processing device may control the one or more motors to operate in a plurality of modes including an active mode, an active-assist mode, an assisted mode, a passive mode, or some combination thereof. While operating the electromechanical machine in the various modes, the control system may use information received from measuring devices (e.g., sensors) to adjust parameters (e.g., reduce resistance provided by motors, increase resistance provided by the motors, increase/decrease speed of the motors, etc.). The control system may receive the information from the monitoring devices, aggregate the information, make determinations using the information, and/or transmit the information to a server for storage. The server may maintain the information that is related to each user.

In some embodiments, the measuring devices may include pressure sensors and/or force sensors located in the pedal assemblies. These sensors may be configured to measure an amount of force exerted on the sensors and transmit the measurement to a processing device. In some embodiments, the measuring devices may include one or more goniometers, wearable sensors, cameras, accelerometers, strain gauges, light sensors, biosensors, pressure sensors, proximity sensors, haptic sensors, piezoelectric sensors, optical sensors, temperature sensors, electrical sensors, mechanical sensors, chemical sensors, electromechanical sensors, electrochemical sensors, or mechanicochemical sensors. In some embodiments, the measuring device may be in pill form and may be swallowed by the user to monitor the user's core temperature, among other things. In some embodiments, the measuring device may be injected into the user via the skin of the user. In some embodiments, the measuring device may be implanted in a portion of the user's body. In some embodiments, any suitable measuring device configured to obtain any suitable characteristic, measurement, attribute, etc. of the user, of the electromechanical machine 101, of the exercise, and of the like may be used.

The passive mode may refer to the one or more motors independently driving the carriage and/or the assembly. In the passive mode, the motors may be the only source of driving force on the carriage and/or couplings. That is, the user may engage the 110 with their hands or their feet and the motors may rotate the carriage and/or assembly for the user. This may enable moving the affected body part and stretching the affected body part without the user exerting excessive force.

The active-assisted mode may refer to the motors receiving measurements of revolutions per minute of the one or more carriages and/or assemblies, and a processing device may cause the motors to drive the one or more carriage and/or assembly when the measured revolutions per minute satisfy a threshold condition. The threshold condition may be configurable by the user and/or the healthcare professional. The motors may be powered off while the user provides the driving force to the carriage and/or assembly as long as the revolutions per minute are above a revolutions per minute threshold and the threshold condition is not satisfied. When the revolutions per minute are less than the revolutions per minute threshold then the threshold condition is satisfied and the motors may be controlled to drive the carriage and/or assembly to maintain the revolutions per minute threshold.

The resistive mode may refer to the motors providing resistance to rotation of the one or more carriages and/or assemblies. By causing the muscle to exert force to move the pedals against the resistance provided by the motors, the resistive mode may increase the strength of the body part being rehabilitated.

The active mode may refer to the motors powering off such that no driving force assistance is provided to the carriage and/or assembly. Instead, in this mode, the user, using their hands or feet, for example, provides the sole driving force of the carriage and/or assembly.

During one or more of the modes, each of the assemblies may measure force exerted by a part of the body of the user on the assemblies. For example, the assemblies may each contain any suitable sensor (e.g., strain gauge load cell, piezoelectric crystal, hydraulic load cell, etc.) for measuring force exerted on the assembly. Further, the assemblies may each contain any suitable sensor for detecting whether the user's body part separates from contact. In some embodiments, the measured force may be used to detect whether the body part has separated from the assemblies. The force detected may be transmitted via the network interface card of any of the assemblies to the control system.

At 804, by controlling the one or more motors based on the motion profile, the plurality of modes, or some combination thereof, the processing device may enable performing at least one of the one or more prescribed exercises by using the electromechanical machine 101. The processing device may be configured to transmit control instructions or control signals to the motors to enable the prescribed exercise (e.g., cycling in a circular motion profile at a certain range of motion, speed, range of motion, resistance, or some combination thereof) to be performed by using the electromechanical machine 101.

Figure 9:
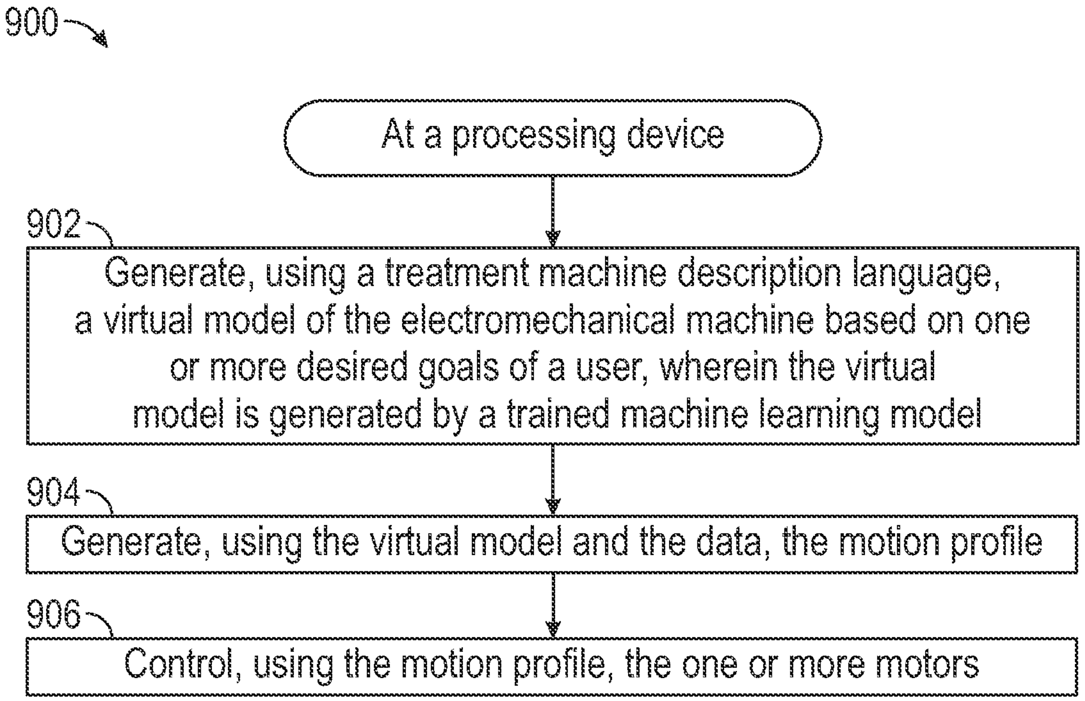
FIG. 9 is a flow diagram generally illustrating a method for generating a virtual model of the electromechanical machine according to the principles of the present disclosure.

FIG. 9 is a flow diagram generally illustrating a method 900 for generating a virtual model of the electromechanical machine according to the principles of the present disclosure. Method 900 includes operations performed by processors of a computing device (e.g., any component of FIG. 3, such as server 30 executing the artificial intelligence engine 11). In some embodiments, one or more operations of the method 900 may be implemented in computer instructions stored on a memory device and executed by a processing device. The method 900 may be performed in the same or a similar manner as described above in regard to method 700. The operations of the method 900 may be performed in some combination with any of the operations of any of the methods described herein.

In some embodiments, one or more machine learning models 13 may be generated and trained by the artificial intelligence engine 11 and/or the training engine 9 to perform one or more of the operations of the method 900. For example, to perform the one or more operations, the processing device may execute the one or more machine learning models 13. In some embodiments, the one or more machine learning models 13 may be iteratively retrained to select different features capable of enabling optimization of output. The features that may be modified may include a number (i.e., quantity) of nodes included in each layer of the machine learning models 13, an objective function executed at each node, a number (i.e., quantity) of layers, various weights associated with outputs of each node, and the like.

At 902, the processing device may generate, based on one or more desired goals of a user and using a treatment machine description language, a virtual model of the electromechanical machine 101. The virtual model may be generated by a trained machine learning model 13. In some embodiments, the treatment machine description language may include a canonical format including tags identifying values of target information, tags implementing an attribute grammar, or some combination thereof. In some embodiments, the target information may pertain to components of an electromechanical machine 101, a layout of the components, parameters of the components, motion profiles of the components, attributes of the components, or some combination thereof. In some embodiments, the treatment machine description language may enable designing and laying out components of a virtual model of the electromechanical machine 101. The machine learning model 13 may be trained with training data including inputs of desired goals associated with the treatment machine description language of electromechanical machines 101 (e.g., components of an electromechanical machine 101, a layout of the components, parameters of the components, motion profiles of the components, attributes of the components, or some combination thereof) and outputs of virtual models of electromechanical machines 101. In some embodiments, to enable achieving the one or more desired goals, the virtual models may include a list of components to use. The list of components may be associated with the electromechanical machine, another electromechanical machine, an accessory, an apparatus, or some combination thereof.

At 906, the processing device may generate, using the virtual model and data comprising a treatment plan including one or more prescribed exercises for a user to perform using the electromechanical machine 101, a motion profile. In some embodiments, the processing device may generate, using the virtual model, a treatment plan to control the electromechanical machine 101.

At 908, the processing device may control, using the motion profile, the one or more motors. The processing device may generate one or more control instructions and transmit them to the one or more motors to cause an operating parameter of the motor to be modified to cause the motion profile of the carriage and/or assembly to be implemented.

Figure 10:
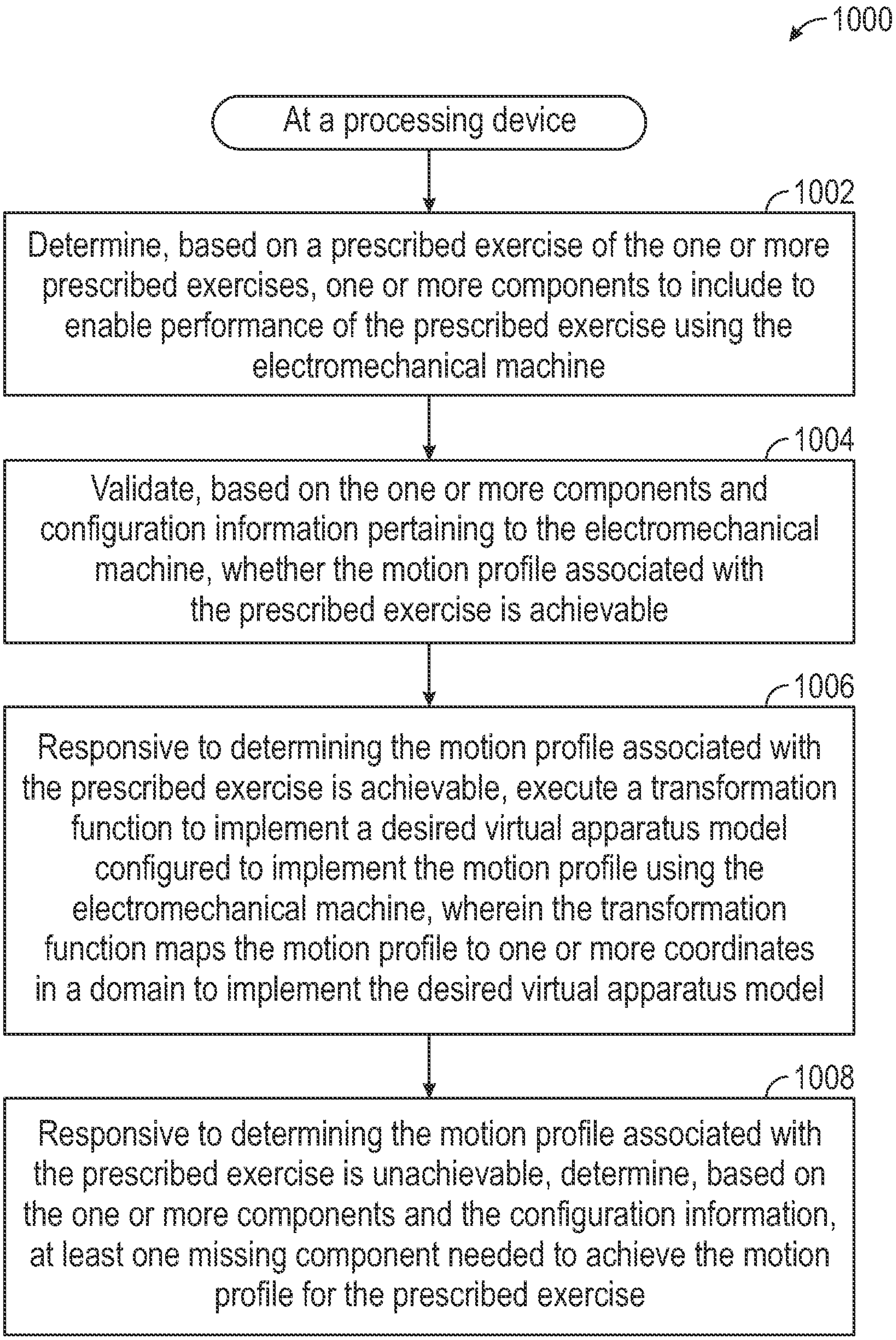
FIG. 10 is a flow diagram generally illustrating a method for using configuration information to determine whether a prescribed exercise can be performed using an electromechanical machine according to the principles of the present disclosure.

FIG. 10 is a flow diagram generally illustrating a method 1000 for using configuration information to determine whether a prescribed exercise can be performed using an electromechanical machine according to the principles of the present disclosure. Method 1000 includes operations performed by processors of a computing device (e.g., any component of FIG. 3, such as server 30 executing the artificial intelligence engine 11). In some embodiments, one or more operations of the method 1000 may be implemented in computer instructions stored on a memory device and executed by a processing device. The method 1000 may be performed in the same or a similar manner as described above in regard to method 700. The operations of the method 1000 may be performed in some combination with any of the operations of any of the methods described herein.

In some embodiments, to perform one or more of the operations of the method 1000, one or more machine learning models 13 may be generated and trained by the artificial intelligence engine 11 and/or the training engine 9. For example, to perform the one or more operations, the processing device may execute the one or more machine learning models 13. In some embodiments, the one or more machine learning models 13 may be iteratively retrained to select different features capable of enabling optimization of output. The features that may be modified may include a number (i.e., quantity) of nodes included in each layer of the machine learning models 13, an objective function executed at each node, a number (i.e., quantity) of layers, various weights associated with outputs of each node, and the like.

At 1002, the processing device may determine, based on a prescribed exercise of the one or more prescribed exercises, one or more components to include to enable performance of the prescribed exercise by using the electromechanical machine 101.

At 1004, the processing device may validate, based on the one or more components and configuration information pertaining to the electromechanical machine 101, whether the motion profile associated with the prescribed exercise is achievable. Achievable as used herein may refer to moving the assembly and/or carriage in a motion profile within a threshold range of accuracy (e.g., 50%-100% traversal of desired locations in a coordinate space mapping the motion profile) and/or within a threshold range of completion (e.g., 50%-100% motions completed). The configuration information may be stored in any suitable file and may include a list of components associated with the electromechanical machine 101. For example, the configuration information may include a parts list. In some embodiments, the configuration information may include information pertaining to one or more exercises enabled using one or more components of the electromechanical machine 101. The configuration information may be stored in a memory device of the electromechanical machine 101, at a server 30, or at any suitable location accessible to the processing device.

At 1006, responsive to determining the motion profile associated with the prescribed exercise is achievable, the processing device may execute a transformation function to implement a desired virtual apparatus model, wherein the desired virtual apparatus model is configured to implement the motion profile by using the electromechanical machine 101. To implement the desired virtual apparatus model, the transformation function may map the motion profile to one or more coordinates in a domain.

At 1008, responsive to determining the motion profile associated with the prescribed exercise is unachievable, the processing device may determine, based on the one or more components and the configuration information, an at least one missing component needed to achieve the motion profile for the prescribed exercise. Unachievable may refer to an inability to move the assembly and/or carriage in a certain motion profile within a threshold range of accuracy (e.g., 50%-100% traversal of desired locations in a coordinate space mapping the motion profile) and/or within a threshold range of completion (e.g., 50%-100% motions completed).

In some embodiments, the processing device may generate and output an electromechanical machine configuration file, wherein the electromechanical machine configuration file includes information pertaining to the at least one missing component. In some embodiments, the configuration file may be presented on a display screen and may provide a selectable option to access a source relating to where to purchase the missing component.

In some embodiments, the processing device may transmit a recommendation to a computing device. The recommendation may be associated with a payment system that enables purchasing the at least one missing component. For example, the payment system may be any suitable digital payment system, such as PayPal®, Venmo®, Zelle®, bitcoin or other cryptocurrency, Monero, MobileCoin, or other coin or stablecoin, Google Pay®, Apple Pay®, any transactional service provided by a financial institution, a financial service, a blockchain, etc.

Figure 11:
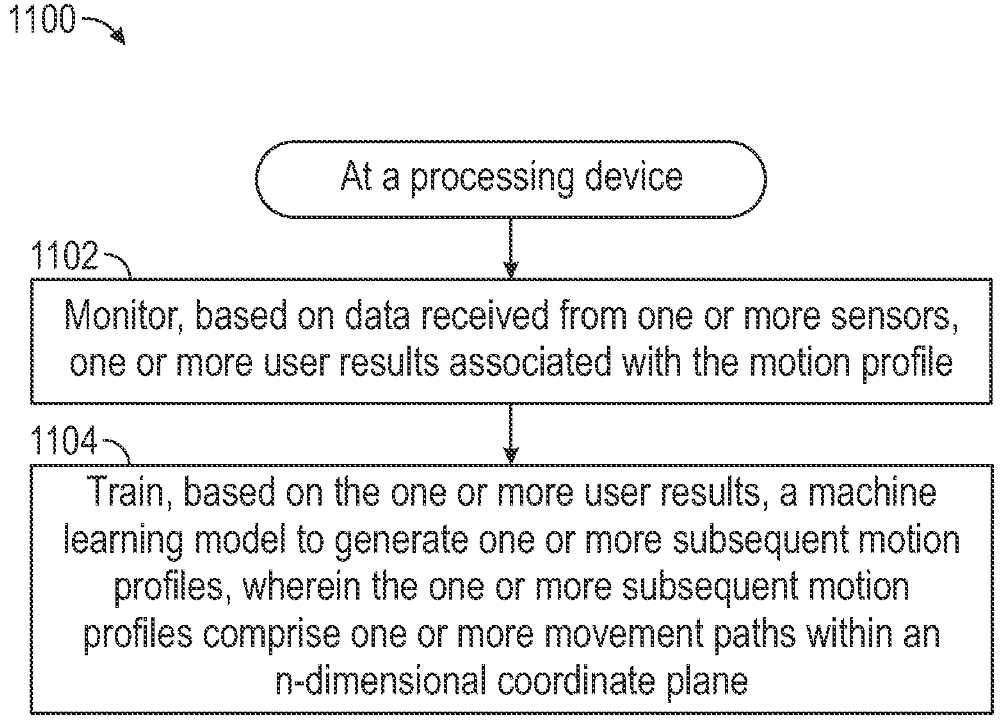
FIG. 11 is a flow diagram generally illustrating a method for using user results to train a machine learning model to generate motion profiles according to the principles of the present disclosure.

FIG. 11 is a flow diagram generally illustrating a method 1100 for using user results to train a machine learning model to generate motion profiles according to the principles of the present disclosure. Method 1100 includes operations performed by processors of a computing device (e.g., any component of FIG. 3, such as server 30 executing the artificial intelligence engine 11). In some embodiments, one or more operations of the method 1100 may be implemented in computer instructions stored on a memory device and executed by a processing device. The method 1100 may be performed in the same or a similar manner as described above in regard to method 700. The operations of the method 1100 may be performed in some combination with any of the operations of any of the methods described herein.

In some embodiments, to perform one or more of the operations of the method 1100, one or more machine learning models 13 may be generated and trained by the artificial intelligence engine 11 and/or the training engine 9. For example, to perform the one or more operations, the processing device may execute the one or more machine learning models 13. In some embodiments, the one or more machine learning models 13 may be iteratively retrained to select different features capable of enabling optimization of output. The features that may be modified may include a number (i.e., quantity) of nodes included in each layer of the machine learning models 13, an objective function executed at each node, a number (i.e., quantity) of layers, various weights associated with outputs of each node, and the like.

At 1102, the processing device may monitor, based on data received from one or more sensors, one or more results associated with the motion profile. The results may pertain to a range of motion achieved by the user when using the motion profile, a speed of pedaling achieved by the user when using the motion profile, an amount of resistance achieved by the user when using the motion profile, etc.

At 1104, to generate one or more subsequent motion profiles, the processing device may train, based on the one or more results, a machine learning model 13. The one or more subsequent motion profiles may include one or more movement paths within an n-dimensional coordinate plane. For example, the results may indicate that a particular motion profile provided excellent results for a particular desired goal and the machine learning model 13 may be trained, when prescribing exercises for that particular desired goal, to more heavily weight a parameter or probability associated with selecting that particular motion profile.

Figure 12:
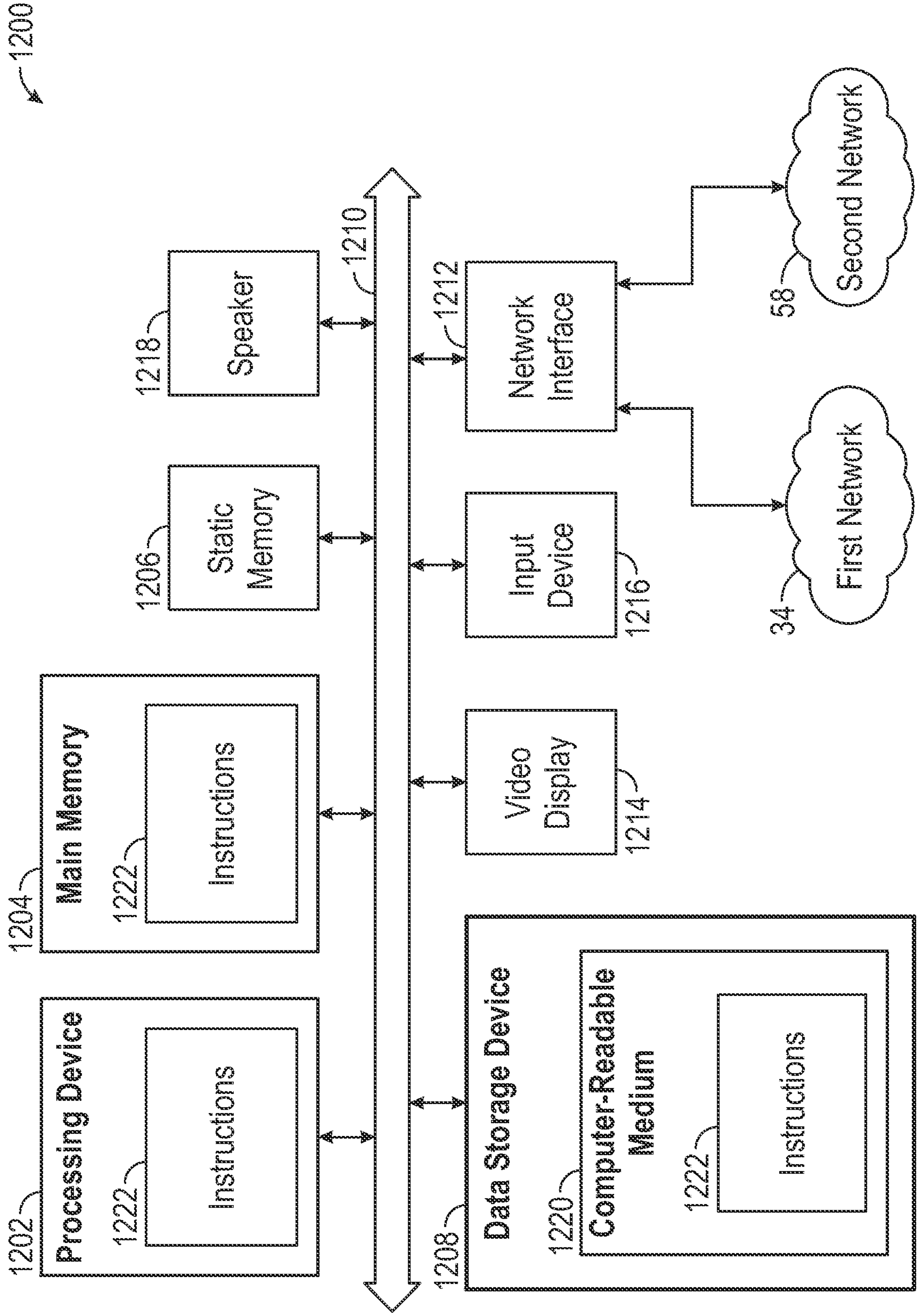
FIG. 12 generally illustrates a computer system according to the principles of the present disclosure.

FIG. 12 shows an example computer system 1200, which can perform any one or more of the methods described herein, in accordance with one or more aspects of the present disclosure. In one example, computer system 1200 may include a computing device and correspond to the assistance interface 94, reporting interface 92, supervisory interface 90, clinician interface 20, server 30 (including the AI engine 11), patient interface 50, ambulatory sensor 82, goniometer 84, electromechanical machine 101, pressure sensor 86, or any suitable component of FIGS. 1-3. The computer system 1200 may be capable of executing instructions implementing the one or more machine learning models 13 of the artificial intelligence engine 11 of FIG. 3. The computer system may be connected (e.g., networked) to other computer systems in a LAN, an intranet, an extranet, or the Internet, including via the cloud or a peer-to-peer network. The computer system may operate in the capacity of a server in a client-server network environment. The computer system may be a personal computer (PC), a tablet computer, a wearable (e.g., wristband), a set-top box (STB), a personal Digital Assistant (PDA), a mobile phone, a camera, a video camera, an Internet of Things (IoT) device, or any device capable of executing a set of instructions (sequential or otherwise) that specify actions to be taken by that device. Further, while only a single computer system is illustrated, the term "computer" shall also be taken to include any collection of computers that individually or jointly execute a set (or multiple sets) of instructions to perform any one or more of the methods discussed herein.

The computer system 1200 includes a processing device 1202, a main memory 1204 (e.g., read-only memory (ROM), flash memory, solid state drives (SSDs), dynamic random access memory (DRAM) such as synchronous DRAM (SDRAM)), a static memory 1206 (e.g., flash memory, solid state drives (SSDs), static random access memory (SRAM)), and a data storage device 1208, which communicate with each other via a bus 1210.

Processing device 1202 represents one or more general-purpose processing devices such as a microprocessor, central processing unit, or the like. More particularly, the processing device 1202 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 1202 may also be one or more special-purpose processing devices such as an application specific integrated circuit (ASIC), a system on a chip, a field programmable gate array (FPGA), a digital signal processor (DSP), network processor, or the like. The processing device 1202 is configured to execute instructions for performing any of the operations and steps discussed herein.

The computer system 1200 may further include a network interface device 1212. The computer system 1200 also may include a video display 1214 (e.g., a liquid crystal display (LCD), a light-emitting diode (LED), an organic light-emitting diode (OLED), a quantum LED, a cathode ray tube (CRT), a shadow mask CRT, an aperture grille CRT, a monochrome CRT), one or more input devices 1216 (e.g., a keyboard and/or a mouse or a gaming-like control), and one or more speakers 1218 (e.g., a speaker). In one illustrative example, the video display 1214 and the input device(s) 1216 may be combined into a single component or device (e.g., an LCD touch screen).

The data storage device 1216 may include a computer-readable medium 1220 on which the instructions 1222 embodying any one or more of the methods, operations, or functions described herein is stored. The instructions 1222 may also reside, completely or at least partially, within the main memory 1204 and/or within the processing device 1202 during execution thereof by the computer system 1200. As such, the main memory 1204 and the processing device 1202 also constitute computer-readable media. The instructions 1222 may further be transmitted or received over a network 34 and/or 58 via the network interface device 1212.

While the computer-readable storage medium 1220 is shown in the illustrative examples to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

Figure 14:
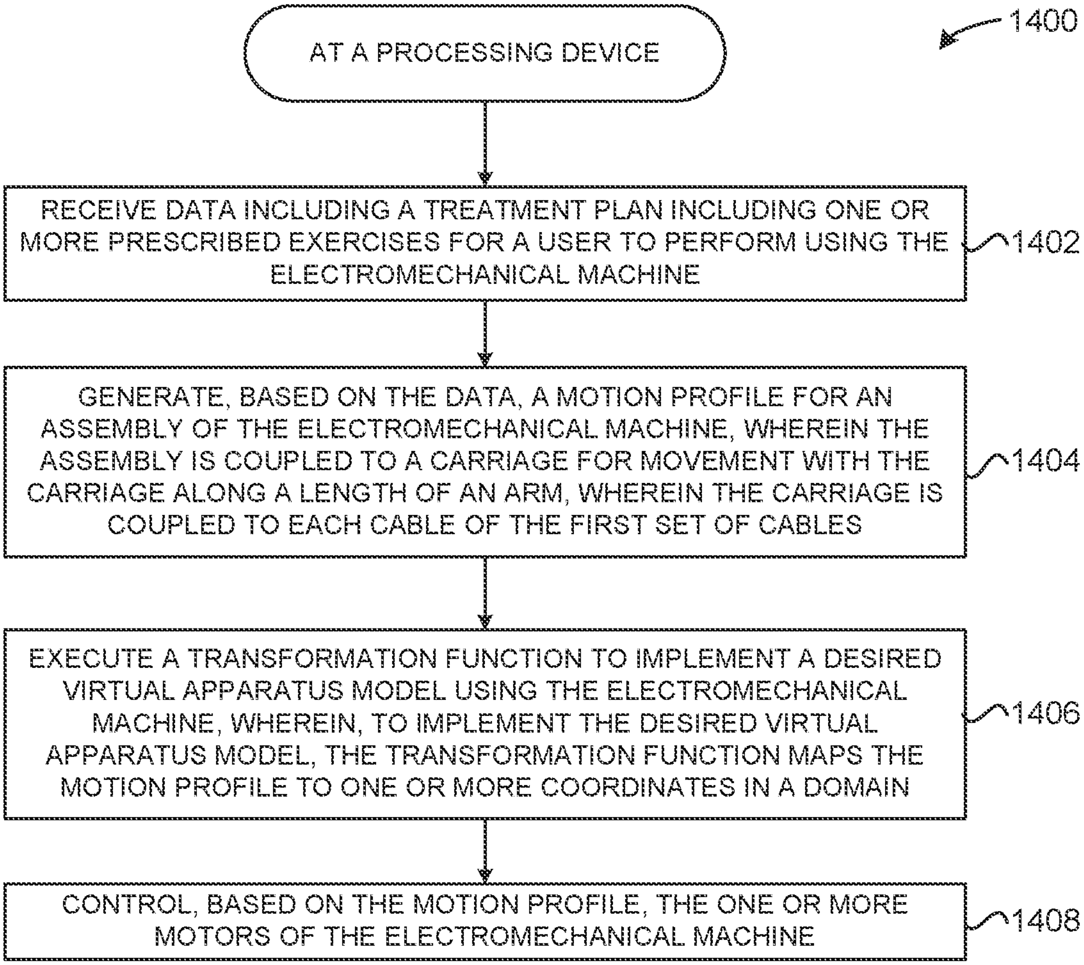
FIG. 14 is a flow diagram generally illustrating a method for using a transformation function to implement a desired virtual apparatus model according to the principles of the present disclosure.

FIG. 14 is a flow diagram generally illustrating a method 1400 for using a transformation function to implement a desired virtual apparatus model according to the principles of the present disclosure. Method 1400 includes operations performed by processors of a computing device (e.g., any component of FIG. 3, such as server 30 executing the artificial intelligence engine 11). In some embodiments, one or more operations of the method 1400 may be implemented in computer instructions stored on a memory device and executed by a processing device. The method 1400 may be performed in the same or a similar manner as described above in regard to method 700. The operations of the method 1400 may be performed in some combination with any of the operations of any of the methods described herein.

In some embodiments, to perform one or more of the operations of the method 1400, one or more machine learning models 13 may be generated and trained by the artificial intelligence engine 11 and/or the training engine 9. For example, to perform the one or more operations, the processing device may execute the one or more machine learning models 13. In some embodiments, the one or more machine learning models 13 may be iteratively retrained to select different features capable of enabling optimization of output. The features that may be modified may include a number (i.e., quantity) of nodes included in each layer of the machine learning models 13, an objective function executed at each node, a number (i.e., quantity) of layers, various weights associated with outputs of each node, and the like. An objective function may refer to a function that maximizes or minimizes a value. An objection function may be a function represented as linear equation (e.g., Z=zx+by) and is used to represent optimization problems in linear programming. For example, an objective function may attempt to maximize a range of motion provided by a motion profile based on a set of constraints and a relationship between one or more variables.

The method 1400 may be implemented in instructions and executed by a processing device communicatively coupled to one or more motors of an electromechanical machine 2101. The one or more motors may be mounted to a body and spaced apart from each other. The electromechanical machine 2101 may include a first set of cables, each coupled to a respective one of the motors.

At 1402, the processing device may receive data, and the data may include a treatment plan. The treatment plan may include one or more prescribed exercises for a user to perform using the electromechanical machine. In some embodiments, the processing device may be disposed in a computing device separate from the electromechanical machine 2101; in some other embodiments, the processing device may be disposed in the electromechanical machine 2101.

In some embodiments, a headset may be configured to present, based on a prescribed exercise of the one or more prescribed exercises, a virtual reality element that modifies an appearance in the headset of the electromechanical machine 2101. For example, the virtual reality element may cause the electromechanical machine to represent a treadmill, a stationary bicycle, a stair-stepper machine, or the like. In some embodiments, a display may be configured to present, based on a prescribed exercise of the one or more prescribed exercises, an augmented reality element that modifies on the display an appearance of the electromechanical machine 2101. The augmented reality element may represent, for a stair-stepper exercise, a virtual stair; for a walking exercise, a virtual walking belt; for a pedaling exercise, a virtual pedal; and for other exercises, a corresponding virtual element associated with the electromechanical machine 2021.

At 1404, the processing device may generate, based on the data, a motion profile for an assembly of the electromechanical machine 2101. The assembly may be coupled to a carriage to enable movement along a length of an arm. In some embodiments, the assembly may include a handlebar assembly, a row assembly, a pedal assembly, a climbable assembly, a step assembly, a paddle assembly, a brace assembly, a lift assembly, a push assembly, a balance assembly, or some combination thereof. The assembly may include a pedal assembly and the pedal assembly is rotatably coupled to the carriage. The carriage may be coupled to each cable of the first set of cables. In some embodiments, the processing device may execute an artificial intelligence engine 11 to generate one or more machine learning models 13 trained to generate the motion profile for the assembly. In some embodiments, the motion profile may include a line or a geometrical shape.

At 1406, the processing device may, using the electromechanical machine 2101, execute a transformation function to implement a desired virtual apparatus model. To implement the desired virtual apparatus model, the transformation function may map the motion profile to one or more coordinates in an n-dimensional domain. The desired virtual apparatus model may include virtual components for each component (e.g., such as the assembly, the motors, the pedals, the cables, the carriages, and the like) that is used during the prescribed exercise. The desired virtual apparatus model may be used to simulate the motion profile on a display of a computing device. The desired virtual apparatus model may be an n-dimensional object that can be graphically presented and may be animated to illustrate the motion profile associated with the prescribed exercise. The desired virtual apparatus model may include a mathematical coordinate-based representation of an object (e.g., electromechanical machine) in n-dimensions (e.g., 3) based on manipulating edges, vertices, and/or polygons in a simulated n-dimensional space. A mathematical mesh of polygons may be used to define reference points in X, Y, and Z axes in order to enable the definition of shapes with height, width, and depth. The elements of the desired virtual apparatus model may be mapped to the actual components of the electromechanical machine 2101. For example, a virtual motor may be mapped to and control an actual motor of the electromechanical machine (e.g., changing revolutions per minute of the virtual motor causes the actual motor to change its revolutions per minute).

At 1408, the processing device may control, using the desired virtual apparatus model, the one or more motors of the electromechanical machine 2101. In some embodiments, the processing device may control the one or more motors to operate in a set of modes including an active mode, an active-assist mode, an assisted mode, a passive mode, or some combination thereof. In some embodiments, using the electromechanical machine 2102 by controlling the one or more motors based on the motion profile, the set of modes, or some combination thereof, the processing device may enable performing at least one of the one or more prescribed exercises.

In some embodiments, the processing device may use a machine learning model trained to control one or more spools of the first set of cables, one or more speeds of the one or more motors, one or more resistances provided by the one or more motors, one or more ranges of motion of the carriage and assembly, or some combination thereof. For example, the machine learning models may be trained with training data that includes labeled inputs mapped to labeled outputs. The labeled inputs may include information pertaining to exercises of a treatment plan and the labeled outputs may include operating parameters for one or more components of the electromechanical machine 2101. The operating parameters may enable the electromechanical machine 2101 to perform the exercises. In some embodiments, the machine learning models may output one or more probabilities, wherein each of the probabilities is associated with at least one of the operating parameters. The determination of the operating parameters to have a certain probability may cause a determined operating parameter to be selected to control the electromechanical machine 2101.

Figure 15:
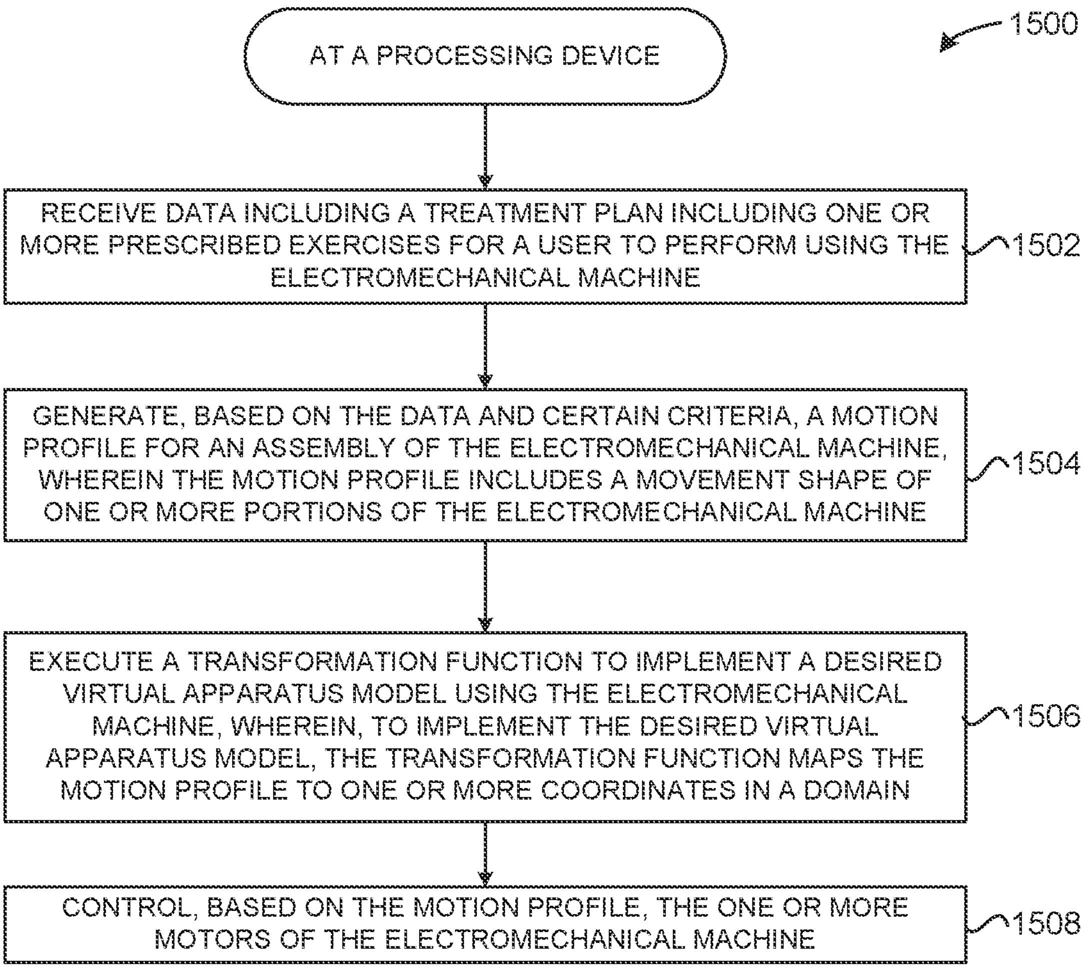
FIG. 15 is a flow diagram generally illustrating a method to transform the movement shape of one or more portions of a machine based on certain criteria according to the principles of the present disclosure.

FIG. 15 is a flow diagram generally illustrating a method 1500 to transform the movement shape of one or more portions of a machine, wherein the transformation is based on certain criteria according to the principles of the present disclosure. Method 1500 includes operations performed by processors of a computing device (e.g., any component of FIG. 3, such as server 30 executing the artificial intelligence engine 11). In some embodiments, one or more operations of the method 1500 may be implemented in computer instructions stored on a memory device and executed by a processing device. The method 1500 may be performed in the same or a similar manner as described above in regard to method 700. The operations of the method 1500 may be performed in some combination with any of the operations of any of the methods described herein.

In some embodiments, to perform one or more of the operations of the method 1500, one or more machine learning models 13 may be generated and trained by the artificial intelligence engine 11 and/or the training engine 9. For example, to perform the one or more operations, the processing device may execute the one or more machine learning models 13. In some embodiments, the one or more machine learning models 13 may be iteratively retrained to select different features capable of enabling optimization of output. The features that may be modified may include a number (i.e., quantity) of nodes included in each layer of the machine learning models 13, an objective function executed at each node, a number (i.e., quantity) of layers, various weights associated with outputs of each node, and the like.

The method 1500 may be implemented in instructions and executed by a processing device communicatively coupled to one or more motors of an electromechanical machine 2101. The one or more motors may be mounted to a body and spaced apart from each other. The electromechanical machine 21201 may include a first set of cables, each coupled to a respective one of the motors.

At 1502, the processing device may receive data including a treatment plan. The treatment plan may include one or more prescribed exercises for a user to perform using the electromechanical machine 2101. The one or more prescribed exercises may specify a duration to exercise, a type (e.g., walking, cycling, climbing, rowing, etc.) of exercise, an amount of weight to use during the exercise, an amount of resistance to provide during the exercise, etc.

At 1504, the processing device may generate, based on the data and certain criteria, a motion profile for an assembly of the electromechanical machine 2101. The motion profile may include a movement shape of one or more portions of the electromechanical machine 2101. In some embodiments, the movement shape may include a line and/or a geometrical shape. In some embodiments, the certain criteria may include one or more muscle groups, one or more user attributes comprising height, weight, demographic characteristics, psychographic characteristics, race, gender, medical history, comorbidities, prescription medications, non-prescription medications or nutritional supplements, familial medical history, and performed medical procedures on the user, one or more desired results, or some combination thereof.

For example, if the criteria indicate the user is over 6 feet tall and the data indicate the type of exercise is a cycling exercise, then the motion profile may include a larger circular movement than if the user were 5 feet tall. In other words, the criteria may cause the motion profile to be adjusted accordingly in order to accommodate and/or enable the user to perform a prescribed exercise that is defined in the data.

In some embodiments, the assembly may be coupled to a carriage to enable movement along a length of an arm. The carriage may be coupled to each cable of the first set of cables.

At 1506, the processing device may execute a transformation function to implement, using the electromechanical machine 2101, a desired virtual apparatus model. To implement the desired virtual apparatus model, the transformation function may map the motion profile to one or more coordinates in an n-dimensional domain. For example, a movement path defined by the motion profile may be mapped to a 3-dimensional coordinate space. The coordinate space may accurately represent an area in which the components of the electromechanical machine 2101 move during operation.

At 1508, the processing device may control, using the desired virtual apparatus model, the one or more motors of the electromechanical machine 2101. In some embodiments, the processing device may control the one or more motors to operate in a plurality of modes including an active mode, an active-assist mode, an assisted mode, a passive mode, or some combination thereof. To control the motor, the processing device may transmit one or more control instructions including metadata related to one or more operating parameters (e.g., speed, revolutions per minute, torque, acceleration, etc.). The one or more control instructions may be transmitted to the motor, and a processing device associated with the motor may receive and execute the one or more control instructions based on the one or more operating parameters.

In some embodiments, by using the electromechanical machine 2101 in order to control the one or more motors based on the motion profile, the plurality of modes, or some combination thereof, the processing device may enable performing at least one of the one or more prescribed exercises. For example, one of the prescribed exercises may include cycling at different resistance levels, and the modes may be used to provide the resistance levels while the user performs the exercise. In some embodiments, the motion profile may specify a circular movement path of the components of the electromechanical machine 2101.

In some embodiments, a headset may present, based on a prescribed exercise of the one or more prescribed exercises, a virtual reality element that modifies an appearance in the headset of the electromechanical machine 2101. In some embodiments, a display may present, based on a prescribed exercise of the one or more prescribed exercises, an augmented reality element that modifies on the display an appearance of the electromechanical machine 2101.

Figure 16:
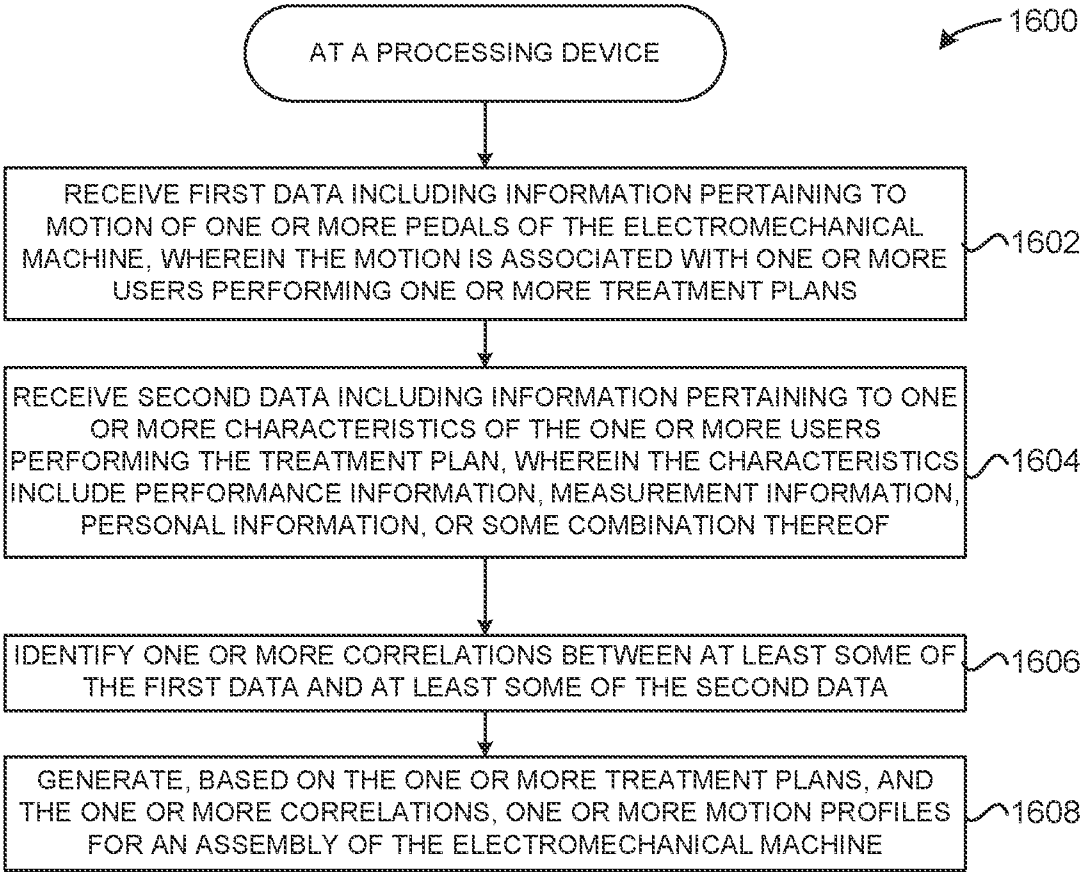
FIG. 16 is a flow diagram generally illustrating a method to determine pedal motion profiles based on identified correlations between pedal motion and user impact according to the principles of the present disclosure.

FIG. 16 is a flow diagram generally illustrating a method 1600 to determine, based on identified correlations between pedal motion and user impact, pedal motion profiles according to the principles of the present disclosure. Method 1600 may include operations performed by processors of a computing device (e.g., any component of FIG. 3, such as server 30 executing the artificial intelligence engine 11). In some embodiments, one or more operations of the method 1600 may be implemented in computer instructions stored on a memory device and executed by a processing device. The method 1600 may be performed in the same or a similar manner as described above in regard to method 700. The operations of the method 1600 may be performed in some combination with any of the operations of any of the methods described herein.

In some embodiments, to perform one or more of the operations of the method 1600, one or more machine learning models 13 may be generated and trained by the artificial intelligence engine 11 and/or the training engine 9. For example, to perform the one or more operations, the processing device may execute the one or more machine learning models 13. In some embodiments, the one or more machine learning models 13 may be iteratively retrained to select different features capable of enabling optimization of output. The features that may be modified may include a number (i.e., quantity) of nodes included in each layer of the machine learning models 13, an objective function executed at each node, a number (i.e., quantity) of layers, various weights associated with outputs of each node, and the like.

The method 1600 may be implemented in instructions and executed by a processing device communicatively coupled to one or more motors of an electromechanical machine 2101. The one or more motors may be mounted to a body and spaced apart from each other. The electromechanical machine 2101 may include a first set of cables, each coupled to a respective one of the motors.

At 1602, the processing device may receive first data including information pertaining to motion of one or more pedals of one or more electromechanical machines. The motion may be associated with one or more users performing one or more treatment plans. In some embodiments, the first data may include one or more motion profiles associated with one or more exercises performed by one or more users. The processing device may receive the first data from the one or more electromechanical machines, one or more server computing devices, one or more user computing devices, or some combination thereof.

At 1604, the processing device may receive second data including information pertaining to one or more characteristics of the one or more users performing the treatment plan. The processing device may receive the second data from one or more sensors, one or more computing devices, or the like. The characteristics may include performance information, measurement information, personal information, or some combination thereof. The personal information may include, e.g., demographic, psychographic or other information, such as an age, a weight, a gender, a height, a body mass index, a medical condition, a familial medication history, an injury, a medical procedure, a medication prescribed, or some combination thereof. The performance information may include, e.g., an elapsed time of using a treatment apparatus, an amount of force exerted on a portion of the treatment apparatus, a range of motion achieved on the treatment apparatus, a speed or velocity measurement of a moving portion of the treatment apparatus, a pressure exerted by the user on a portion of the exercise apparatus, an acceleration measurement of a moving portion of the exercise apparatus, a jerk of a portion of the exercise apparatus, a torque level induced by the user on a portion of the exercise apparatus, an indication of a plurality of pain levels experienced by the user when using the treatment apparatus, a duration of use of the treatment apparatus, or some combination thereof. The measurement information may include, e.g., a vital sign, a respiration rate, a heartrate, a temperature, a blood pressure, a glucose level, arterial blood gas and/or oxygenation levels or percentages, or other biomarker, or some combination thereof.

At 1606, the processing device may identify one or more correlations between at least some of the first data and at least some of the second data. In some embodiments, the one or more correlations may pertain to one or more results achieved with respect to a threshold achievement level measured in relation to the one or more characteristics. The threshold achievement level may include a certain value, number, range, percentage, qualifier, etc. In some embodiments, the threshold achievement level may be based on a completion percentage, a recovery percentage, a value, a target reached, or some combination thereof. The results may indicate that, after knee surgery, the user rehabilitated their range of motion by over 75 percent, which would be, e.g., higher than the threshold achievement level. A motion profile used by the user to perform the prescribed exercise may be used to enable other similar users (e.g., in terms of personal information) to achieve the same or a similar result. Since a user may achieve more than one result after performing an exercise, there may be various cohorts of motion profiles assigned to more than one result.

A processing device may be programmed to select a motion profile for a user based on its being assigned to the greatest number of positive results relative to the other motion profiles. In some embodiments, the processing device may select a motion profile for a user if the motion profile provides the most optimal result (e.g., fastest recovery time, highest amount of recovery, etc.) in one cohort relative to the other motion profiles assigned to that cohort.

At 1608, the processing device may generate, based on the one or more treatment plans and the one or more correlations, one or more motion profiles for an assembly of the electromechanical machine 2101. In some embodiments, the processing device may receive a prescribed treatment plan for a user. The prescribed treatment plan may be received from a computing device associated with a healthcare professional and/or provider or from any suitable source. The processing device may select, based on the prescribed treatment plan, a motion profile from the one or more motion profiles to be performed by the user. The motion profile may be configured to provide a desired result, targeted result, targeted output, desired outcome, specified outcome, or the like.

For each of the one or more motion profiles, the processing device may execute a transformation function to implement, using the electromechanical machine 2101, a desired virtual apparatus model. To implement the desired virtual apparatus model, the transformation function may map the motion profile to one or more coordinates in an n-dimensional domain.

In some embodiments, the processing device may control, using the desired virtual apparatus model, the one or more motors of the electromechanical machine 2101. In some embodiments, the processing device may control the one or more motors to operate in a set of modes including an active mode, an active-assist mode, an assisted mode, a passive mode, or some combination thereof. In some embodiments, the processing device may use a machine learning model trained to control one or more spools of the first set of cables, one or more speeds of the one or more motors, one or more resistances provided by the one or more motors, one or more ranges of motion of the carriage and assembly, or some combination thereof.

Figure 17:
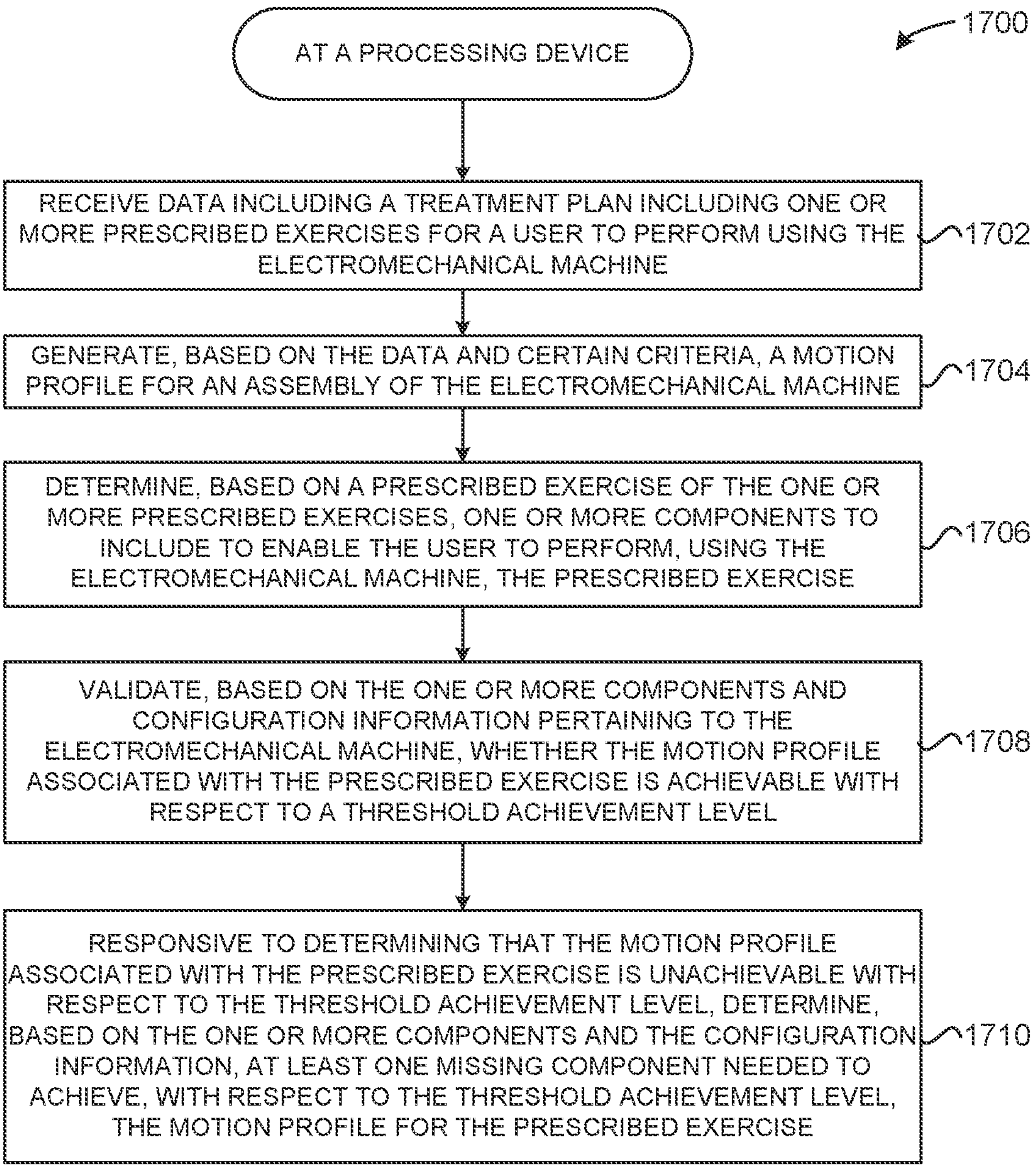
FIG. 17 is a flow diagram generally illustrating a method for automatic prompting payment system to purchase components for mapped exercises according to the principles of the present disclosure.

FIG. 17 is a flow diagram generally illustrating a method 1700 for an automatic prompting payment system to purchase components for mapped exercises according to the principles of the present disclosure. Method 1700 includes operations performed by processors of a computing device (e.g., any component of FIG. 3, such as server 30 executing the artificial intelligence engine 11). In some embodiments, one or more operations of the method 1700 may be implemented in computer instructions stored on a memory device and executed by a processing device. The method 1700 may be performed in the same or in a similar manner as described above in regard to method 700. The operations of the method 1700 may be performed in some combination with any of the operations of any of the methods described herein.

In some embodiments, to perform one or more of the operations of the method 1700, one or more machine learning models 13 may be generated and trained by the artificial intelligence engine 11 and/or the training engine 9. For example, to perform the one or more operations, the processing device may execute the one or more machine learning models 13. In some embodiments, the one or more machine learning models 13 may be iteratively retrained to select different features capable of enabling optimization of output. The features that may be modified may include a number (i.e., quantity) of nodes included in each layer of the machine learning models 13, an objective function executed at each node, a number (i.e., quantity) of layers, various weights associated with outputs of each node, and the like.

The method 1700 may be implemented in instructions and executed by a processing device communicatively coupled to one or more motors of an electromechanical machine 2101. The one or more motors may be mounted to a body and spaced apart from each other. The electromechanical machine 2101 may include a first set of cables, each coupled to a respective one of the motors.

At 1702, the processing device may receive data including a treatment plan. The treatment plan may include one or more prescribed exercises for a user to perform using the electromechanical machine 2101.

At 1704, the processing device may generate, based on the data, a motion profile for an assembly of the electromechanical machine 2101. The assembly may be coupled to a carriage to enable movement along a length of an arm, wherein the carriage is coupled to each cable of the first set of cables.

At 1706, the processing device may determine, based on a prescribed exercise of the one or more prescribed exercises, one or more components to include to enable the user to perform, using the electromechanical machine 2101, the prescribed exercise. For example, the one or more components may refer to one or more pedals, motors, assemblies, carriages, cables, or the like. If the prescribed exercise is a cycling exercise, then the one or more components may include at least one or more pedals to enable the user to perform the cycling exercise using the electromechanical machine 2101. The one or more components may be determined by referencing a data source storing the components involved in each exercise.

At 1708, the processing device may validate, based on the one or more components and configuration information pertaining to the electromechanical machine, whether the motion profile associated with the prescribed exercise is achievable with respect to a threshold achievement level (e.g., a certain value, number, range, percentage, qualifier, etc.). The configuration information pertaining to the electromechanical machine 2101 may specify which components are included in the electromechanical machine 2101 (e.g., 2 pedals, 2 motors, 4 cables, 2 assemblies, etc.). The configuration information may be stored in a database local to the electromechanical machine 2101, in a server computing device, in a user computing device (e.g., smartphone), or the like. The processing device may determine that the electromechanical machine is missing a certain component that may prevent the motion profile from being achieved with respect to the threshold achievement level. For example, if the threshold achievement level is providing a motion profile enabling a range of motion of 75 degrees, and the electromechanical machine's configuration information and/or components indicate that only a motion profile providing a 50 degree range of motion is possible, then the electromechanical machine would be incapable of enabling the desired motion profile.

At 1710, responsive to determining that the motion profile associated with the prescribed exercise is unachievable with respect to the threshold achievement level, the processing device may determine, based on the one or more components and the configuration information, an at least one missing component needed to achieve, with respect to the threshold achievement level, the motion profile for the prescribed exercise. For example, the processing device may determine that the at least one missing component includes an elevation block to provide an inclination, wherein the elevation block is inserted under a front portion of the electromechanical machine. Such an inclination may cause the motion profile to enable the prescribed exercise to be performed with respect to the threshold achievement level.

In some embodiments, the processing device may generate and output an electromechanical machine configuration file, wherein the electromechanical machine configuration file may include information pertaining to the at least one missing component (e.g., a make, a model, a brand, size, shape, etc.). The processing device may transmit a recommendation to a computing device, wherein the recommendation is associated with a payment system that enables purchasing the at least one missing component. The computing device may be associated with the user and may be a smartphone or any other suitable electronic device. The recommendation may be delivered as a message via a push notification, a text message, an email, or any suitable electronic communication channel. The user may select a link and/or open the message to be presented with the missing component in a payment system, such as Amazon®. The user may purchase, using a digital wallet or any suitable form of payment (e.g., credit card), the missing component from the payment system. After the missing component has been purchased, the missing component may be shipped to and received by the user. The user may install the missing component on the electromechanical machine 2101 to enable achieving the motion profile associated with the prescribed exercise. The process for determining whether the motion profile is achievable may be repeated until the processing device determines that the threshold achievement level has been exceeded or satisfied or until the processing device determines that the threshold achievement level cannot be reached or satisfied in general or with respect to a time limitation.

In some embodiments, responsive to determining the motion profile associated with the prescribed exercise is achievable with respect to the threshold achievement level, the processing device may execute a transformation function to implement a desired virtual apparatus model configured to implement, by using the electromechanical machine 2101, the motion profile. To implement the desired virtual apparatus model, the transformation function may map the motion profile to one or more coordinates in an n-dimensional domain. The processing device is further configured to control, using the desired virtual apparatus model, the one or more motors of the electromechanical machine 2101.

In some embodiments, the processing device is further configured to control the one or more motors to operate in a set of modes, including an active mode, an active-assist mode, an assisted mode, a passive mode, or some combination thereof.

Figure 18:
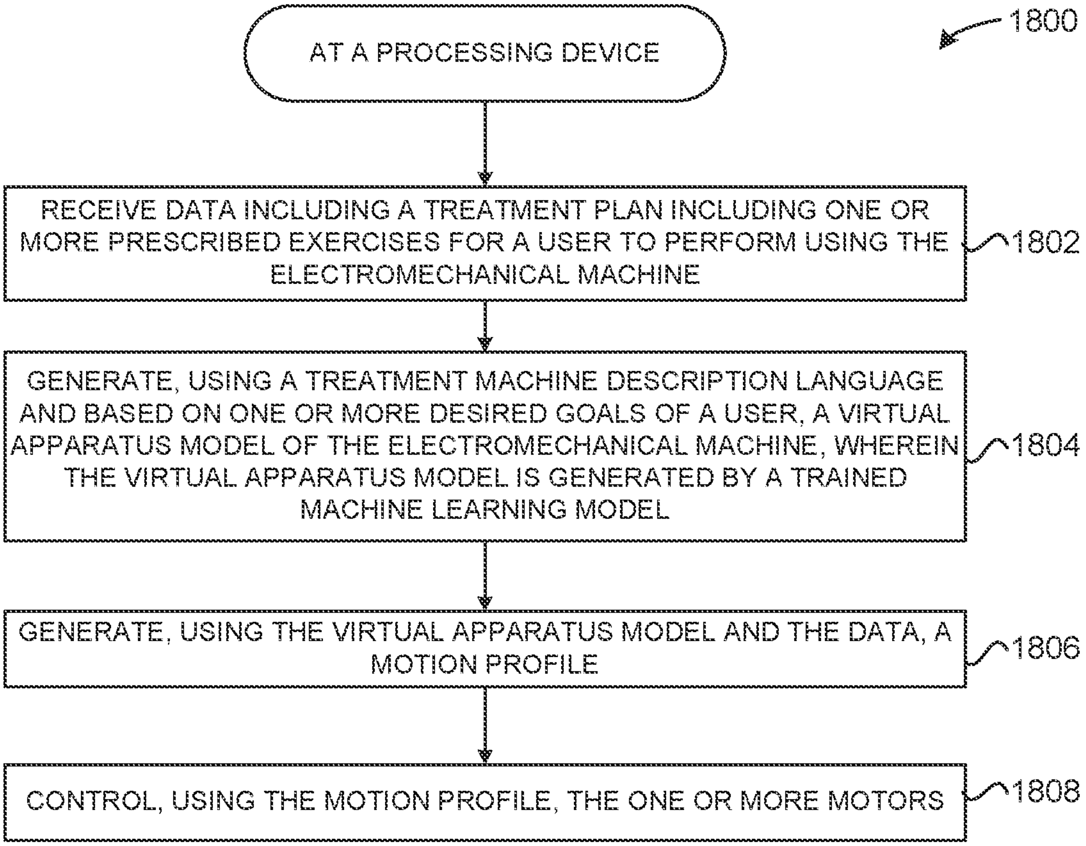
FIG. 18 is a flow diagram generally illustrating a method for implementing a treatment machine description language according to the principles of the present disclosure.

FIG. 18 is a flow diagram generally illustrating a method 1800 for implementing a treatment machine description language according to the principles of the present disclosure. Method 1800 includes operations performed by processors of a computing device (e.g., any component of FIG. 3, such as server 30 executing the artificial intelligence engine 11). In some embodiments, one or more operations of the method 1800 may be implemented in computer instructions stored on a memory device and executed by a processing device. The method 1800 may be performed in the same or a similar manner as described above in regard to method 700. The operations of the method 1800 may be performed in some combination with any of the operations of any of the methods described herein.

In some embodiments, to perform one or more of the operations of the method 1800, one or more machine learning models 13 may be generated and trained by the artificial intelligence engine 11 and/or the training engine 9. For example, to perform the one or more operations, the processing device may execute the one or more machine learning models 13. In some embodiments, the one or more machine learning models 13 may be iteratively retrained to select different features capable of enabling optimization of output. The features that may be modified may include a number (i.e., quantity) of nodes included in each layer of the machine learning models 13, an objective function executed at each node, a number (i.e., quantity) of layers, various weights associated with outputs of each node, and the like.

The method 1800 may be implemented in instructions and executed by a processing device communicatively coupled to one or more motors of an electromechanical machine 2101. The one or more motors may be mounted to a body and spaced apart from each other. The electromechanical machine 2101 may include a first set of cables, each coupled to a respective one of the motors.

At 1802, the processing device may receive data comprising a treatment plan including one or more prescribed exercises for a user to perform using the electromechanical machine.

At 1804, the processing device may generate, using a treatment machine description language and based on one or more desired goals of a user, a virtual apparatus model of the electromechanical machine. The virtual apparatus model may be generated by a trained machine learning model. The treatment machine description language may comprise a canonical format including tags identifying values of at least some target information, tags implementing an attribute grammar, tags used for lexical comparisons or equivalence scores, or some combination thereof. The target information may describe components of electromechanical machines, exercises in which those components are used, descriptions of the components, results obtained by using the components, etc. The target information may be organized in parent-child relationships based on the structure, organization, and/or relationships of the information. For example, the keyword "Results" may be identified and determined to be a parent level tag due to its encompassing children target information, such as trials, subjects, treatment plans, treatment apparatuses, components, subject characteristics, and conclusions. As such, a parent-level tag for "<results>" may include child-level tags for "<trials>", "<subjects>", "<treatment plans>", "<treatment apparatuses>", "<components>", "<subject characteristics>", and "<conclusions>". Each tag may have a corresponding ending tag (e.g., "<results> . . . </results>").

In some embodiments, the virtual apparatus model may include a list of components to use to enable achieving the one or more desired goals. The achieving is measured with respect to a threshold achievement level. In some embodiments, the list of components may be associated with the electromechanical machine 2101, another electromechanical machine, an accessory, an apparatus, or some combination thereof.

A machine learning model 13 may be trained to generate, using the treatment machine description language and desired goals of a user, the virtual apparatus model. The machine learning model 13 may be trained using a training data set including input data and output data. The input data may be labeled as being associated with output data comprising virtual models of desired electromechanical machines and motion profiles, wherein such virtual models are configured to enable achieving the desired goals. In some embodiments, the virtual models (e.g., desired virtual apparatus model) may include a list of components needed to perform certain prescribed exercises to achieve the desired goals. In some embodiments, the electromechanical machine 2101 prescribed or associated with the user may lack one or more of the components in the list of components. In any such instance, a recommendation may be generated and output to a computing device, and the recommendation may include information associated with purchasing or obtaining the missing component such that the user can use the electromechanical machine to perform the prescribed exercise.

Information pertaining to new electromechanical machines may be received by the processing device. The one or more machine learning models may be trained to translate the information from a first data format to the treatment machine description language having a canonical (e.g., tag-value pair and/or attribute grammar) format. The training may be performed by identifying the keywords of the target information, identifying values for the keywords, and generating the canonical value, wherein the canonical value includes tags for the target information and the values for the target information.

At 1806, the processing device may generate, using the virtual apparatus model and the data, a motion profile. Further, the processing device may generate, using the artificial intelligence engine 11, a machine learning model 13 trained to generate the motion profile for the assembly. The machine learning model 13 may be trained using training data that includes inputs labeled as a prescribed exercise and/or the virtual apparatus model and outputs labeled as a probable motion profile, where the motion profile enables the user to use the virtual apparatus model to achieve the prescribed exercise relative to the threshold achievable threshold.

At 1808, the processing device may control, using the motion profile, the one or more motors. In some embodiments, the processing device may, by transmitting a control instruction or control signal including one or more operating parameters to the one or more motors, control the one or more motors. The one or more motors may modify the operating parameters accordingly to provide a desired operating state to enable the motion profile to be achieved for the prescribed exercise.

In some embodiments, a headset may be configured to present, based on a prescribed exercise of the one or more prescribed exercises, a virtual reality element that modifies in the headset an appearance of the electromechanical machine 2101. In some embodiments, a display may be configured to present, based on a prescribed exercise of the one or more prescribed exercises, an augmented reality element that modifies on the display an appearance of the electromechanical machine 2101.

The terminology used herein is for the purpose of describing particular example embodiments only and is not intended to be limiting. As used herein, the singular forms “a,” “an,” and “the” may be intended to include the plural forms as well, unless the context clearly indicates otherwise. The terms “comprises,” “comprising,” “including,” and “having,” are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being “on,” “engaged to,” “connected to,” or “coupled to” another element or layer, it may be directly on, engaged, connected or coupled to the other element or layer, or intervening elements or layers may be present. In contrast, when an element is referred to as being “directly on,” “directly engaged to,” “directly connected to,” or “directly coupled to” another element or layer, there may be no intervening elements or layers present. Other words used to describe the relationship between elements should be interpreted in a like fashion (e.g., “between” versus “directly between,” “adjacent” versus “directly adjacent,” etc.). As used herein, the term “and/or” includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as “first,” “second,” and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as “inner,” “outer,” “beneath,” “below,” “lower,” “above,” “upper,” “top”, “bottom,” and the like, may be used herein for ease of description to describe one element’s or feature’s relationship to another element(s) or feature(s) as illustrated in the figures. Spatially relative terms may be intended to encompass different orientations of the device in use or operation in addition to the orientation depicted in the figures. For example, if the device in the figures is turned over, elements described as “below” or “beneath” other elements or features would then be oriented “above” the other elements or features. Thus, the example term “below” can encompass both an orientation of above and below. The device may be otherwise oriented (rotated degrees or at other orientations) and the spatially relative descriptions used herein interpreted accordingly.

This written description uses examples to disclose the embodiments, including the best mode, and also to enable those of ordinary skill in the art to make and use the invention. The patentable scope is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

It can be advantageous to set forth definitions of certain words and phrases used throughout this patent document. The term "communicate," as well as derivatives thereof, encompasses both direct and indirect communication. The terms "include" and "comprise," as well as derivatives thereof, mean inclusion without limitation. The term "or" is inclusive, meaning and/or. The phrase "associated with," as well as derivatives thereof, can mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items can be used, and only one item in the list can be needed. For example, "at least one of: A, B, and C" includes any of the following combinations: A, B, C, A and B, A and C, B and C, and A and B and C.

Also, the use of "a" or "an" is employed to describe elements and components described herein. This is done merely for convenience and to give a general sense of the scope of the invention. This description should be read to include one or at least one and the singular also includes the plural unless it states otherwise.

The description in the present application should not be read as implying that any particular element, step, or function is an essential or critical element that must be included in the claim scope. The scope of patented subject matter is defined only by the allowed claims. Moreover, none of the claims invokes 35 U.S.C. § 112(f) with respect to any of the appended claims or claim elements unless the exact words "means for" or "step for" are explicitly used in the particular claim, followed by a participial phrase identifying a function.

Benefits, other advantages, and solutions to problems have been described above with regard to specific embodiments. However, the benefits, advantages, solutions to problems, and any feature(s) that can cause any benefit, advantage, or solution to occur or become more pronounced are not to be construed as a critical, a required, a sacrosanct or an essential feature of any or all the claims.

After reading the specification, skilled artisans will appreciate that certain features which are, for clarity, described herein in the context of separate embodiments, can also be provided in combination in a single embodiment. Conversely, various features that are, for brevity, described in the context of a single embodiment, can also be provided separately or in any subcombination. Further, references to values stated in ranges include each and every value within that range.

Still other embodiments can include one or more of the following items. Consistent with the above disclosure, the examples of embodiments enumerated in the following clauses are specifically contemplated and are intended as a non-limiting set of examples.

Clause 1. A machine, comprising:
- a body;
- an arm having a proximal end and a distal end, the proximal end is pivotally mounted to the body, and the distal end is free to move relative to the body;
- a carriage slidably mounted to the arm for movement along a length of the arm;
- a pedal assembly rotatably coupled to the carriage for movement with the carriage along the length of the arm, wherein the pedal assembly is configured to support a foot of a user of the machine.
- motors mounted to the body and spaced apart from each other and spaced apart from the distal end of the arm;
- cables coupled to respective ones of the motors and to the carriage; and
- a control system for selectively extending and retracting the cables by using the motors to cause the arm, carriage and pedal assembly to move relative to the body, such that the pedal assembly is articulated by the control system in prescribed pedaling patterns for the user of the machine.

Clause 2. The machine of any clause herein, wherein the distal end of the arm is free of contact with the motors over an entire range of motion of the arm relative to the body.

Clause 3. The machine of any clause herein, wherein the prescribed pedaling patterns comprise patterns that are circular, elliptical, oval, square, gliding, leg press, stair stepping and vertical up and down.

Clause 4. The machine of any clause herein, wherein the control system limits a range of motion of the carriage and pedal assembly to an area defined by and within locations of the motors.

Clause 5. The machine of any clause herein, wherein the control system permits a range of motion of the carriage and pedal assembly to extend beyond an area defined by and within locations of the motors.

Clause 6. The machine of any clause herein, wherein the control system is further configured, during each of the prescribed pedaling patterns, to control a repetitive speed and resistance of the pedal assembly.

Clause 7. The machine of any clause herein, wherein the machine does not have a seat for the user to sit on while using the machine, such that the user must be seated away from the machine to use the machine.

Clause 8. The machine of any clause herein, wherein the motors comprise exactly three motors that are arranged in a triangular pattern on a first side of the body.

Clause 9. The machine of any clause herein, wherein each motor comprises a pulley rotatably coupled thereto and coupled to a respective one of the cables.

Clause 10. The machine of any clause herein, wherein the carriage comprises pulleys, and each pulley is coupled to a respective one of the cables.

Clause 11. The machine of any clause herein, wherein the arm is mounted on a first side of the body, and the machine further comprises a second side of the body opposite the first side of the body, and a second arm, second carriage, second pedal assembly, additional motors and additional cables coupled to the second side of the body.

Clause 12. The machine of any clause herein, wherein the pedal assembly and the second pedal assembly are configured to be independently articulated by the control system, such that the pedal assembly and a second assembly can be simultaneously articulated in different ones of the prescribed pedaling patterns.

Clause 13. The machine of any clause herein, further comprising a shroud coupled to the body to substantially cover the arm and motors to obstruct pinch points for the user of the machine.

Clause 14. A machine, comprising:
- a body having two sides;
- an arm coupled to each side of the body, each arm having a proximal end and a distal end, the proximal end is pivotally mounted to the body, and the distal end is free to move relative to the body, respectively;
- a carriage slidably mounted to each arm for movement along a length of the arm, respectively;

a pedal assembly rotatably coupled to each carriage for movement with the carriage along the length of the arm, respectively, wherein each pedal assembly is configured to support a foot of a user of the machine.

motors mounted to each side of the body and spaced apart from each other and spaced apart from the distal end of the arm, respectively;

cables coupled to the motors and to the carriage on each side of the body, respectively; and a control system for selectively extending and retracting the cables by using the motors to cause the arms, carriages and pedal assemblies to move relative to the body, such that the pedal assemblies are articulated by the control system in prescribed pedaling patterns for the user of the machine, and the control system is configured to control a repetitive speed and resistance of the pedal assemblies during each of the prescribed pedaling patterns.

Clause 15. The machine of any clause herein, wherein the control system limits a range of motion of the pedal assemblies to an area defined by and within locations of the motors, respectively.

Clause 16. The machine of any clause herein, wherein the control system permits a range of motion of the pedal assemblies to extend beyond an area defined by and within locations of the motors, respectively.

Clause 17. The machine of any clause herein, wherein the machine does not have a seat for the user to sit on while using the machine, such that the user must be seated away from the machine to use the machine.

Clause 18. The machine of any clause herein, wherein each motor comprises a pulley rotatably coupled thereto and coupled to a respective one of the cables.

Clause 19. The machine of any clause herein, wherein each carriage comprises pulleys, and each pulley is coupled to a respective one of the cables; and the pedal assemblies are configured to be independently articulated by the control system, such that each pedal assembly can be simultaneously articulated in different ones of the prescribed pedaling patterns.

Clause 20. The machine of any clause herein, further comprising a shroud coupled to each side of the body to substantially cover the arm and motors, respectively, to obstruct pinch points for the user of the machine.

Clause 21. A computer-implemented system comprising:

an electromechanical machine comprising one or more motors mounted to a body and spaced apart from each other, and a first set of cables, each coupled to a respective one of the motors; and a processing device communicatively coupled to the one or more motors, wherein the processing device executes instructions implementing a control system to:

receive data comprising a treatment plan including one or more prescribed exercises for a user to perform using the electromechanical machine;

generate, based on the data, a motion profile for an assembly of the electromechanical machine, wherein the assembly is coupled to a carriage to enable movement along a length of an arm, wherein the carriage is coupled to each cable of the first set of cables;

execute a transformation function to implement a desired virtual apparatus model using the electromechanical machine, wherein, to implement the desired virtual apparatus model, the transformation function maps the motion profile to one or more coordinates in a domain; and control, using the desired virtual apparatus model, the one or more motors of the electromechanical machine.

Clause 22. The computer-implemented system of any clause herein, wherein the processing device is further configured to control the one or more motors to operate in a plurality of modes comprising an active mode, an active-assist mode, an assisted mode, a passive mode, or some combination thereof.

Clause 23. The computer-implemented system of any clause herein, wherein, using the electromechanical machine by controlling the one or more motors based on the motion profile, the plurality of modes, or some combination thereof, the processing device is further configured to enable performing at least one of the one or more prescribed exercises.

Clause 24. The computer-implemented system of any clause herein, wherein the processing device is further configured to generate, using an artificial intelligence engine, a machine learning model trained to generate the motion profile for the assembly.

Clause 25. The computer-implemented system of any clause herein, wherein the processing device is disposed in a computing device separate from the electromechanical machine, or the processing device is disposed in the electromechanical machine.

Clause 26. The computer-implemented system of any clause herein, wherein the processing device is further configured to:

use a machine learning model trained to control one or more spools of the first set of cables, one or more speeds of the one or more motors, one or more resistances provided by the one or more motors, one or more ranges of motion of the carriage and assembly, or some combination thereof.

Clause 27. The computer-implemented system of any clause herein, wherein the motion profile comprises a line or a geometrical shape.

Clause 28. The computer-implemented system of any clause herein, further comprising:

a headset configured to present, based on a prescribed exercise of the one or more prescribed exercises, a virtual reality element that modifies an appearance in the headset of the electromechanical machine.

Clause 29. The computer-implemented system of any clause herein, further comprising:

a display configured to present, based on a prescribed exercise of the one or more prescribed exercises, an augmented reality element that modifies on the display an appearance of the electromechanical machine.

Clause 30. The computer-implemented system of any clause herein, wherein the assembly comprises a pedal assembly and the pedal assembly is rotatably coupled to the carriage.

Clause 31. The computer-implemented system of any clause herein, wherein the assembly comprises a handlebar assembly, a row assembly, a pedal assembly, a climbable assembly, a step assembly, a paddle assembly, a brace assembly, a lift assembly, a push assembly, or a balance assembly.

Clause 32. A method comprising:

receiving data comprising a treatment plan including one or more prescribed exercises for a user to perform using an electromechanical machine;

generating, based on the data, a motion profile for an assembly of the electromechanical machine, wherein the assembly is coupled to a carriage to enable movement along a length of an arm, wherein the carriage is coupled to each cable of a first set of cables;

executing a transformation function to implement a desired virtual apparatus model using the electromechanical machine, wherein, to implement the desired virtual apparatus model, the transformation function maps the motion profile to one or more coordinates in a domain; and controlling, using the desired virtual apparatus model, the one or more motors of the electromechanical machine.

Clause 33. The method of any clause herein, further comprising controlling the one or more motors to operate in a plurality of modes comprising an active mode, an active-assist mode, an assisted mode, a passive mode, or some combination thereof.

Clause 34. The method of any clause herein, wherein, using the electromechanical machine by controlling the one or more motors based on the motion profile, the plurality of modes, or some combination thereof, the method further comprises enabling performing at least one of the one or more prescribed exercises.

Clause 35. The method of any clause herein, further comprising generating, using an artificial intelligence engine, a machine learning model trained to generate the motion profile for the assembly.

Clause 36. The method of any clause herein, wherein the processing device is disposed in a computing device separate from the electromechanical machine, or the processing device is disposed in the electromechanical machine.

Clause 37. The method of any clause herein, further comprising:

using a machine learning model trained to control one or more spools of the first set of cables, one or more speeds of the one or more motors, one or more resistances provided by the one or more motors, one or more ranges of motion of the carriage and assembly, or some combination thereof.

Clause 38. The method of any clause herein, wherein the motion profile comprises a line or a geometrical shape.

Clause 39. A tangible, non-transitory computer-readable medium storing instructions that, when executed, cause a processing device to:

receive data comprising a treatment plan including one or more prescribed exercises for a user to perform using an electromechanical machine;

generate, based on the data, a motion profile for an assembly of the electromechanical machine, wherein the assembly is coupled to a carriage to enable movement along a length of an arm, wherein the carriage is coupled to each cable of a first set of cables;

execute a transformation function to implement a desired virtual apparatus model using the electromechanical machine, wherein, to implement the desired virtual apparatus model, the transformation function maps the motion profile to one or more coordinates in a domain; and control, using the desired virtual apparatus model, the one or more motors of the electromechanical machine.

Clause 40. The computer-readable medium of any clause herein, wherein the processing device is further to control the one or more motors to operate in a plurality of modes comprising an active mode, an active-assist mode, an assisted mode, a passive mode, or some combination thereof.

Clause 41. A computer-implemented system comprising:

an electromechanical machine comprising one or more motors mounted to a body and spaced apart from each other, and a first set of cables, each coupled to a respective one of the motors; and a processing device communicatively coupled to the one or more motors, wherein the processing device executes instructions implementing a control system to:

receive data comprising a treatment plan, wherein the treatment plan includes one or more prescribed exercises for a user to perform using the electromechanical machine;

generate, based on the data and certain criteria, a motion profile for an assembly of the electromechanical machine, wherein the motion profile comprises a movement shape of one or more portions of the electromechanical machine;

execute a transformation function to implement, using the electromechanical machine, a desired virtual apparatus model, wherein, to implement the desired virtual apparatus model, the transformation function maps the motion profile to one or more coordinates in a domain; and control, using the desired virtual apparatus model, the one or more motors of the electromechanical machine.

Clause 42. The computer-implemented system of any clause herein, wherein the certain criteria comprise:

one or more muscle groups, one or more user attributes comprising height, weight, demographic characteristics, psychographic characteristics, race, gender, medical history, comorbidities, prescription medications, non-prescription medications or nutritional supplements, familial medical history, and performed medical procedures on the user, one or more desired results, or some combination thereof.

Clause 43. The computer-implemented system of any clause herein, wherein the assembly is coupled to a carriage to enable movement along a length of an arm, wherein the carriage is coupled to each cable of the first set of cables.

Clause 44. The computer-implemented system of any clause herein, wherein the processing device is further configured to control the one or more motors to operate in a plurality of modes comprising an active mode, an active-assist mode, an assisted mode, a passive mode, or some combination thereof.

Clause 45. The computer-implemented system of any clause herein, wherein, by using the electromechanical machine in order to control the one or more motors based on the motion profile, the plurality of modes, or some combination thereof, the processing device is further configured to enable performing at least one of the one or more prescribed exercises.

Clause 46. The computer-implemented system of any clause herein, wherein the movement shape comprises a line or a geometrical shape.

Clause 47. The computer-implemented system of any clause herein, further comprising:

a headset configured to present, based on a prescribed exercise of the one or more prescribed exercises, a virtual reality element that modifies an appearance in the headset of the electromechanical machine.

Clause 48. The computer-implemented system of any clause herein, further comprising:

a display configured to present, based on a prescribed exercise of the one or more prescribed exercises, an augmented reality element that modifies on the display an appearance of the electromechanical machine.

Clause 49. A method comprising:

receiving data comprising a treatment plan, wherein the treatment plan includes one or more prescribed exercises for a user to perform using an electromechanical machine;

generating, based on the data and certain criteria, a motion profile for an assembly of the electromechanical machine, wherein the motion profile comprises a movement shape of one or more portions of the electromechanical machine;

executing a transformation function to implement, using the electromechanical machine, a desired virtual apparatus model, wherein, to implement the desired virtual apparatus model, the transformation function maps the motion profile to one or more coordinates in a domain; and controlling, using the desired virtual apparatus model, the one or more motors of the electromechanical machine.

Clause 50. The method of any clause herein, wherein the certain criteria comprise:

one or more muscle groups, one or more user attributes comprising height, weight, demographic characteristics, psychographic characteristics, race, gender, medical history, comorbidities, prescription medications, non-prescription medications or nutritional supplements, familial medical history, and performed medical procedures on the user, one or more desired results, or some combination thereof.

Clause 51. The method of any clause herein, wherein the assembly is coupled to a carriage to enable movement along a length of an arm, wherein the carriage is coupled to each cable of the first set of cables.

Clause 52. The method of any clause herein, further comprising controlling the one or more motors to operate in a plurality of modes comprising an active mode, an active-assist mode, an assisted mode, a passive mode, or some combination thereof.

Clause 53. The method of any clause herein, wherein, by using the electromechanical machine in order to control the one or more motors based on the motion profile, the plurality of modes, or some combination thereof, the method further comprises enabling performing at least one of the one or more prescribed exercises.

Clause 54. The method of any clause herein, wherein the movement shape comprises a line or a geometrical shape.

Clause 55. The method of any clause herein, further comprising:

a headset configured to present, based on a prescribed exercise of the one or more prescribed exercises, a virtual reality element that modifies an appearance in the headset of the electromechanical machine.

Clause 56. The method of any clause herein, further comprising:

a display configured to present, based on a prescribed exercise of the one or more prescribed exercises, an augmented reality element that modifies on the display an appearance of the electromechanical machine.

Clause 57. A tangible, non-transitory computer-readable medium storing instructions that, when executed, cause a processing device to:

receive data comprising a treatment plan, wherein the treatment plan includes one or more prescribed exercises for a user to perform using an electromechanical machine;

generate, based on the data and certain criteria, a motion profile for an assembly of the electromechanical machine, wherein the motion profile comprises a movement shape of one or more portions of the electromechanical machine;

execute a transformation function to implement, using the electromechanical machine, a desired virtual apparatus model, wherein, to implement the desired virtual apparatus model, the transformation function maps the motion profile to one or more coordinates in a domain; and control, using the desired virtual apparatus model, the one or more motors of the electromechanical machine.

Clause 58. The computer-readable medium of any clause herein, wherein the certain criteria comprise:

one or more muscle groups, one or more user attributes comprising height, weight, demographic characteristics, psychographic characteristics, race, gender, medical history, comorbidities, prescription medications, non-prescription medications or nutritional supplements, familial medical history, and performed medical procedures on the user, one or more desired results, or some combination thereof.

Clause 59. The computer-readable medium of any clause herein, wherein the assembly is coupled to a carriage to enable movement along a length of an arm, wherein the carriage is coupled to each cable of the first set of cables.

Clause 60. The computer-readable medium of any clause herein, wherein the processing device is further configured to control the one or more motors to operate in a plurality of modes comprising an active mode, an active-assist mode, an assisted mode, a passive mode, or some combination thereof.

Clause 61. A computer-implemented system comprising:

an electromechanical machine comprising one or more motors mounted to a body and spaced apart from each other, and a first set of cables, each coupled to a respective one of the motors; and a processing device communicatively coupled to the one or more motors, wherein the processing device executes instructions implementing a control system to:

receive first data comprising information pertaining to motion of one or more pedals of the electromechanical machine, wherein the motion is associated with one or more users performing one or more treatment plans;

receive second data comprising information pertaining to one or more characteristics of the one or more users performing the treatment plan, wherein the characteristics comprise performance information, measurement information, personal information, or some combination thereof;

identify one or more correlations between at least some of the first data and at least some of the second data; and generate, based on the one or more treatment plans and the one or more correlations, one or more motion profiles for an assembly of the electromechanical machine.

Clause 62. The computer-implemented system of any clause herein, wherein the processing device is further configured to:

receive a prescribed treatment plan for a user;

select, based on the prescribed treatment plan, a motion profile from the one or more motion profiles to be performed by the user, wherein the motion profile is configured to provide a desired result.

Clause 63. The computer-implemented system of any clause herein, wherein the processing device is further configured to execute a transformation function to implement, using the electromechanical machine, a desired virtual apparatus model, wherein, to implement the desired virtual apparatus model, the transformation function maps the motion profile to one or more coordinates in a domain.

Clause 64. The computer-implemented system of any clause herein, wherein the processing device is further configured to control, using the desired virtual apparatus model, the one or more motors of the electromechanical machine.

Clause 65. The computer-implemented system of any clause herein, wherein the one or more correlations pertain to one or more results achieved with respect to a threshold achievement level measured in relation to the one or more characteristics.

Clause 66. The computer-implemented system of any clause herein, wherein the processing device is further configured to control the one or more motors to operate in a plurality of modes comprising an active mode, an active-assist mode, an assisted mode, a passive mode, or some combination thereof.

Clause 67. The computer-implemented system of any clause herein, wherein the processing device is further configured to use a machine learning model trained to control one or more spools of the first set of cables, one or more speeds of the one or more motors, one or more resistances provided by the one or more motors, one or more ranges of motion of the carriage and assembly, or some combination thereof.

Clause 68. A method comprising:

receiving first data comprising information pertaining to motion of one or more pedals of an electromechanical machine, wherein the motion is associated with one or more users performing one or more treatment plans;

receiving second data comprising information pertaining to one or more characteristics of the one or more users performing the treatment plan, wherein the characteristics comprise performance information, measurement information, personal information, or some combination thereof;

identifying one or more correlations between at least some of the first data and at least some of the second data; and generating, based on the one or more treatment plans and the one or more correlations, one or more motion profiles for an assembly of the electromechanical machine.

Clause 69. The method of any clause herein, further comprising:

receiving a prescribed treatment plan for a user;

selecting, based on the prescribed treatment plan, a motion profile from the one or more motion profiles to be performed by the user, wherein the motion profile is configured to provide a desired result.

Clause 70. The method of any clause herein, further comprising executing a transformation function to implement, using the electromechanical machine, a desired virtual apparatus model, wherein, to implement the desired virtual apparatus model, the transformation function maps the motion profile to one or more coordinates in a domain.

Clause 71. The method of any clause herein, further comprising controlling, using the desired virtual apparatus model, the one or more motors of the electromechanical machine.

Clause 72. The method of any clause herein, wherein the one or more correlations pertain to one or more results achieved with respect to a threshold achievement level measured in relation to the one or moe characteristics.

Clause 73. The method of any clause herein, further comprising controlling the one or more motors to operate in a plurality of modes comprising an active mode, an active-assist mode, an assisted mode, a passive mode, or some combination thereof.

Clause 74. The method of any clause herein, further comprising using a machine learning model trained to control one or more spools of the first set of cables, one or more speeds of the one or more motors, one or more resistances provided by the one or more motors, one or more ranges of motion of the carriage and assembly, or some combination thereof.

Clause 75. A tangible, non-transitory computer-readable medium storing instructions that, when executed, cause a processing device to:

receive first data comprising information pertaining to motion of one or more pedals of an electromechanical machine, wherein the motion is associated with one or more users performing one or more treatment plans;

receive second data comprising information pertaining to one or more characteristics of the one or more users performing the treatment plan, wherein the characteristics comprise performance information, measurement information, personal information, or some combination thereof;

identify one or more correlations between at least some of the first data and at least some of the second data; and generate, based on the one or more treatment plans and the one or more correlations, one or more motion profiles for an assembly of the electromechanical machine.

Clause 76. The computer-readable medium of any clause herein, wherein the processing device is further configured to:

receive a prescribed treatment plan for a user;

select, based on the prescribed treatment plan, a motion profile from the one or more motion profiles to be performed by the user, wherein the motion profile is configured to provide a desired result.

Clause 77. The computer-readable medium of any clause herein, wherein the processing device is further configured to execute a transformation function to implement, using the electromechanical machine, a desired virtual apparatus model, wherein, to implement the desired virtual apparatus model, the transformation function maps the motion profile to one or more coordinates in a domain.

Clause 78. The computer-readable medium of any clause herein, wherein the processing device is further configured to control, using the desired virtual apparatus model, the one or more motors of the electromechanical machine.

Clause 79. The computer-readable medium of any clause herein, wherein the one or more correlations pertain to one or more results achieved with respect to a threshold achievement level measured in relation to the one or more characteristics.

Clause 80. The computer-readable medium of any clause herein, wherein the processing device is further configured to control the one or more motors to operate in a plurality of modes comprising an active mode, an active-assist mode, an assisted mode, a passive mode, or some combination thereof.

Clause 81. A computer-implemented system comprising:

an electromechanical machine comprising one or more motors mounted to a body and spaced apart from each other, and a first set of cables, each coupled to a respective one of the motors; and a processing device communicatively coupled to the one or more motors, wherein the processing device executes instructions implementing a control system to:

receive data comprising a treatment plan including one or more prescribed exercises for a user to perform using the electromechanical machine;

generate, based on the data, a motion profile for an assembly of the electromechanical machine;

determine, based on a prescribed exercise of the one or more prescribed exercises, one or more components to include to enable the user to perform, using the electromechanical machine, the prescribed exercise;

validate, based on the one or more components and configuration information pertaining to the electromechanical machine, whether the motion profile associated with the prescribed exercise is achievable with respect to a threshold achievement level; and responsive to determining that the motion profile associated with the prescribed exercise is unachievable with respect to the threshold achievement level, determining, based on the one or more components and the configuration information, at least one missing component needed to achieve, with respect to the threshold achievement level, the motion profile for the prescribed exercise.

Clause 82. The computer-implemented system of any clause herein, wherein the processing device is further configured to generate and output an electromechanical machine configuration file, wherein the electromechanical machine configuration file includes information pertaining to the at least one missing component.

Clause 83. The computer-implemented system of any clause herein, wherein the processing device is further configured to transmit a recommendation to a computing device, wherein the recommendation is associated with a payment system that enables purchasing the at least one missing component.

Clause 84. The computer-implemented system of any clause herein, wherein, responsive to determining the motion profile associated with the prescribed exercise is achievable with respect to the threshold achievement level, execute a transformation function to implement a desired virtual apparatus model configured to implement, by using the electromechanical machine, the motion profile, wherein, to implement the desired virtual apparatus model, the transformation function maps the motion profile to one or more coordinates in a domain.

Clause 85. The computer-implemented system of any clause herein, wherein the processing device is further to control, using the desired virtual apparatus model, the one or more motors of the electromchanical machine.

Clause 86. The computer-implemented system of any clause herein, wherein the assembly is coupled to a carriage to enable movement along a length of an arm, wherein the carriage is coupled to each cable of the first set of cables.

Clause 87. The computer-implemented system of any clause herein, wherein the processing device is further configured to control the one or more motors to operate in a plurality of modes comprising an active mode, an active-assist mode, an assisted mode, a passive mode, or some combination thereof.

Clause 88. A method comprising:

receiving data comprising a treatment plan including one or more prescribed exercises for a user to perform using the electromechanical machine;

generate, based on the data, a motion profile for an assembly of the electromechanical machine;

determining, based on a prescribed exercise of the one or more prescribed exercises, one or more components to include to enable the user to perform, using the electromechanical machine, the prescribed exercise;

validating, based on the one or more components and configuration information pertaining to the electromechanical machine, whether the motion profile associated with the prescribed exercise is achievable with respect to a threshold achievement level; and responsive to determining that the motion profile associated with the prescribed exercise is unachievable with respect to the threshold achievement level, determining, based on the one or more components and the configuration information, at least one missing component needed to achieve, with respect to the threshold achievement level, the motion profile for the prescribed exercise.

Clause 89. The method of any clause herein, further comprising generating and output an electromechanical machine configuration file, wherein the electromechanical machine configuration file includes information pertaining to the at least one missing component.

Clause 90. The method of any clause herein, further comprising transmitting a recommendation to a computing device, wherein the recommendation is associated with a payment system that enables purchasing the at least one missing component.

Clause 91. The method of any clause herein, further comprising, responsive to determining the motion profile associated with the prescribed exercise is achievable with respect to the threshold achievement level, executing a transformation function to implement a desired virtual apparatus model configured to implement, by using the electromechanical machine, the motion profile, wherein, to implement the desired virtual apparatus model, the transformation function maps the motion profile to one or more coordinates in a domain.

Clause 92. The method of any clause herein, further comprising controlling, using the desired virtual apparatus model, the one or more motors of the electromechanical machine.

Clause 93. The method of any clause herein, wherein the assembly is coupled to a carriage to enable movement along a length of an arm, wherein the carriage is coupled to each cable of the first set of cables.

Clause 94. The method of any clause herein, further comprising controlling the one or more motors to operate in a plurality of modes comprising an active mode, an active-assist mode, an assisted mode, a passive mode, or some combination thereof.

Clause 95. A tangible, non-transitory computer-readable medium storing instructions that, when executed, cause a processing device to:

receive data comprising a treatment plan including one or more prescribed exercises for a user to perform using an electromechanical machine;

generate, based on the data, a motion profile for an assembly of the electromechanical machine;

determine, based on a prescribed exercise of the one or more prescribed exercises, one or more components to include to enable the user to perform, using the electromechanical machine, the prescribed exercise;

validate, based on the one or more components and configuration information pertaining to the electromechanical machine, whether the motion profile associated with the prescribed exercise is achievable with respect to a threshold achievement level; and responsive to determining that the motion profile associated with the prescribed exercise is unachievable with respect to the threshold achievement level, determining, based on the one or more components and the configuration information, at least one missing component needed to achieve, with respect to the threshold achievement level, the motion profile for the prescribed exercise.

Clause 96. The computer-readable medium of any clause herein, wherein the processing device is further configured to generate and output an electromechanical machine configuration file, wherein the electromechanical machine configuration file includes information pertaining to the at least one missing component.

Clause 97. The computer-readable medium of any clause herein, wherein the processing device is further configured to transmit a recommendation to a computing device, wherein the recommendation is associated with a payment system that enables purchasing the at least one missing component.

Clause 98. The computer-readable medium of any clause herein, wherein, responsive to determining the motion profile associated with the prescribed exercise is achievable with respect to the threshold achievement level, execute a transformation function to implement a desired virtual apparatus model configured to implement, by using the electromechanical machine, the motion profile, wherein, to implement the desired virtual apparatus model, the transformation function maps the motion profile to one or more coordinates in a domain.

Clause 99. The computer-readable medium of any clause herein, wherein the processing device is further to control, using the desired virtual apparatus model, the one or more motors of the electromechanical machine.

Clause 100. The computer-readable medium of any clause herein, wherein the assembly is coupled to a carriage to enable movement along a length of an arm, wherein the carriage is coupled to each cable of the first set of cables.

Clause 101. A computer-implemented system comprising:

an electromechanical machine comprising one or more motors mounted to a body and spaced apart from each other, and a first set of cables, each coupled to a respective one of the motors; and a processing device communicatively coupled to the one or more motors, wherein the processing device executes instructions implementing a control system to:

receive data comprising a treatment plan including one or more prescribed exercises for a user to perform using the electromechanical machine, generate, using a treatment machine description language and based on one or more desired goals of a user, a virtual apparatus model of the electromechanical machine, wherein the virtual apparatus model is generated by a trained machine learning model; and generate, using the virtual apparatus model and the data, a motion profile; and control, using the motion profile, the one or more motors.

Clause 102. The computer-implemented system of any clause herein, wherein the treatment machine description language comprises a canonical format including tags identifying values of at least some target information, tags implementing an attribute grammar, tags used for lexical comparisons or equivalence scores, or some combination thereof.

Clause 103. The computer-implemented system of any clause herein, wherein the virtual apparatus model comprises a list of components to use to enable achieving the one or more desired goals, wherein the achieving is measured with respect to a threshold achievement level.

Clause 104. The computer-implemented system of any clause herein, wherein the list of components is associated with the electromechanical machine, another electromechanical machine, an accessory, an apparatus, or some combination thereof.

Clause 105. The computer-implemented system of any clause herein, further comprising:

a headset configured to present, based on a prescribed exercise of the one or more prescribed exercises, a virtual reality element that modifies in the headset an appearance of the electromechanical machine.

Clause 106. The computer-implemented system of any clause herein, further comprising:

a display configured to present, based on a prescribed exercise of the one or more prescribed exercises, an augmented reality element that modifies on the display an appearance of the electromechanical machine.

Clause 107. The computer-implemented system of any clause herein, wherein the processing device is further configured to generate, using an artificial intelligence engine, a machine learning model trained to generate the motion profile for the assembly.

Clause 108. A method comprising:

receiving data comprising a treatment plan including one or more prescribed exercises for a user to perform using an electromechanical machine, generating, using a treatment machine description language and based on one or more desired goals of a user, a virtual apparatus model of the electromechanical machine, wherein the virtual apparatus model is generated by a trained machine learning model; and generating, using the virtual apparatus model and the data, a motion profile; and controlling, using the motion profile, the one or more motors.

Clause 109. The method of any clause herein, wherein the treatment machine description language comprises a canonical format including tags identifying values of at least some target information, tags implementing an attribute grammar, tags used for lexical comparisons or equivalence scores, or some combination thereof.

Clause 110. The method of any clause herein, wherein the virtual apparatus model comprises a list of components to use to enable achieving the one or more desired goals, wherein the achieving is measured with respect to a threshold achievement level.

Clause 111. The method of any clause herein, wherein the list of components is associated with the electromechanical machine, another electromechanical machine, an accessory, an apparatus, or some combination thereof.

Clause 112. The method of any clause herein, further comprising:

a headset configured to present, based on a prescribed exercise of the one or more prescribed exercises, a virtual reality element that modifies in the headset an appearance of the electromechanical machine.

Clause 113. The method of any clause herein, further comprising:

a display configured to present, based on a prescribed exercise of the one or more prescribed exercises, an augmented reality element that modifies on the display an appearance of the electromechanical machine.

Clause 114. The method of any clause herein, further comprising generating, using an artificial intelligence engine, a machine learning model trained to generate the motion profile for the assembly.

Clause 115. A tangible, non-transitory computer-readable medium storing instructions that, when executed, cause a processing device to:

receive data comprising a treatment plan including one or more prescribed exercises for a user to perform using an electromechanical machine, generate, using a treatment machine description language and based on one or more desired goals of a user, a virtual apparatus model of the electromechanical machine, wherein the virtual apparatus model is generated by a trained machine learning model; and generate, using the virtual apparatus model and the data, a motion profile; and control, using the motion profile, the one or more motors.

Clause 116. The computer-readable medium of any clause herein, wherein the treatment machine description language comprises a canonical format including tags identifying values of at least some target information, tags implementing an attribute grammar, tags used for lexical comparisons or equivalence scores, or some combination thereof.

Clause 117. The computer-readable medium of any clause herein, wherein the virtual apparatus model comprises a list of components to use to enable achieving the one or more desired goals, wherein the achieving is measured with respect to a threshold achievement level.

Clause 118. The computer-readable medium of any clause herein, wherein the list of components is associated with the electromechanical machine, another electromechanical machine, an accessory, an apparatus, or some combination thereof.

Clause 119. The computer-readable medium of any clause herein, further comprising:

a headset configured to present, based on a prescribed exercise of the one or more prescribed exercises, a virtual reality element that modifies in the headset an appearance of the electromechanical machine.

Clause 120. The computer-readable medium of any clause herein, further comprising:

a display configured to present, based on a prescribed exercise of the one or more prescribed exercises, an augmented reality element that modifies on the display an appearance of the electromechanical machine.

We claim:

1. A computer-implemented system comprising:

an electromechanical machine comprising a set of motors mounted to a body and spaced apart from each other, a first set of cables, each coupled to a respective one of the set of motors, and an assembly coupled to the first set of cables; and a processing device communicatively coupled to the set of motors, wherein the processing device executes instructions implementing a control system to:

receive data comprising a treatment plan including one or more prescribed exercises for a user to perform using the electromechanical machine;

generate, based on the data, a motion profile for the assembly of the electromechanical machine;

determine, based on a prescribed exercise of the one or more prescribed exercises, one or more components to include to enable the user to perform, using the electromechanical machine, the prescribed exercise;

validate, based on the one or more components and configuration information pertaining to the electromechanical machine, whether the motion profile associated with the prescribed exercise is achievable with respect to a threshold achievement level;

responsive to determining that the motion profile associated with the prescribed exercise is unachievable with respect to the threshold achievement level, determine, based on the one or more components and the configuration information, at least one missing component needed to achieve, with respect to the threshold achievement level, the motion profile for the prescribed exercise; and responsive to determining that the motion profile associated with the prescribed exercise is achievable with respect to the threshold achievement level, control the set of motors to implement the motion profile.

2. The computer-implemented system of claim 1, wherein the processing device is further configured to generate and output an electromechanical machine configuration file, wherein the electromechanical machine configuration file includes information pertaining to the at least one missing component.

3. The computer-implemented system of claim 2, wherein the processing device is further configured to transmit a recommendation to a computing device, wherein the recommendation is associated with a payment system that enables purchasing the at least one missing component.

4. The computer-implemented system of claim 1, wherein controlling the set of motors to implement the motion profile comprises executing a transformation function to implement a desired virtual apparatus model configured to implement, using the electromechanical machine, the motion profile, and wherein, to implement the desired virtual apparatus model, the transformation function maps the motion profile to one or more coordinates in a domain.

5. The computer-implemented system of claim 4, wherein controlling the set of motors to implement the motion profile further comprises controlling the set of motors using the desired virtual apparatus model.

6. The computer-implemented system of claim 1, wherein the assembly is coupled to a carriage to enable movement along a length of an arm, and wherein the carriage is coupled to each cable of the first set of cables.

7. A method comprising:

receiving data comprising a treatment plan including one or more prescribed exercises for a user to perform using an electromechanical machine;

generating, based on the data, a motion profile for an assembly of the electromechanical machine;

determining, based on a prescribed exercise of the one or more prescribed exercises, one or more components to include to enable the user to perform, using the electromechanical machine, the prescribed exercise;

validating, based on the one or more components and configuration information pertaining to the electromechanical machine, whether the motion profile associated with the prescribed exercise is achievable with respect to a threshold achievement level;

responsive to determining that the motion profile associated with the prescribed exercise is unachievable with respect to the threshold achievement level, determining, based on the one or more components and the configuration information, at least one missing component needed to achieve, with respect to the threshold achievement level, the motion profile for the prescribed exercise; and responsive to determining that the motion profile associated with the prescribed exercise is achievable with respect to the threshold achievement level, controlling one or more motors of the electromechanical machine, coupled to the assembly, to implement the motion profile.

8. The method of claim 7, further comprising generating and output an electromechanical machine configuration file, wherein the electromechanical machine configuration file includes information pertaining to the at least one missing component.

9. The method of claim 8, further comprising transmitting a recommendation to a computing device, wherein the recommendation is associated with a payment system that enables purchasing the at least one missing component.

10. The method of claim 7, wherein controlling the one or more motors of the electromechanical machine to implement the motion profile comprises executing a transformation function to implement a desired virtual apparatus model configured to implement, using the electromechanical machine, the motion profile, and wherein, to implement the desired virtual apparatus model, the transformation function maps the motion profile to one or more coordinates in a domain.

11. The method of claim 10, wherein controlling the one or more motors of the electromechanical machine to implement the motion profile further comprises controlling the one or more motors of the electromechanical machine using the desired virtual apparatus model.

12. The method of claim 7, wherein the assembly is coupled to a carriage to enable movement along a length of an arm, and wherein the carriage is coupled to each cable of a first set of cables of the electromechanical machine.

13. A tangible, non-transitory computer-readable medium storing instructions that, when executed, cause a processing device to:

receive data comprising a treatment plan including one or more prescribed exercises for a user to perform using an electromechanical machine;

generate, based on the data, a motion profile for an assembly of the electromechanical machine;

determine, based on a prescribed exercise of the one or more prescribed exercises, one or more components to include to enable the user to perform, using the electromechanical machine, the prescribed exercise;

validate, based on the one or more components and configuration information pertaining to the electromechanical machine, whether the motion profile associated with the prescribed exercise is achievable with respect to a threshold achievement level;

responsive to determining that the motion profile associated with the prescribed exercise is unachievable with respect to the threshold achievement level, determine, based on the one or more components and the configuration information, at least one missing component needed to achieve, with respect to the threshold achievement level, the motion profile for the prescribed exercise; and responsive to determining that the motion profile associated with the prescribed exercise is achievable with respect to the threshold achievement level, control one or more motors of the electromechanical machine, coupled to the assembly, to implement the profile motion.

14. The computer-readable medium of claim 13, wherein the processing device is further configured to generate and output an electromechanical machine configuration file, wherein the electromechanical machine configuration file includes information pertaining to the at least one missing component.

15. The computer-readable medium of claim 14, wherein the processing device is further configured to transmit a recommendation to a computing device, wherein the recommendation is associated with a payment system that enables purchasing the at least one missing component.

16. The computer-readable medium of claim 13, wherein controlling the one or more motors of the electromechanical machine to implement the motion profile comprises executing a transformation function to implement a desired virtual apparatus model configured to implement, using the electromechanical machine, the motion profile, and wherein, to implement the desired virtual apparatus model, the transformation function maps the motion profile to one or more coordinates in a domain.

17. The computer-readable medium of claim 16, wherein controlling the one or more motors of the electromechanical machine to implement the motion profile further comprises controlling the one or more motors of the electromechanical machine using the desired virtual apparatus model.

18. The computer-readable medium of claim 13, wherein the assembly is coupled to a carriage to enable movement along a length of an arm, and wherein the carriage is coupled to each cable of a first set of cables of the electromechanical machine.

* * * * *